United States Patent
Manning et al.

(10) Patent No.: US 8,710,047 B2
(45) Date of Patent: *Apr. 29, 2014

(54) 5-HT$_3$ RECEPTOR MODULATORS, METHODS OF MAKING, AND USE THEREOF

(71) Applicant: Albany Molecular Research, Inc., Albany, NY (US)

(72) Inventors: David D. Manning, Duanesburg, NY (US); Christopher L. Cioffi, Troy, NY (US)

(73) Assignee: Albany Molecular Research, Inc., Albany, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/941,304

(22) Filed: Jul. 12, 2013

(65) Prior Publication Data

US 2013/0310366 A1    Nov. 21, 2013

Related U.S. Application Data

(63) Continuation of application No. 13/372,967, filed on Feb. 14, 2012, now Pat. No. 8,501,729, which is a continuation of application No. 12/473,940, filed on May 28, 2009, now Pat. No. 8,124,600.

(60) Provisional application No. 61/057,014, filed on May 29, 2008.

(51) Int. Cl.
| C07D 471/06 | (2006.01) |
| C07D 487/06 | (2006.01) |
| C07D 519/00 | (2006.01) |
| A61K 31/55 | (2006.01) |
| A61P 25/00 | (2006.01) |

(52) U.S. Cl.
USPC ........... 514/212.06; 540/520; 546/82; 546/84

(58) Field of Classification Search
USPC ................... 514/212.06; 540/520; 546/82, 84
See application file for complete search history.

(56) References Cited

U.S. PATENT DOCUMENTS

| 4,910,193 | A | 3/1990 | Buchheit |
| 5,756,514 | A | 5/1998 | Larijani |
| 6,380,193 | B1 | 4/2002 | Li et al. |
| 6,770,655 | B2 | 8/2004 | Zhang et al. |
| 6,906,096 | B2 | 6/2005 | Alper et al. |
| 7,125,886 | B2 | 10/2006 | Zhang et al. |
| 7,307,094 | B2 | 12/2007 | Fairfax et al. |
| 7,553,846 | B2 | 6/2009 | Yang et al. |
| 7,863,271 | B2 | 1/2011 | Yang et al. |
| 2004/0106597 | A1 | 6/2004 | May et al. |
| 2005/0101618 | A1 | 5/2005 | Connell et al. |
| 2006/0183769 | A1 | 8/2006 | Fairfax et al. |
| 2007/0032469 | A1 | 2/2007 | Isaac et al. |
| 2007/0066663 | A1 | 3/2007 | Beadle et al. |
| 2007/0197580 | A1 | 8/2007 | Zhang et al. |
| 2007/0259933 | A1 | 11/2007 | Virsik et al. |
| 2007/0265277 | A1 | 11/2007 | Jikyo et al. |
| 2008/0021095 | A1 | 1/2008 | Chen et al. |
| 2008/0039462 | A1 | 2/2008 | Dunn et al. |
| 2008/0293694 | A1 | 11/2008 | Angbrant et al. |

FOREIGN PATENT DOCUMENTS

| DE | 3810552 A1 | 10/1989 |
| EP | 0 457 243 A1 | 11/1991 |
| JP | H05202052 A | 8/1993 |
| JP | 2004532887 A | 10/2004 |
| WO | 99/59975 A1 | 11/1999 |
| WO | 02/44183 A2 | 6/2002 |
| WO | 2004/014294 A2 | 2/2004 |
| WO | 2005/058915 A1 | 6/2005 |
| WO | 2005/058925 A1 | 6/2005 |
| WO | 2007/117180 A1 | 10/2007 |
| WO | 2011/008572 A2 | 1/2011 |

OTHER PUBLICATIONS

Houlihan et al., "Novel Cycloaddition Products Formed by the Modified Madelung Indole Synthesis," J. Org. Chem. 46:4515-7 (1981).
International Search Report for International Patent Application No. PCT/US09/45484 (Dec. 4, 2009).
Written Opinion of the International Searching Authority for International Patent Application No. PCT/US09/45484 (Dec. 4, 2009).
CAS Registry No. 1112378-24-1 (Feb. 26, 2009).
Communication dated May 3, 2011 for EP 09767365.
Israeli, "Clinical Pharmacology of Serotonin Receptor Type 3 (5-HT3) Antagonists," Curr. Med. Chem.—Central Nervous System Agents, 1:171-199 (2001).
Costall, "5-HT3 Receptors," Curr. Drug Targets—CNS and Neurological Disorders 3:27-37 (2004).
First Office Action for China Patent Application No. 200980119763.5, dated Mar. 31, 2012 (translation).
Blum et al., "Design and Synthesis of Novel Ligands for the 5-HT(3) and the 5-HT(4) Receptor," Bioorgan. Med. Chem. Lett. 2(5):461-466 (1992).
Translation of Notice of Reasons for Rejection for Japan Patent Application No. 2011-511820 (Sep. 4, 2013).
Examination Report for Singapore Patent Application No. 201007938-2 (Jul. 4, 2013).
Examination Report for Israel Patent Application No. 208939 (Feb. 17, 2013).
Written Opinion and Search Report for Singapore Patent Application No. 201007938-2 (Oct. 31, 2012).

*Primary Examiner* — Bruck Kifle
(74) *Attorney, Agent, or Firm* — LeClairRyan, a Professional Corporation

(57) ABSTRACT

Novel 5-HT$_3$ receptor modulators are disclosed. These compounds are used in the treatment of various disorders, including chemotherapy-induced nausea and vomiting, post-operative nausea and vomiting, and irritable bowel syndrome. Methods of making these compounds are also described in the present invention.

10 Claims, No Drawings

> # 5-HT₃ RECEPTOR MODULATORS, METHODS OF MAKING, AND USE THEREOF

This application is a continuation of U.S. patent application Ser. No. 13/372,967, filed Feb. 14, 2012, which is a continuation of U.S. patent application Ser. No. 12/473,940, filed May 28, 2009, now U.S. Pat. No. 8,124,600, which claims benefit of U.S. Provisional Patent Application Ser. No. 61/057,014, filed May 29, 2008, which are hereby incorporated by reference in their entirety.

FIELD OF THE INVENTION

The present invention relates to serotonin type-3 ($5$-$HT_3$) receptor modulators, compositions, their use in the treatment of diseases in which the $5$-$HT_3$ receptor is implicated, for example, in the treatment of Irritable Bowel Syndrome (IBS), chemotherapy-induced nausea and vomiting (CINV), and post-operative nausea and vomiting (PONV), and the use of the compounds in combination therapy. The present invention also relates to methods of synthesis of the $5$-$HT_3$ receptor modulators.

BACKGROUND OF THE INVENTION

Irritable Bowel Syndrome (IBS) has a major impact on the healthcare system in that IBS management in the U.S. is estimated to cost 8 billion dollars annually in direct medical care costs and as high as 25 billion dollars in indirect economic costs.

At present, compounds that alter the activity of certain serotonin receptors are the only approved pharmaceutical treatments for IBS. To that end, the only U.S. drug currently approved for diarrhea predominant IBS is alosetron, a serotonin type-3 ($5$-$HT_3$) receptor inhibitor. This drug was introduced by Glaxo, withdrawn by the FDA due to rare occurrences of ischemic colitis, and then reinstated by the FDA because the demand was so great for a treatment for this disease. In 2002, the US Food and Drug Administration approved alosetron hydrochloride (LOTRONEX®) tablets under restricted conditions for patients in whom the medical benefits outweigh the risks.

$5$-$HT_3$ receptor modulators with improved safety profiles are therefore highly desired for the treatment of IBS. A $5$-$HT_3$ receptor modulator is an agent which can either inhibit (e.g., an antagonist) or partially activate (e.g., a partial agonist) the $5$-$HT_3$ receptor. Indeed, a number of $5$-$HT_3$ receptor modulators are progressing through clinical trials for the treatment of IBS. Exemplary compounds include ramosetron, renzapride, DDP225, and DDP733.

Nausea and vomiting caused by chemotherapy remain among the most distressing side effects for patients undergoing treatment for cancer. Depending upon the chemotherapy agents or regimens given, up to 90% of patients may suffer from some form of chemotherapy-induced nausea and vomiting (CINV). Symptoms from CINV can be severely debilitating and often result in patients refusing further courses of chemotherapy, with obviously unfavorable consequences as regards to progression of the cancer. Furthermore, CINV is burdensome on the medical system, consuming time from the healthcare staff, who could otherwise attend to other patients or medical issues.

CINV is divided into two main categories: acute CINV and delayed CINV. Acute CINV occurs within the first 24 hours of treatment; delayed CINV occurs from 24 hours to 120 hours following treatment. Delayed CINV remains a highly under treated side effect in patients undergoing chemotherapy, as healthcare providers tend to underestimate the number of patients who suffer from delayed CINV. Furthermore, delayed CINV greatly impairs patients' ability to provide care to themselves once they have been discharged.

Compounds that target $5$-$HT_3$ receptors are currently the most effective anti-emetics; they constitute the single greatest advance in the management of nausea and vomiting in patients with cancer. Blocking the $5$-$HT_3$ receptor signal in the CNS or periphery appears to prevent acute emesis. All approved $5$-$HT_3$ receptor modulators, except palonosetron (ALOXI®), are approved to prevent acute CINV. Palonosetron is the only $5$-$HT_3$ receptor modulator currently approved for the prevention of delayed CINV. In addition, the combination of the neurokinin antagonist aprepitant (EMEND®), a $5$-$HT_3$ receptor modulator, and the corticosteroid dexamethasone has been shown to be highly effective in preventing both acute and delayed cisplatin-induced emesis.

Palonosetron has received recent approval for the treatment of post operative nausea and vomiting (PONV). Therefore, $5$-$HT_3$ receptor modulators may be useful for the treatment of PONV.

Clearly, there is a need for improved therapy for IBS, CINV, and PONV. The present invention is directed to achieving this objective.

SUMMARY OF THE INVENTION

The present invention relates to compounds of formula I:

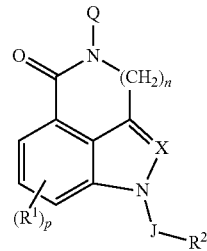

formula I wherein:

Q is a saturated, bicyclic, heterocyclic amine, wherein the saturated, bicyclic, heterocyclic amine comprises at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, —$OR^7$, and —$NR^7R^8$;

X is CH, $CR^3$, or N;

J is selected from the group consisting of a direct bond, C=O, and $SO_2$;

each $R^1$ is independently selected from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^2$ is selected from the group consisting of H, halogen, —$OR^7$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, with the proviso that when J=$SO_2$, R is not H, and wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^3$ is selected from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^6$ is $C_1$-$C_4$ alkyl, $C_1$-$C_4$ haloalkyl, or phenyl;

$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1, 2, or 3;

p is 0, 1, 2, or 3; and q is 0, 1, or 2;

or an oxide thereof, a pharmaceutically acceptable salt thereof, a solvate thereof, or prodrug thereof.

The present invention also relates to a method of treating a disease or condition which is susceptible to treatment with a 5-$HT_3$ receptor modulator. This method involves selecting a patient with a disease or condition which is susceptible to treatment with a 5-$HT_3$ receptor modulator and administering to the patient a therapeutically effective amount of a compound of formula I or a pharmaceutically acceptable salt thereof.

Another aspect of the present invention relates to a process of preparing a compound of formula Ia:

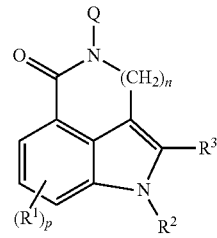

This process involves treating a first intermediate compound of formula II:

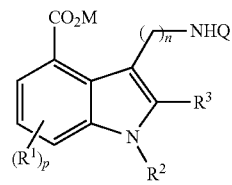

wherein M is H or a counterion, under amide bond formation conditions effective to produce the product compound.

A further aspect of the present invention relates to a process of preparing a compound of formula Ib:

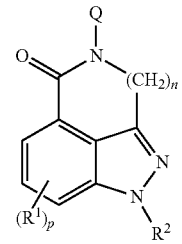

This process involves treating a first intermediate compound of formula III:

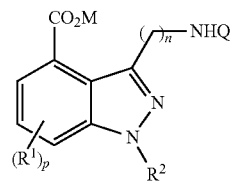

wherein M is H or a counterion, under amide bond formation conditions effective to produce the product compound.

It has now been found that compounds of formula I are 5-$HT_3$ receptor modulators. This invention provides compounds that bind to the serotonin type-3 (5-$HT_3$) receptor with high affinity. Members of this class have been demonstrated to inhibit serotonin-induced bradycardia in mice. This pharmacology is consistent with the effects of other reported 5-$HT_3$ receptor modulators, several of which have been approved to treat human disease including IBS (e.g. alosetron, ramosetron), CINV (e.g. ondansetron, palonsetron, granisetron), and PONV (palonosetron). The compounds provided by formula I are useful for the treatment of irritable bowel syndrome, nausea, emesis (vomiting), and other disorders described herein.

DETAILED DESCRIPTION OF THE INVENTION

The present invention relates to compounds of formula I:

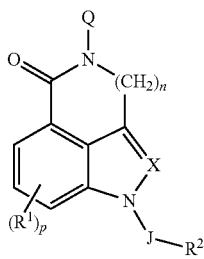

formula I wherein:
Q is a saturated, bicyclic, heterocyclic amine, wherein the saturated, bicyclic, heterocyclic amine comprises at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, —$OR^7$, and —$NR^7R^8$;
X is CH, $CR^3$, or N;
J is selected from the group consisting of a direct bond, C=O, and $SO_2$;
each $R^1$ is independently selected from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;
$R^2$ is selected from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, with the proviso that when J=$SO_2$, R is not H, and wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;
$R^3$ is selected from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;
$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;
$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;
$R^6$ is $C_1$-$C_4$ alkyl, $C_1$-$C_4$ haloalkyl, or phenyl;
$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;
n is 1, 2, or 3;
p is 0, 1, 2, or 3; and
q is 0, 1, or 2;
or an oxide thereof, a pharmaceutically acceptable salt thereof, a solvate thereof, or prodrug thereof.

As used above, and throughout the description of the invention, the following terms, unless otherwise indicated, shall be understood to have the following meanings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "aryl" means an aromatic monocyclic or multi-cyclic ring system of 6 to about 14 carbon atoms, preferably of 6 to about 10 carbon atoms, and includes arylalkyl groups. Representative aryl groups include phenyl and naphthyl.

The term "heteroaryl" means an aromatic monocyclic or multi-cyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring.

The term "cycloalkyl" means a non-aromatic mono- or multi-cyclic ring system of about 3 to about 7 carbon atoms, preferably of about 5 to about 7 carbon atoms. Exemplary monocyclic cycloalkyls include cyclopentyl, cyclohexyl, cycloheptyl, and the like.

The term "cycloalkylalkyl" means an cycloalkyl-alkyl-group in which the cycloalkyl and alkyl are as defined herein. Exemplary cycloalkylalkyl groups include cyclopropylmethyl and cyclopentylmethyl.

Arylalkyl means an alkyl residue attached to an aryl ring. Examples are benzyl, phenethyl, and the like.

The term "haloalkyl" means both branched and straight-chain alkyl substituted with one or more halogen, wherein the alkyl group is as herein described.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "halogen" means fluorine, chlorine, bromine, or iodine.

The term "compounds of the invention", and equivalent expressions, are meant to embrace compounds of general formula I as hereinbefore described, which expression includes the prodrugs, the pharmaceutically acceptable salts, the oxides, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "method of treating" means amelioration or relief from the symptoms and/or effects associated with the disorders described herein. As used herein, reference to "treatment" of a patient is intended to include prophylaxis.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. Since the compounds of formula I contain a basic nitrogen, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The abbreviations Me, Et, and Ph represent methyl, ethyl, and phenyl, respectively. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations," is incorporated herein by reference in its entirety.

The term "therapeutically effective amount" is meant to describe an amount of compound of the present invention effective in modulating 5-$HT_3$ activity and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

The term "pharmaceutical composition" means a composition comprising a compound of formula I and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs," p. 113-191 (1991); Advanced Drug Delivery Reviews, H. Bundgard, 8, p. 1-38 (1992); Journal of Pharmaceutical Sciences, 77:285 (1988); Nakeya et al, Chem. Pharm. Bull., 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The present invention relates to compounds of formula I, wherein Q is a substituted or unsubstituted bicyclic, heterocyclic amine. In accordance with the present invention, the bicyclic, heterocyclic amines are saturated and contain at least one nitrogen in the ring. They may contain additional nitrogens, as well as other heteroatoms. In the compounds of the invention, the bicyclic, heterocyclic amine includes at least 2 atoms, preferably from 2 to 4 and preferably carbon atoms, connecting the amide nitrogen to any nitrogen in the amine group Q.

In one embodiment, Q is a substituted or unsubstituted bicyclic amine. In another embodiment of the present invention, Q of formula I is a bicyclic amine of empirical formula $C_{7-10}N_{1-2}$. In a more preferred embodiment of the present invention, Q is an azabicycloheptane, azabicyclooctane, or azabicyclononane. Suitable heterocyclic amines include, but are not limited to, quinuclidine, tropane, azabicyclo[3.3.1]nonane, methyl azabicyclo[3.3.1]nonane, 9-azabicyclo[3.3.1]nonan-3-one, 3,9-dimethyl-3,9-diazabicyclo[3.3.1]nonane, 3,9-diazabicyclo[3.3.1]nonane, 3-oxa-9-azabicyclo[3.3.1]nonane, 3-thia-9-azabicyclo[3.3.1]nonane, 9-methyl-3,9-diazabicyclo[3.3.1]nonane, 3-methyl-3,9-diazabicyclo[3.3.1]nonane, 3-oxa-9-azabicyclo[3.3.1]nonane, 3-thia-9-azabicyclo[3.3.1]nonane, and azabicyclo[3.2.2]nonane.

In one embodiment of the present invention, the carbon of the bicyclic, heterocyclic amine attached to the amide nitrogen of the tricyclic core of formula I is chiral and in the (S) configuration. In another embodiment of the present invention, the carbon of the bicyclic, heterocyclic amine attached to the amide nitrogen of the tricyclic core of formula I is chiral and in the (R) configuration. Another embodiment of the present invention is a mixture of stereoisomeric compounds of formula I.

In another embodiment of the present invention, Q is a saturated, bicyclic, heterocyclic amine or methyl-substituted saturated, bicyclic, heterocyclic amine, in which the nitrogen is tertiary. In one embodiment, Q is selected from the group consisting of:

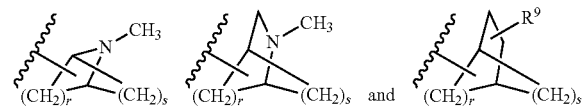

wherein r=1, 2, 3 or 4; s=0, 1, 2, 3 or 4; and $R^9$ is hydrogen or methyl. In these figures, the Q group is connected to the tricyclic core structure through any carbon ring member (i.e., not a terminal N-methyl).

Other suitable heterocyclic amines include:

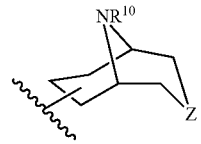

wherein $R^{10}$ is hydrogen or $C_1$-$C_3$ alkyl and Z is NH, NCH$_3$, O, S, SO, or SO$_2$.

Another preferred embodiment of the present invention is the compound of formula I, wherein $R^2$ is H, lower alkyl, phenyl, or substituted phenyl. In one preferred embodiment, $R^2$ is substituted phenyl and J is SO$_2$. In another preferred embodiment, $R^2$ is 4-fluorophenyl.

Yet another preferred embodiment of the invention is the compound of formula I, wherein at least one of $R^1$ is H, F, Cl, or Br.

Suitable aryl groups for the substituents of the present invention are selected from the group consisting of phenyl, benzyl, naphthyl, indanyl, and indenyl. Suitable heteroaryl groups for the substituents of the present invention are selected from the group consisting of pyridyl, 2-oxo-pyridin-1-yl, pyrimidinyl, pyridazinyl, pyrazinyl, 1,2,4-triazinyl, 1,3,5-triazinyl, furanyl, pyrrolyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, tetrazolyl, indolyl, isoindolyl, benzofuranyl, benzothiophenyl, indolinyl, oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-c]pyridinyl, pyrazolo[1,5-c]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, furo[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 2-oxo-2,3-dihydro-1H-benzo[d]imidazole, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridinyl.

Within these embodiments, the selection of a particular preferred substituent at any one of Q, X, J, $R^1$, $R^2$, and $R^3$ does not affect the selection of a substituent at any of the others of Q, X, J, $R^1$, $R^2$, and $R^3$. That is, preferred compounds provided herein have any of the preferred substituents at any of the positions.

In one embodiment of the present invention, the compound is selected from the group consisting of:
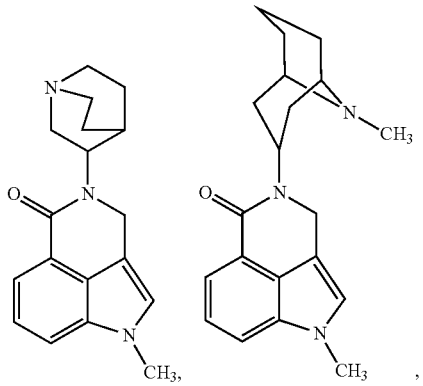
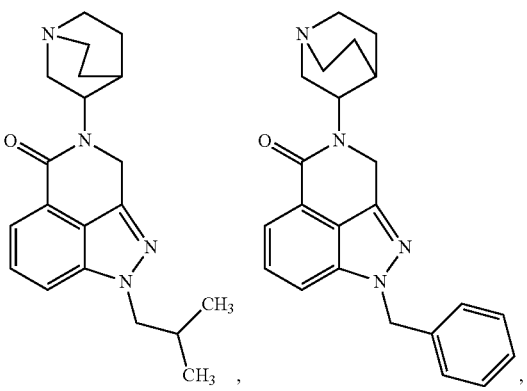
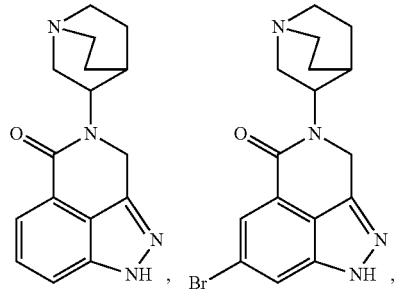
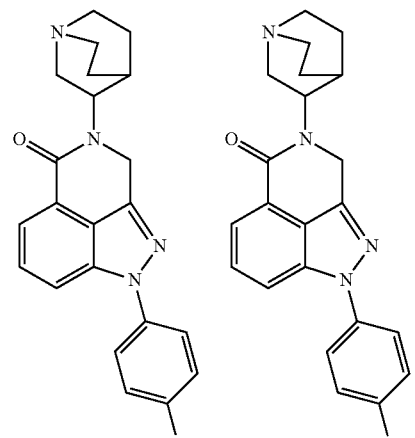
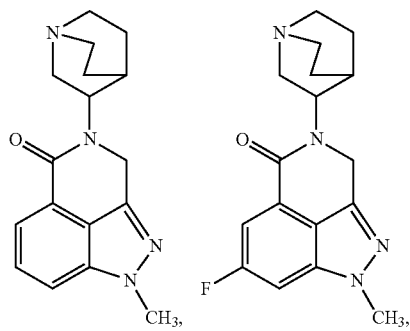
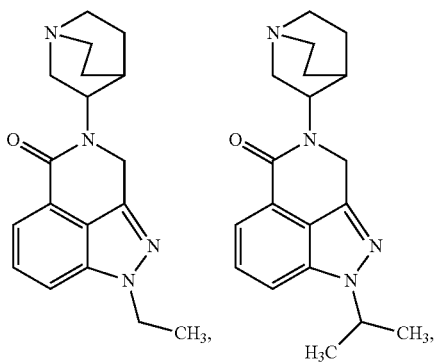
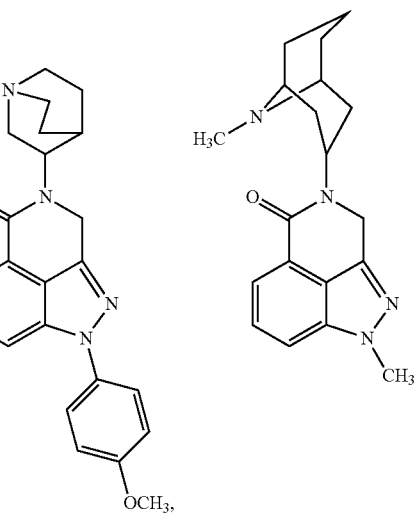

-continued

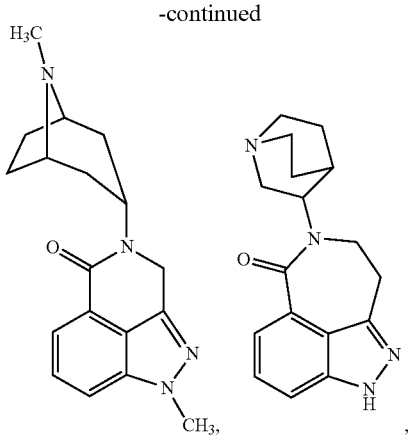

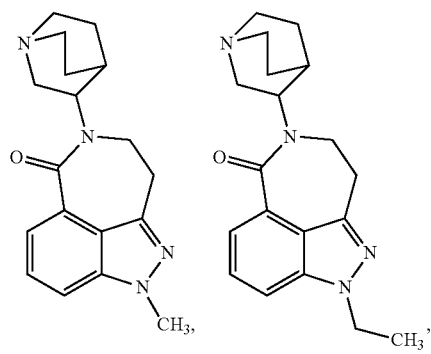

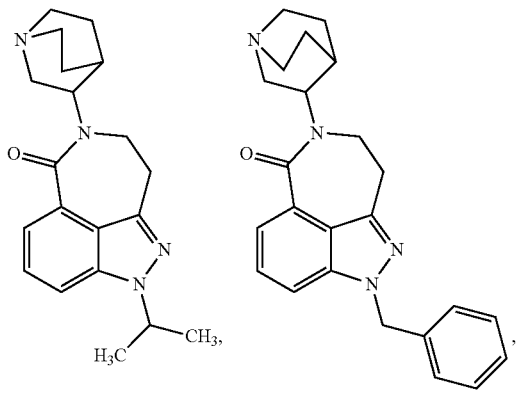

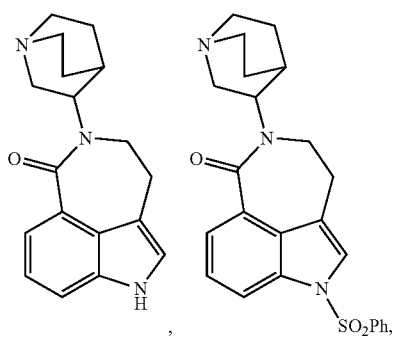

-continued

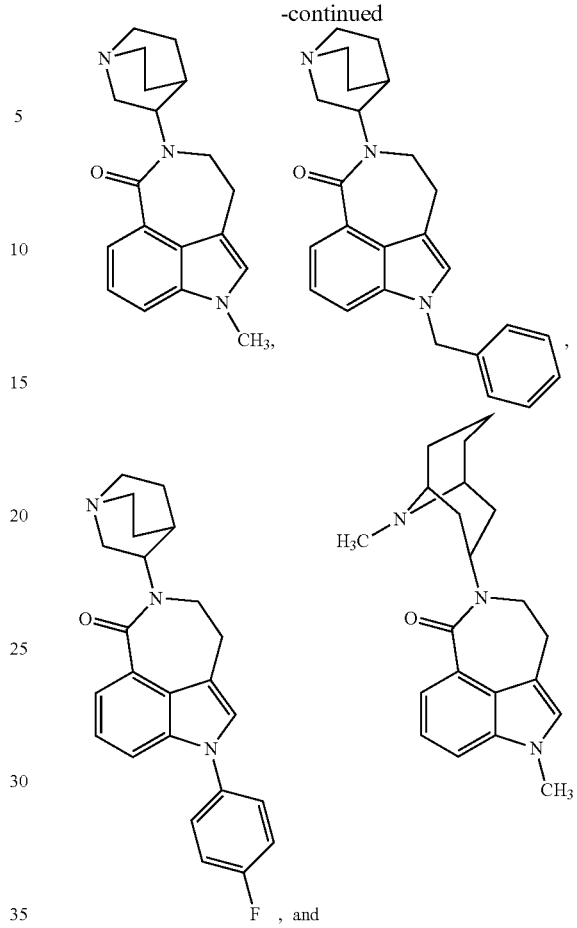

One embodiment of the present invention relates to pharmaceutically acceptable salts, or non-salt forms, of any of the compounds of formula I described herein.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of formula I, wherein one or more of the atoms, e.g., C or H, are replaced by the corresponding radioactive isotopes of that atom (e.g., C replaced by $^{14}C$ and H replaced by $^{3}H$), or a stable isotope of that atom (e.g., C replaced by $^{13}C$ or H replaced by $^{2}H$). Radioisotopes of hydrogen, carbon, phosphorous, fluorine, iodine and chlorine include $^{3}H$, $^{14}C$, $^{35}S$, $^{18}F$, $^{32}P$, $^{33}P$, $^{125}I$, and $^{36}Cl$, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the ability of a potential pharmaceutical to bind to neurotransmitter proteins. In addition, in the case of stable isotopes, such compounds may have the potential to favorably modify the biological properties, e.g., pharmacological and/or pharmacokinetic properties, of compounds of formula I. The details concerning selection of suitable sites for incorporating radioactive isotopes into the compounds are known to those skilled in the art.

Compounds of the present invention as described herein are useful as $5\text{-HT}_3$ receptor modulators. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a compound aspect, is all compounds of formula I, except those that are in the public's possession.

While it may be possible for compounds of formula I to be administered as the raw chemical, it will often be preferable to present them as part of a pharmaceutical composition. Accordingly, another aspect of the present invention is a pharmaceutical composition containing a therapeutically effective amount of a compound of formula I, or a pharmaceutically acceptable salt or solvate thereof, and a pharmaceutically acceptable carrier. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

In one embodiment of the present invention, the pharmaceutical composition further comprises one or more other therapeutic ingredients, e.g., other compounds effective in the treatment of IBS, CINV or PONV, that are known to persons of skill in the art. Such other therapeutic agents are described below.

Another aspect of the present invention relates to a method of treating a disease or condition which is susceptible to treatment with a $5\text{-HT}_3$ receptor modulator. This method involves selecting a patient with a disease or condition which is susceptible to treatment with a $5\text{-HT}_3$ receptor modulator and administering to the patient a therapeutically effective amount of a compound of formula I or a pharmaceutically acceptable salt thereof.

Diseases or conditions which are susceptible to treatment with a $5\text{-HT}_3$ receptor modulator in accordance with the present invention include, but are not limited to, general anxiety disorders, social phobias, vertigo, obsessive-compulsive disorders, panic disorders, post-traumatic stress disorders, bulimia nervosa, drug withdrawal effects, alcohol dependency, pain (including visceral pain), sleep related central apneas, chronic fatigue syndrome, Parkinson's Disease Psychosis, schizophrenia, cognitive decline and defects in schizophrenia, Parkinson's Disease, Huntington's Chorea, presenile dementias, Alzheimer's Disease, psychological disorders, obesity, substance abuse disorders, dementia associated with neurodegenerative disease, cognition deficits, fibromyalgia syndrome (see US. Patent Application Publication No 2004/0204467, which is hereby incorporated by reference in its entirety), rosacea (see PCT Publication No. WO 2007/138233, which is hereby incorporated by reference in its entirety), cardiovascular disorders mediated by serotonin, chemotherapy induced nausea and vomiting (CINV), post-operative induced nausea and vomiting (PONV), radiation induced nausea and vomiting (RINV), gastrointestinal disorders (e.g. of the esophagus, stomach and both large and small intestines), including irritable bowel syndrome (IBS) and gastroesophageal reflux disease (GERD) (see European Patent No. EP0430190, U.S. Pat. No. 6,967,207, and U.S. Pat. No. 5,352,685, which are hereby incorporated by reference in their entirety), bronchial asthma, pruritus, migraine (see Costall et al., *Current Drug Targets—CNS & Neurological Disorders*, 3:27-37 (2004) and Israili, *Current Med. Chem.— CNS Agents*, 1:171-199 (2001), which are hereby incorporated by reference in their entirety), and epilepsy (see PCT Publication No. WO 2007/010275, which is hereby incorporated by reference in its entirety).

As described above, the compounds of the present invention are useful as $5\text{-HT}_3$ modulators. A $5\text{-HT}_3$ receptor modulator is an agent which can either inhibit (e.g., an antagonist) or partially activate (e.g., a partial agonist) the $5\text{-HT}_3$ receptor. A $5\text{-HT}_3$ receptor modulator which is a partial agonist can bind the $5\text{-HT}_3$ receptor but only results in partial efficacy relative to a full receptor agonist. Modulators which are partial agonists may be considered ligands which display both agonistic and antagonistic effects depending upon the level of serotonin (endogenous $5\text{-HT}_3$ agonist). For example, when both full agonist (e.g. serotonin) and partial agonist are present, the partial agonist acts as a competitive antagonist, competing with the full agonist for receptor occupancy and producing a net decrease in the receptor activation observed with the full agonist alone (Williams et al., *Principles and Practice of Pharmacology for Anaesthetists*, $4^{th}$ Ed., Calvey et al., eds., Blackwell Science Asia Pty Ltd., Carlton South, Vic (2001), which is hereby incorporated by reference in its entirety). Clinically, partial agonists can activate receptors to give a desired submaximal response when inadequate amounts of the endogenous ligand are present or they can reduce the overstimulation of receptors when excess amounts of endogenous ligand are present (Zhu, *Biomed. Pharmacother.* 59(3):76-89 (2005), which is hereby incorporated by reference in its entirety).

Thus, in one embodiment of the present invention, the compound according to claim 1 or pharmaceutically acceptable salt thereof is a $5\text{-HT}_3$ receptor antagonist.

In another embodiment of the present invention, the compound according to claim 1 or pharmaceutically acceptable salt thereof is a $5\text{-HT}_3$ receptor partial agonist, which may result in a net increase or a net decrease in activation of the $5\text{-HT}_3$ receptor in the patient.

In another embodiment of the present invention, the above method further involves administering a therapeutically effective amount of one or more schizophrenia or Parkinson's Disease adjuncts. Suitable schizophrenia adjuncts include, but are not limited to, valproate and levomepromazine. Suitable Parkinson's Disease adjuncts include, but are not limited to, transdermal rotigotine, rotigotine and/or rasagiline as a levodopa adjuncts, levodopa, carbidopa, dopamine agonists (bromocriptine, pramipexole, or ropinirole), COMT inhibitors (entacapone or tolcapone), MAO-B inhibitors (rasagiline or selegiline), amantadine, anticholinergic agents (benztropine or trihexyphenidyl), and salfinamide. The compositions may additionally comprise alprazolam, haloperidol, chlorpromazine, risperidone, paliperidone, olanzapine, ziprasidone, quetiapine, clozapine, lithium carbonate, diazepam, carbamazepine, selective serotonin re-uptake inhibitors (SSRI's) (ZOLOFT® or CELEXA®) or tricyclic antidepressants, such as PAMELOR®.

A further aspect of the present invention relates to a method of treating irritable bowel syndrome (IBS). This method involves selecting a patient with IBS and administering to the patient a therapeutically effective amount of a compound of formula I or a pharmaceutically acceptable salt thereof.

In another embodiment of the present invention, the above method further involves administering a therapeutically effective amount of other serotonin 5-HT$_3$ receptor modulators and/or serotonin 5-HT$_4$ receptor modulators, some of which are indicated below. Suitable other serotonin 5-HT$_3$ receptor modulators and/or serotonin 5-HT$_4$ receptor modulators include, but are not limited to, Alosetron (LOTRONEX®), renzapride, cilansetron, Tegaserod (ZELNORM®), Prucalopride, ondansetron; somatostatin analogs such as Octreotide; muscarinic receptor antagonists such as Darifenacin, and Zamifenacin; laxatives such as methylcellulose (CITRUCEL®), Psyllium (METAMUCIL®, FIBERALL®, REGULOID®, KONSYL®), malt soup extract, polyacrylic resins (e.g., hydrophilic forms such as polycarbophil and calcium polycarbophil), plantago seeds, dioctyl calcium sulfosuccinate, dioctyl potassium sulfosuccinate, dioctyl sodium sulfosuccinate, mineral oil, magnesium citrate, magnesium hydroxide, magnesium sulfate, dibasic sodium phosphate, monobasic sodium phosphate, sodium biphosphate, glycerin, anthraquinones or anthracene laxatives (such as aloe, cascara sagrada, danthron, senna, aloin, casanthranol, frangula, and rhubarb), diphenylmethanes (such as bisacodyl and phenolphthalein), and castor oil and the like; antispasmodics, such as the anticholinergic agents dicyclomine HCl (BENTYL®), hyoscyamine sulfate (LEVSIN®), and the like; antidepressants such as imipramine (TOFRANIL®), amitriptylin (ELAVIL®); antidiarrheal agents such as diphenoxylate HCl+atropine sulfate (LOMOTIL®), loperamide (IMODIUM®), natural or synthetic opiates (such as difenoxin, diphenoxylate, pargoric, opium tincture, and loperamide), anticholinergics (such as belladonna alkoloids-atropine hyoscyamine, and hyosine), acetyltannic acid, albumin tannate, alkofanone, aluminum salicylates, catechin, lidamidine, mebiquine, trillium, and uzarin, and the like; prokinetic agents, peripheral opiate narcotic antagonists such as fedotozine, trimebutine, and the like. Suitable prokinetic agents include, but are not limited to, cisapride monohydrate (PROPULSID®), metoclopromide, domperidone, and the like.

Another aspect of the present invention relates to a method of treating emesis. This method involves selecting a patient with emesis and administering to the patient a therapeutically effective amount of a compound of formula I or a pharmaceutically acceptable salt thereof.

In another embodiment of the present invention, the above method further involves administering a therapeutically effective amount of one or more other anti-emetic compounds. Suitable anti-emetic compounds include, but are not limited to, alosetron, alprazolam, aprepitant, dexamethasone, dimenhydrinate, diphenhydramine, dolasetron, tetrahydrocannabinol, nabilone, dronabinol, droperidol, granisetron, haloperidol, lorazepam, metoclopramide, midazolam, olanzapine, ondansetron, palonosetron, proclorperazine, promethazine, and tropisetron.

Yet another aspect of the present invention relates to a method of treating CNS diseases or conditions. This method involves selecting a patient with a CNS disease or condition and administering to the patient an effective amount of a compound of formula I or a pharmaceutically acceptable salt thereof. Suitable CNS diseases or conditions include, but are not limited to, schizophrenia and Parkinson's disease. Beneficial effects of 5-HT$_3$ modulators have been reported in clinical studies of Parkinson's disease (Zoldan J et al., *Advances in Neurology*, 69:541-544 (1996), which is hereby incorporated by reference in its entirety) and schizophrenia (Zhang-Jin et al., *Schizophrenia Research*, 88: 102-110 (2006); Alder et al., *Am. J. Psychiatry*, 162:386-388 (2005), which are hereby incorporated by reference in their entirety). Brain responses in humans have been altered upon treatment with alosetron in IBS patients (Mayer et al., *Aliment Pharmacol. Ther.*, 16:1357-1366 (2002), which is hereby incorporated by reference in its entirety). A 5-HT$_3$ modulator may be used as an adjunct or in combination with another medication.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Another aspect of the present invention relates to a process of preparing a compound of formula Ia:

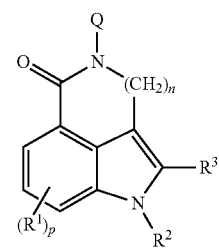

This process involves treating a first intermediate compound of formula II:

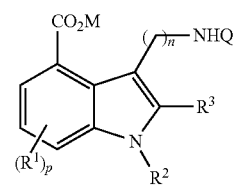

wherein M is H or a counterion, under amide bond formation conditions effective to produce the product compound. Q, R$^1$, R$^2$, and R$^3$ are as defined above A further aspect of the present invention relates to a process of preparing a compound of formula Ib:

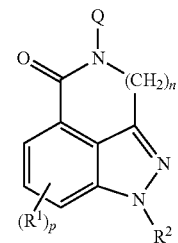

This process involves treating a first intermediate compound of formula III:

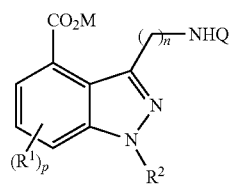

wherein M is H or a counterion, under amide bond formation conditions effective to produce the product compound. Q, $R^1$, and $R^2$ are as defined above Suitable counterions include, but are not limited to, $Li^+$ and $Na^+$.

The methods of synthesis of the present invention involve standard amide bond formation conditions that are familiar to one skilled in the art of organic synthesis. This typically involves activation of the carboxyl component followed by reaction of the amine. Suitable activating groups include, but are not limited to, acyl halides, acyl azides, acylimidazoles, anhydrides, and esters as described by Montalbetti et al., *Tetrahedron*, 61:10827 (2005), which is hereby incorporated by reference in its entirety. Preferred activating reagents include thionyl chloride ($SOCl_2$), oxalyl chloride ($COCl)_2$, phosphorus oxychloride ($POCl_3$), carbonyl diimidazole (CDI), dicyclohexyl carbodiimide (DCC), 1-ethyl-3-(3-dimethylaminopropyl) carbodiimide) (EDCI), 1-hydroxybenzotriazole (HOBt), O-(1H-benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and 1-propanephosphonic acid cyclic anhydride (T3P).

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula I including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice and as described above.

The novel 5-$HT_3$ modulators of formula I of this invention can be prepared by the methods illustrated in the general reaction schemes as, for example, described below, or by modifications thereof, using readily available starting materials, reagents, and conventional synthesis procedures. In these reactions, it is also possible to make use of variants that are known in the art but are not mentioned here. Although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

General Procedures for Constructing a Compound of Formula Ia (A4 Tricyclic Core)

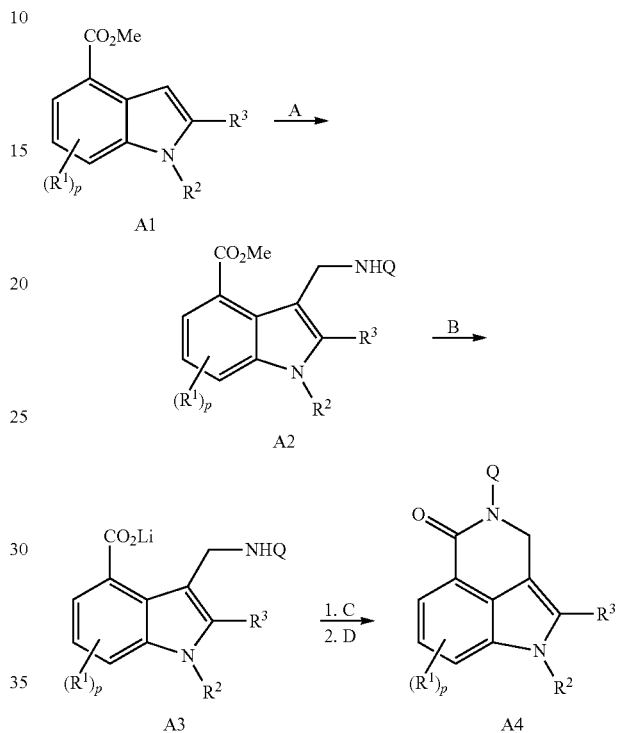

$R^1$, $R^2$, and $R^3$ are consistent with formula I
$QNH_2$ = amine
Conditions:
A) $QNH_2$, $CH_2O$, HOAc;
B) hydroxide base;
C) HBTU, DMF;
D) HCl, MeOH or $CH_2Cl_2$ Compound A1 where $R^1$=OH and $OCH_3$ can be achieved by a method reported by Krutosikova et al., *Collect. Czech. Chem. Commun.*, 57:1487 (1992), which is hereby incorporated by reference in its entirety. Conversion of A1 where $R^1$=OH to $R^1$=Cl can be achieved by a method reported in Bay et. al., *J. Org. Chem.*, 55:3415 (1990), which is hereby incorporated by reference in its entirety. Conversion of A1 where $R^1$=OH to $R^1$=Br can be achieved by a method reported by Riche et. al., *Justus Liebigs Ann. Chem.*, 121: 359 (1862), which is hereby incorporated by reference in its entirety. Conversion of A1 where $R^1$=OH to $R^1$=F can be achieved by a method reported by Ashton et. al., *J. Fluorine. Chem.*, 27:263 (1985), which is hereby incorporated by reference in its entirety. Conversion of A1 where $R^1$=OH to $R^1$=OTf (phenolic triflate ester) can be readily achieved (McCort et al., *Tetrahedron Lett.*, 40:6211 (1999), which is hereby incorporated by reference in its entirety). This material, or where $R^1$=bromo, iodo or chloro, can be used as a coupling reagent for transition metal-catalyzed cross coupling reactions (e.g. Suzuki, Stille, Sonogashira) to provide compounds A1 where $R^1$=alkyl, aryl, and heteroaryl.

General Procedure (GP-A) for the Mannich Coupling of the Indole Core:

A mixture of indole A1 (1 eq), and appropriate amine (1.1 eq) and 37% aqueous formaldehyde (1.1 eq) in glacial acetic acid was stirred at room temperature for 18 hours. The mixture was poured onto ice-water and made alkaline with 1N sodium hydroxide. The resulting precipitate was filtered and the mother liquor was extracted with dichloromethane. The combined organics were washed with brine, dried ($Na_2SO_4$), filtered, and concentrated under reduced pressure to afford the desired product indole 3-aminomethyl adduct. The product was subsequently used without further purification. Product structure was confirmed by $^1$H NMR or by mass analysis.

General Procedure (GP-B) for the Hydrolysis of the Methyl Ester (Lithium Carboxylate Salt):

A mixture of the methyl ester A2 and lithium hydroxide monohydrate (3 eq) in tetrahydrofuran/water (1:1) was stirred at reflux until the reaction was complete by LC-MS. The solvent was removed under reduced pressure and the crude lithium salt A3 was dried under high vacuum and subsequently used without further purification. The product structure was confirmed by $^1$H NMR or by mass analysis.

General Procedure (GP-C) for Cyclization:

A mixture of the lithium carboxylate salt A3 (1 eq) and 2-(1H-benzotriazole-1-yl)-1,1,3,3-tetramethyluronium hexafluorophosphate (HBTU) (1.5 eq) in DMF was stirred at 50° C. until the reaction was complete by LC-MS. The mixture was concentrated under reduced pressure and the crude material was purified by silica gel chromatography (typical eluents dichloromethane and dichloromethane/methanol/concentrated ammonium hydroxide) to afford the desired carboxamide A4. The product structure was verified by $^1$H NMR or by mass analysis.

General Procedure (GP-D) for Conversion to the HCl Salt:

To an ice-cold solution of the carboxamide A4 (1 eq) in dichloromethane was added hydrogen chloride (1-3 eq) in methanol. The mixture was concentrated under reduced pressure. The solid was lyophilized from water and acetonitrile to afford the desired A4 hydrochloride salt. The product was verified by mass analysis and $^1$H NMR.

General Procedures for Constructing a Compound of Formula Ib (B5 Tricyclic Core)

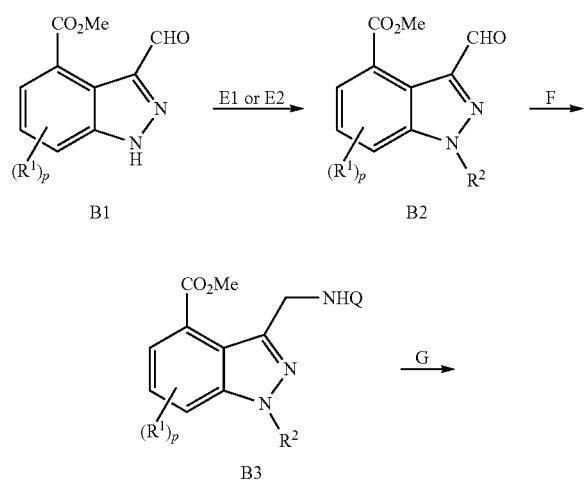

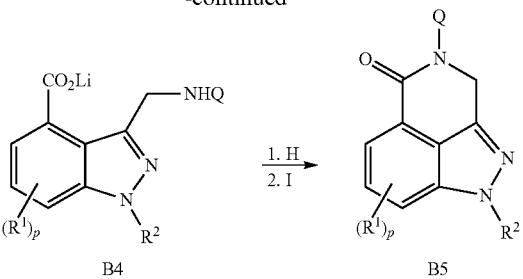

$R^1$ and $R^2$ are consistent with Formula I
$QNH_2$ = amine
Conditions:
E1) $Cs_2CO_3$, $R^2X$, DMSO;
E2) $ArB(OH)_2$, $Cu(OAc)_2$, $Et_3N$, $CH_2Cl_2$;
F) $NH_2Q$, $NaBH(OAc)_3$, 1% HOAc in $CH_2Cl_2$;
G) hydroxide base;
H) HBTU, DMF;
I) HCl, MeOH or $CH_2Cl_2$ Compound B1, where $R^1$=Br (6-bromo-3-formyl-4-indazole carboxylic acid methyl ester), is commercially available from SINOVA, BETHESDA, MD (catalog number SL-00263). Compound B1, where $R^1$=Cl (6-chloro-3-formyl-4-indazole carboxylic acid methyl ester), is also commercially available from SINOVA, BETHESDA, MD (catalog number SL-01561). Compound B1, where $R^1$=F (6-fluoro-3-formyl-4-indazole carboxylic acid methyl ester), is also commercially available from SINOVA, BETHESDA, MD (catalog number SL-01547).

General Procedure (GP-E1) for the Alkylation of the Indazole 3-Carboxaldehyde Core:

A mixture of indazole B1 (1 eq), and appropriate alkyl halide (2 eq) and cesium carbonate (4 eq) in dimethylsulfoxide was stirred at room temperature until the reaction was complete by LC-MS (8 to 10 hours). The mixture was diluted with water and extracted with ethyl acetate. The combined organics were washed with water and brine, dried ($Na_2SO_4$), filtered, and concentrated under reduced pressure. The crude material was purified by silica gel chromatography (typical eluents hexanes and ethyl acetate or dichloromethane and methanol) to afford the desired alkylated indazole 3-carboxaldehyde B2. The product structure was verified by $^1$H NMR or by mass analysis.

General Procedure (GP-E2) for the Arylation of the Indazole 3-Carboxaldehyde Core:

A mixture of indazole B1 (1 eq), and appropriate aryl or heteroaryl boronic acid (2 eq), cupric acetate (1.5 eq), and triethylamine (2 eq) in dichloromethane was stirred at room temperature until the reaction was complete by LC-MS (16 hours). The mixture was directly adsorbed onto silica gel and chromatographed. The crude material was purified by silica gel chromatography (typical eluents hexanes and ethyl acetate) to afford the desired arylated indazole 3-carboxaldehyde B2. The product structure was verified by $^1$H NMR or by mass analysis.

General Procedure (GP-F) for the Reductive Amination of the Indazole 3-Carboxaldehyde Core:

A mixture of indazole 3-carboxaldehyde B2 (1 eq) and appropriate amine (1.2 to 1.5 eq) was stirred in 1% glacial acetic acid and dichloromethane at room temperature for 4 to 16 hours. To this was added sodium triacetoxyborohydride (3 to 4 eq) and the mixture stirred for an additional 2 to 16 hours. The mixture was directly adsorbed onto silica gel and chromatographed (typical eluents dichloromethane and dichloromethane/methanol/concentrated ammonium hydroxide) to afford the desired indazole 3-aminomethyl adduct B3. The product structure was verified by ¹H NMR or by mass analysis.

General Procedure (GP-G) for the Hydrolysis of the Methyl Ester (Lithium Carboxylate Salt):

A mixture of the methyl ester B3 and lithium hydroxide monohydrate (3 eq) in tetrahydrofuran/water (1:1) was stirred at reflux until the reaction was complete by LC-MS. The solvent was removed under reduced pressure and the crude lithium salt B4 was dried under high vacuum and subsequently used without further purification. The product structure was confirmed by ¹H NMR or by mass analysis.

General Procedure (GP-H) for Cyclization:

A mixture of the lithium carboxylate salt B4 (1 eq) and HBTU (1.5 eq) in DMF was stirred at room temperature until the reaction was complete by LC-MS. The mixture was concentrated under reduced pressure and the crude material was purified by either or both silica gel chromatography (typical eluents dichloromethane and dichloromethane/methanol/concentrated ammonium hydroxide) and solid phase extraction using cation exchange SCX resin (typical eluents methanol and 7 N ammonia solution in methanol) to afford the desired carboxamide B5. The product structure was verified by ¹H NMR or by mass analysis.

General Procedure (GP-I) for Conversion to the HCl Salt:

To an ice-cold solution of the carboxamide B5 (1 eq) in dichloromethane was added hydrogen chloride (1-4 eq) in methanol. The mixture was concentrated under reduced pressure and the residue was recrystallized from hot absolute ethanol. The solid was lyophilized from water and acetonitrile to afford the desired B5 hydrochloride salt. The product was verified by mass analysis and ¹H NMR.

General Procedures for Constructing a Compound of Formula Ib (C4 Tricyclic Core)

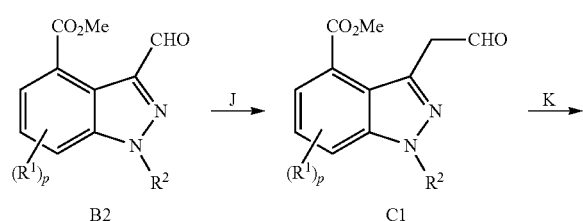

B2    C1

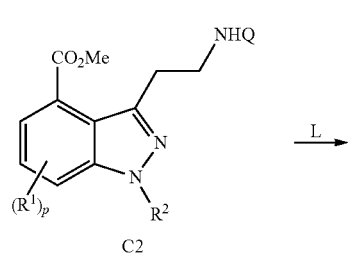

C2

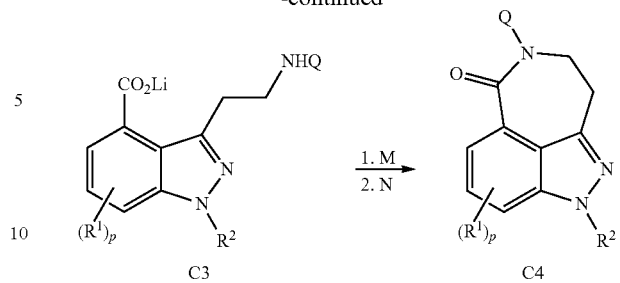

C3    C4

R¹ and R² are consistent with Formula I
QNH₂ = amine
Conditions:
J) i. PPh₃PCH₂OCH₃Cl, KHMDS, THF; ii. 4N HCl;
K) NH₂Q, NaBH(OAc)₃, 1% HOAc in CH₂Cl₂;
L) hydroxide base;
M) HBTU, DMF;
N) HCl, MeOH or CH₂Cl₂

General Procedure (GP-J) for the Aldehyde Homologation of the Indazole 3-Carboxaldehyde Core:

To a −40° C. cooled suspension of (methoxymethyl)triphenylphosphonium chloride (3 eq) in tetrahydrofuran was carefully added a solution of potassium bis(trimethylsilyl) amide (0.5M in toluene, 3 eq). The resulting dark red-orange mixture was stirred at −40° C. for 30 minutes and then warmed to 0° C. To this was added a solution of B2 (1 eq) in tetrahydrofuran and the mixture stirred for 16 hours at room temperature. A 1:1 mixture of tetrahydrofuran and methanol was added, followed by 4N hydrochloric acid (4 eq) and the biphasic mixture was heated at 60° C. for 4 hours. The mixture was cooled to room temperature and diluted with ethyl acetate. The organic layer was washed with water, saturated aqueous sodium bicarbonate, and brine, dried (Na₂SO₄), filtered, and concentrated under reduced pressure. The crude material was purified by silica gel chromatography (typical eluents hexanes and ethyl acetate or dichloromethane and methanol) to afford the desired homologated indazole 3-carboxaldehydemethyl adduct C1. The product structure was verified by ¹H NMR or by mass analysis.

General Procedure (GP-K) for the Reductive Amination of the Indazole 3-Carboxaldehyde Core:

A mixture of indazole 3-carboxaldehyde C1 (1 eq) and appropriate amine (1.2 to 1.5 eq) in 1% glacial acetic acid in dichloromethane was stirred at room temperature for 4 to 16 hours. To this was added sodium triacetoxyborohydride (3 to 4 eq) and the mixture stirred for an additional 2 to 16 hours. The mixture was directly adsorbed onto silica gel and chromatographed (typical eluents dichloromethane and dichloromethane/methanol/concentrated ammonium hydroxide) and then subjected to solid phase extraction using cation exchange SCX resin (typical eluents methanol and 7 N ammonia solution in methanol) to afford the desired indazole 3-aminoethyl adduct C2. The product structure was verified by ¹H NMR or by mass analysis.

General Procedure (GP-L) for the Hydrolysis of the Methyl Ester (Lithium Carboxylate Salt):

A mixture of the methyl ester C2 and lithium hydroxide monohydrate (3 eq) in tetrahydrofuran/water (1:1) was stirred at reflux until the reaction was complete by LC-MS. The solvent was removed under reduced pressure and the crude lithium salt C3 was dried under high vacuum and subsequently used without further purification. The product structure was confirmed by ¹H NMR or by mass analysis.

General Procedure (GP-M) for Cyclization:

A mixture of the lithium carboxylate salt C3 (1 eq) and HBTU (1.5 eq) in DMF was stirred at room temperature until the reaction was complete by LC-MS. The mixture was concentrated under reduced pressure and the crude material was purified by either or both silica gel chromatography (typical eluents dichloromethane and dichloromethane/methanol/concentrated ammonium hydroxide) and solid phase extraction using cation exchange SCX resin (typical eluents methanol and 7 N ammonia solution in methanol) to afford the desired carboxamide C4. The product structure was verified by $^1$H NMR or by mass analysis.

General Procedure (GP-N) for Conversion to the HCl Salt:

To an ice-cold solution of the carboxamide C4 (1 eq) in dichloromethane was added hydrogen chloride (1-4 eq) in methanol. The mixture was concentrated under reduced pressure and the residue was recrystallized from hot absolute ethanol. The solid was lyophilized from water and acetonitrile to afford the desired C4 hydrochloride salt. The product was verified by mass analysis and $^1$H NMR.

General Procedures for Constructing a Compound of Formula Ia (D5 Tricyclic Core)

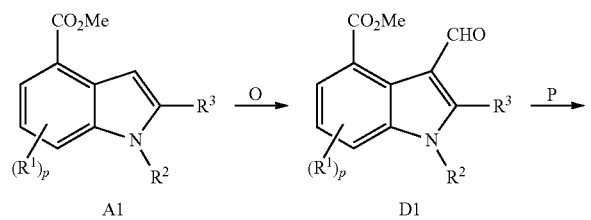

A1     D1

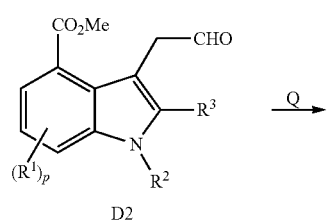

D2

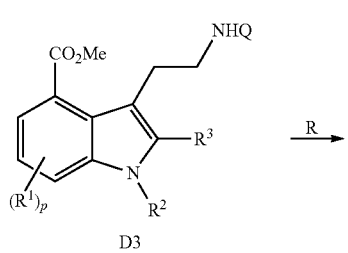

D3

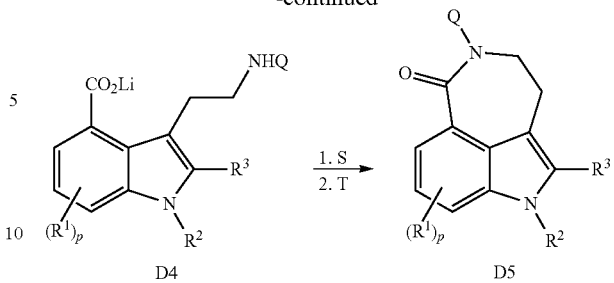

D4     D5

$R^1$, $R^2$, and $R^3$ are consistent with formula I
$QNH_2$ = amine
Conditions:
O) $POCl_3$, DMF;
P) i. $PPh_3PCH_2OCH_3Cl$, KHMDS, THF; ii. 4N HCl in dioxane;
Q) $NH_2Q$, $NaBH(OAc)_3$, 1% HOAc in $CH_2Cl_2$;
R) hydroxide base;
S) HBTU, DMF;
T) HCl, MeOH or $CH_2Cl_2$ General Procedure (GP-O) for the Vilsmeier Formylation of the Indole Core:

Phosphorus oxychloride (1.2 eq) was added slowly to ice-cold DMF and the resulting mixture was stirred at 0° C. for 30 minutes. To this was added a solution of indole A1 (1 eq) in DMF and the mixture continued to stir for 6 hours. The reaction mixture was poured into an ice/water mixture and pH was adjusted to 7 by adding 1N NaOH. The compound was extracted with ethyl acetate (4×) and the combined organic layers were washed with brine, dried ($Na_2SO_4$), filtered, and concentrated under reduced pressure. The crude material was purified by silica gel chromatography (typical eluents hexanes and ethyl acetate) to afford the desired indole 3-carboxaldehyde D1. The product structure was confirmed by $^1$H NMR and mass analysis.

General Procedure (GP-P) for the Aldehyde Homologation of the Indole 3-Carboxaldehyde Core:

To a −40° C. cooled suspension of (methoxymethyl)triphenylphosphonium chloride (3 eq) in tetrahydrofuran was carefully added a solution of KHMDS (0.5M in toluene, 3 eq). The resulting dark red-orange mixture was stirred at −40° C. for 30 minutes and then warmed to 0° C. To this was added a solution of D1 (1 eq) in tetrahydrofuran and the mixture stirred for 16 hours at room temperature. A 1:1 mixture of tetrahydrofuran and methanol was added, followed by 4N hydrochloric acid (4 eq) and the biphasic mixture was heated at 60° C. for 4 hours. The mixture was cooled to room temperature and diluted with ethyl acetate. The organic layer was washed with water, saturated aqueous sodium bicarbonate, and brine, dried ($Na_2SO_4$), filtered, and concentrated under reduced pressure. The crude material was purified by silica gel chromatography (typical eluents hexanes and ethyl acetate or dichloromethane and methanol) to afford the desired homologated indole 3-carboxaldehydemethyl adduct D2. The product structure was verified by $^1$H NMR and mass analysis.

General Procedure (GP-Q) for the Reductive Amination of the Indole 3-Carboxaldehyde Core:

A mixture of indole 3-carboxaldehyde D2 (1 eq) and appropriate amine (1.2 to 1.5 eq) in 1% glacial acetic acid and dichloromethane was stirred at room temperature for 4 to 16 hours. To this was added sodium triacetoxyborohydride (3 to 4 eq) and the mixture stirred for an additional 2 to 16 hours. The solvent was removed under reduced pressure and the crude material was purified by silica gel chromatography (typical eluents dichloromethane and dichloromethane/ methanol/concentrated ammonium hydroxide) to afford the desired indole 3-aminoethyl adduct D3. The product structure was verified by $^1$H NMR and mass analysis.

General Procedure (GP-R) for the Hydrolysis of the Methyl Ester (Lithium Carboxylate Salt):

A mixture of the methyl ester D3 and lithium hydroxide monohydrate (3 eq) in tetrahydrofuran/water (1:1) was stirred at reflux until the reaction was complete by LC-MS. The solvent was removed under reduced pressure and the crude lithium salt D4 was dried under high vacuum and subsequently used without further purification. The product structure was confirmed by $^1$H NMR or by mass analysis.

General Procedure (GP-S) for Cyclization:

A mixture of the lithium carboxylate salt D4 (1 eq) and HBTU (3 eq) in DMF was stirred at room temperature until the reaction was complete by LC-MS. The mixture was concentrated under reduced pressure and the crude material was purified by either or both silica gel chromatography (typical eluents dichloromethane and dichloromethane/methanol/concentrated ammonium hydroxide) and solid phase extraction using cation exchange SCX resin (typical eluents methanol and 7 N ammonia solution in methanol) to afford the desired carboxamide D5. The product structure was verified by $^1$H NMR and mass analysis.

General Procedure (GP-T) for Conversion to the HCl Salt:

To an ice-cold solution of the carboxamide D5 (1 eq) in dichloromethane was added hydrogen chloride (1-4 eq) in methanol. The mixture was concentrated under reduced pressure and the residue was recrystallized from diethyl ether. The solid was lyophilized from water and acetonitrile to afford the desired D5 hydrochloride salt. The product was verified by $^1$H NMR and mass analysis.

General Procedure (GP-U) for the Debenzylation of the D5 Tricyclic Core

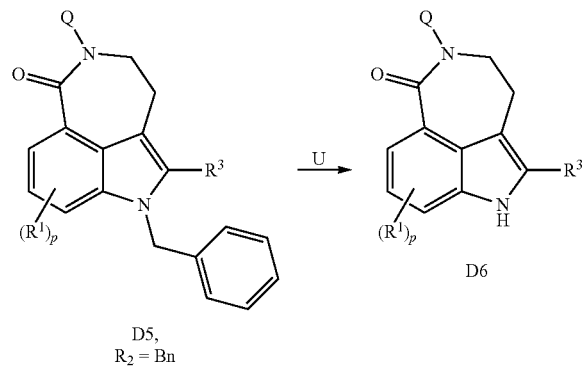

D5, R$_2$ = Bn

D6

R$_1$ and R$^3$ are consistent with Formula I
QNH$_2$ = amine
Conditions: KOtBu (1.0M solution in THF), O$_2$, DMSO, rt Oxygen gas was bubbled into a solution of carboxamide D5 (1 eq) in DMF and potassium tert-butoxide (1.0 M solution in THF, 5 eq) at room temperature. Nitrogen gas was then bubbled through the mixture and the reaction was quenched with 4 N HCl in dioxane (pH 5). The reaction was diluted with diethyl ether to afford an off-white solid which was purified by silica gel chromatography (typical eluents dichloromethane and dichloromethane/methanol/concentrated ammonium hydroxide) to afford the desired carboxamide D6. The product structure was verified by $^1$H NMR and mass analysis.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining one or more active ingredients useful in treating the disease. A kit may provide (alone or in combination with a pharmaceutically acceptable diluent or carrier) the compounds of formula I and an additional active ingredient (alone or in combination with diluent or carrier), as described above.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The formulations of compounds of formula I include those suitable for oral, parenteral (including subcutaneous, intradermal, intramuscular, intraperitoneal, intravenous, and intraarticular), rectal, colonic, and topical (including dermal, buccal, nasal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.001 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 0.01 to 0.1 mg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 0.01 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

For additional information about pharmaceutical compositions and their formulation, see, for example, Remington, *The Science and Practice of Pharmacy*, 20$^{th}$ Edition (2000), which is hereby incorporated by reference in its entirety.

The compounds of formula 1 can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of formula I can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. PCT Publication No. WO 97/11682, which is hereby incorporated by reference in its entirety) via a liposomal formulation (see, e.g., European Patent EP 736299 and PCT Publication Nos. WO 99/59550 and WO 97/13500, which are hereby incorporated by reference in their entirety), via formulations described in PCT Publication No. WO 03/094886, which is hereby incorporated by reference in its entirety, or in some other form. The compounds of formula I can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al., *Nature Reviews Drug Discovery* 3:115 (2004), which is hereby incorporated by reference in its entirety)).

Compounds of formula I can be incorporated into a liposome to improve half-life. Compounds of formula I can also be conjugated to polyethylene glycol (PEG) chains. Methods for pegylation and additional formulations containing PEG-conjugates (i.e. PEG-based hydrogels, PEG modified liposomes) can be found in Harris et al., *Nature Reviews Drug Discovery*, 2:214-221 (2003) and the references therein, which are hereby incorporated by reference in their entirety. Compounds of formula I can also be administered via a nanocochleate or cochleate delivery vehicle (BioDelivery Sciences International, Raleigh, N.C.). Compounds of formula I can also be delivered using nanoemulsion formulations.

EXAMPLES

Unless otherwise noted, reagents and solvents were used as received from commercial suppliers. Proton nuclear magnetic resonance (NMR) spectra were obtained on Bruker spectrometers at 300, 400, or 500 MHz. Spectra are given in ppm (δ) and coupling constants, J, are reported in Hertz. Tetramethylsilane (TMS) was used as an internal standard. Mass spectra were collected using either a Finnigan LCQ Duo LC-MS ion trap electrospray ionization (ESI) or a mass Varian 1200 L single quadrapole mass spectrometer (ESI). High performance liquid chromatograph (HPLC) analyses were obtained using a Luna C18(2) column (250×4.6 mm, Phenomenex, Torrance, Calif.) with UV detection at 254 nm using a standard solvent gradient program (Method A or Method B).

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method B:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |
| 31.0 | 1.0 | 90.0 | 10.0 |

A = Water with 0.05% Trifluoroacetic Acid
B = Acetonitrile with 0.05% Trifluoroacetic Acid Example 1

Preparation of Methyl 1-methyl-1H-indole-4-carboxylate (A1a)

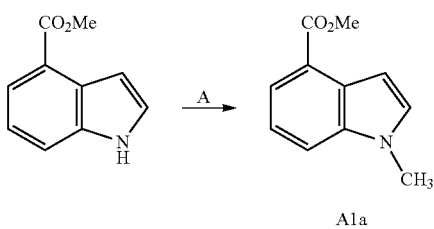

A1a

Conditions: A) NaH, CH₃I, DMF

Step A: To a stirring suspension of sodium hydride (60% dispersion in mineral oil, 9.90 g, 248 mmol) in DMF (150 mL) was slowly added a solution of methyl indole-4-carboxylate (10.0 g, 62.1 mmol) in DMF (100 mL) at room temperature under an atmosphere of nitrogen. The mixture stirred for 30 minutes, then iodomethane (15.4 mL, 248 mmol) was added and the mixture continued to stir at room temperature for an additional 16 hours. The mixture was quenched with a saturated solution of ammonium chloride (500 mL) and the aqueous mixture was extracted with ethyl acetate (3×300 mL). The combined organic layers were washed with water (4×300 mL) and brine (200 mL), dried ($Na_2SO_4$), filtered, and concentrated under reduced pressure. Purification of the resulting residue by column chromatography (0% to 30% ethyl acetate in hexanes) afforded methyl 1-methyl-1H-indole-4-carboxylate (A1a, 10.56 g, 90%) as an oil, which crystallized upon standing: $^1$H NMR (500 MHz, CDCl$_3$) δ 7.91 (d, J=1.7 Hz, 1H), 7.48 (d, J=1.6 Hz, 1H), 7.21 (m, 1H), 7.14 (s, 1H), 7.09 (s, 1H), 3.96 (s, 3H), 3.75 (s, 3H); MS (ESI+) m/z 190 (M+H).

Example 2

Preparation of Methyl 1-benzyl-1H-indole-4-carboxylate (A1b)

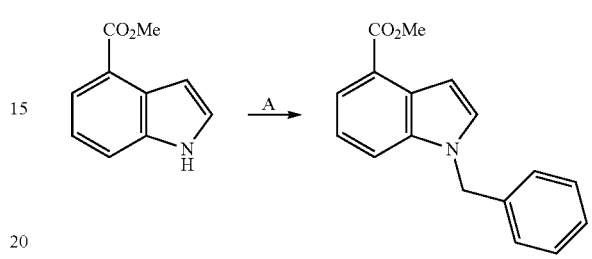

A1b

Conditions: A) BnBr, NaH or Cs₂CO₃, DMF

Step A: To a solution of methyl indole-4-carboxylate (10.0 g, 57.14 mmol) was added sodium hydride (60% dispersion in mineral oil (5.71 g, 142.8 mmol) in DMF (200 mL) in portions. The mixture was stirred under an atmosphere of nitrogen for 20 minutes. To this was added benzyl bromide (8.48 mL, 74.4 mmol) and the mixture continued to stir for 16 hours. The mixture was poured into an ice/water mixture and extracted with diethyl ether (3×500 mL). The combined organic layers were washed with brine (3×200 mL), dried ($Na_2SO_4$), filtered, and concentrated under reduced pressure. Purification by column chromatography (silica gel, 5 to 15% ethyl acetate in hexanes) afforded methyl 1-benzyl-1H-indole-4-carboxylate (A1b, 13.89 g, 92%) as a pale yellow oil, which crystallized upon standing: $^1$H NMR (500 MHz, CDCl$_3$) δ 7.90 (d, J=7.5 Hz, 1H), 7.46 (d, J=7.5 Hz, 1H), 7.30-7.25 (m, 4H), 7.20-7.16 (m, 2H), 7.10-7.05 (m, 2H), 5.36 (s, 2H), 3.98 (s, 3H); MS (ESI+) m/z 266 (M+H).

Example 3

Preparation of Methyl 3-formyl-1H-indazole-4-carboxylate (B1)

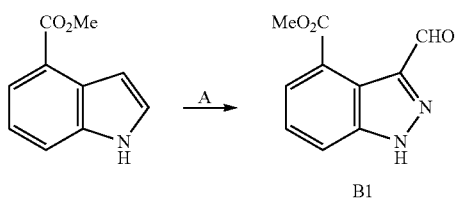

B1

Conditions: A) NaNO₂, 6N HCl, H₂O
Compound B₁, where R₁ = H was prepared using a modified procedure reported in patent WO02044183A2.

Step A: Aqueous HCl (56.0 mL of 6N solution in water, 0.33 mol) was added dropwise over 1 hour to a stirring suspension of methyl 1H-indole-4-carboxylate (5.0 g, 28.5 mmol) in a solution of sodium nitrite (24.0 g, 0.34 mol) in water (500 mL) at ambient temperature. The mixture was stirred overnight at ambient temperature, and then extracted with ethyl acetate (5×300 mL). The combined organic layers were washed with water (2×300 mL), brine (200 mL), and dried (Na$_2$SO$_4$). The organics were concentrated under reduced pressure until precipitation was observed. After cooling in a dry ice bath the precipitate was collected by filtration, washed with cold ethyl acetate (50 mL), and hexanes (100 mL) and dried (Na$_2$SO$_4$) to afford methyl 3-formyl-1H-indazole-4-carboxylate (B1, 2.1 g, 35%) as a yellow powder: $^1$H NMR (300 MHz, DMSO-d$_6$) δ 10.33 (s, 1H), 7.92 (d, J=8.1 Hz, 1H), 7.67 (d, J=7.2 Hz, 1H), 7.58 (t, J=7.2 Hz 1H), 3.96 (s, 3H); MS (ESI+) m/z 205 (M+H).

Example 4

Preparation of (S)-5-Methyl-2-(quinuclidin-8-yl)-2,3-dihydropyrrolo[4,3,2-de]isoquinolin-1(5H)-one, hydrochloride salt

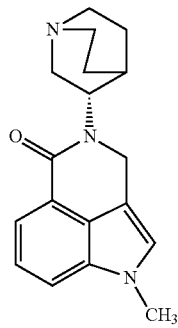 [SMILES: Cn1cc2c3c(cccc31)C(=O)N([C@@H]1CN3CCC1CC3)C2]

Step A: Following general procedure GP-A, (S)-(−)-3-aminoquinuclidine dihydrochloride and methyl 1-methyl-1H-indole-4-carboxylate (A1) were converted to (S)-methyl 1-methyl-3-[(quinuclidin-8-ylamino)methyl]-1H-indole-4-carboxylate: MS (ESI+) m/z 328 (M+H).

Step B: Following general procedure GP-B, (S)-1-methyl-3-[(quinuclidin-8-ylamino)methyl]-1H-indole-4-carboxylate was converted to lithium (S)-1-methyl-3-[(quinuclidin-8-ylamino)methyl]-1H-indole-4-carboxylate: MS (ESI+) m/z 314 (M+H).

Step C: Following general procedure GP-C, lithium (S)-1-methyl-3-[(quinuclidin-8-ylamino)methyl]-1H-indole-4-carboxylate was converted to (S)-5-methyl-2-(quinuclidin-8-yl)-2,3-dihydropyrrolo[4,3,2-de]isoquinolin-1(5H)-one, which was immediately treated with hydrochloric acid following general procedure GP-D to give (S)-5-methyl-2-(quinuclidin-8-yl)-2,3-dihydropyrrolo[4,3,2-de]isoquinolin-1(5H)-one, hydrochloride salt: $^1$H NMR (500 MHz, DMSO-d$_6$) δ 10.03 (bs, 1H), 7.56 (d, J=8.1 Hz, 1H), 7.38 (d, J=7.1 Hz, 1H), 7.22 (m, 2H), 5.13 (dd, J=14.3 Hz, 1.0 Hz, 2H), 4.71 (m, 1H), 3.83 (s, 3H), 3.73 (m, 1H), 3.48 (m, 1H), 3.31-3.19 (m, 3H), 2.42 (m, 1H), 2.18 (m 1H), 1.99-1.97 (m, 3H); MS (ESI+) m/z 296 (M+H); HPLC 98.4% (AUC), t$_R$ 9.80 min.

Example 5

Preparation of Endo-5-methyl-2-(9-methyl-9-azabicyclo[3.3.1]nonan-3-yl)-2,3-dihydropyrrolo[4,3,2-de]isoquinolin-1(5H)-one, hydrochloride salt

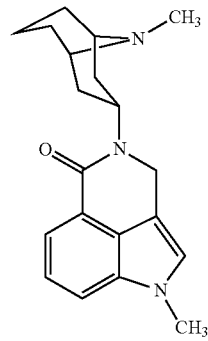 [SMILES: CN1C2CCCC1CC(N1Cc3cn(C)c4cccc(c34)C1=O)C2]

Step A: Following general procedure GP-A, endo-9-methyl-9-azabicyclo[3.3.1]nonan-3-amine dihydrochloride and methyl 1-methyl-1H-indole-4-carboxylate (A1) were converted to methyl 1-methyl-3-(endo-N-(9-methyl-9-azabicyclo[3.3.1]nonan-3-ylamino)methyl)-1H-indole-4-carboxylate: MS (ESI+) m/z 356 (M+H).

Step B: Following general procedure GP-B, methyl 1-methyl-3-(endo-N-(9-methyl-9-azabicyclo[3.3.1]nonan-3-ylamino)methyl)-1H-indole-4-carboxylate was converted to lithium 1-methyl-3-(endo-N-(9-methyl-9-azabicyclo[3.3.1]nonan-3-ylamino)methyl)-1H-indole-4-carboxylate: MS (ESI+) m/z 342 (M+H).

Step C: Following general procedure GP-C, lithium 1-methyl-3-(endo-N-(9-methyl-9-azabicyclo[3.3.1]nonan-3-ylamino)methyl)-1H-indole-4-carboxylate was converted to endo-N-(9-methyl-9-azabicyclo[3.3.1]nonan-3-yl)-2,3-dihydropyrrolo[4,3,2-de]isoquinolin-1(5H)-one, which was immediately treated with hydrochloric acid following general procedure GP-D to afford endo-N-(9-methyl-9-azabicyclo[3.3.1]nonan-3-yl)-2,3-dihydropyrrolo[4,3,2-de]isoquinolin-1(5H)-one, hydrochloride salt: $^1$H NMR (500 MHz, DMSO-d$_6$) δ 9.56 (bs, 1H), 7.53 (d, J=7.3 Hz, 1H), 7.38 (d, J=7.4 Hz, 1H), 7.22 (m, 2H), 5.10 (m, 1H), 4.92 (s, 2H), 3.89

(s, 3H), 2.81-2.63 (m, 3H), 2.26-1.79 (m, 8H), 1.54-1.10 (m, 4H); MS (ESI+) m/z 324 (M+H); HPLC>99% (AUC), $t_R$ 12.81 min.

Example 6

Preparation of (S)-2-Methyl-7-(quinuclidin-3-yl)-7,8-dihydropyrazolo[3,4,5-de]isoquinolin-6(2H)-one, hydrochloride salt

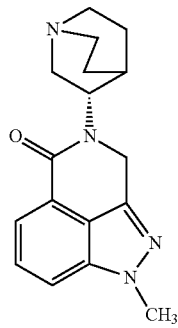 [SMILES: Cn1nc2c3c(cccc31)C(=O)N([C@@H]1CN3CCC1CC3)C2]

Step A: Following general procedure GP-E1, methyl 3-formyl-1H-indazole-4-carboxylate (B1) and iodomethane were converted to methyl 3-formyl-1-methyl-1H-indazole-4-carboxylate: $^1$H NMR (300 MHz, CDCl$_3$) δ 10.54 (s, 1H), 7.85 (dd, J=7.2, 0.78 Hz, 1H), 7.68 (dd, J=7.2, 078 Hz, 1H), 7.51 (t, J=7.2 Hz, 1H), 4.23 (s, 3H), 4.02 (s, 3H); MS (ESI+) m/z 218 (M+H); MS (ESI+) m/z 218 (M+H).

Step B: Following general procedure GP-F, (S)-(−)-3-aminoquinuclidine dihydrochloride and methyl 3-formyl-1-methyl-1H-indazole-4-carboxylate were converted to (S)-methyl 1-methyl-3-((quinuclidin-3-ylamino)methyl)-1H-indazole-4-carboxylate (64 mg, 32%): $^1$H NMR (500 MHz, MeOD) δ 7.85 (d, J=7.5 Hz, 1H), 7.81 (d, J=7.5 Hz, 1H), 7.50 (t, J=8.0 Hz, 1H), 4.31-4.24 (m, 2H), 4.08 (s, 3H), 3.98 (s, 3H), 3.12-3.06 (m, 2H), 3.02-2.90 (m, 3H), 2.78-2.70 (m, 1H), 2.12-2.05 (m, 2H), 1.98-1.80 (m, 2H), 1.72-1.66 (m, 1H), 1.63-1.53 (m, 1H); MS (ESI+) m/z 329 (M+H).

Step C: Following general procedure GP-G, To a solution of the product from Step C, (S)-methyl 1-methyl-3-((quinuclidin-3-ylamino)methyl)-1H-indazole-4-carboxylate was converted to lithium (S)-1-methyl-3-((quinuclidin-3-ylamino)methyl)-1H-indazole-4-carboxylate: MS (ESI) m/z 315 (M+H).

Step D: Following general procedure CP-H, lithium (S)-1-methyl-3-((quinuclidin-3-ylamino)methyl)-1H-indazole-4-carboxylate was converted to (S)-2-methyl-7-(quinuclidin-3-yl)-7,8-dihydropyrazolo[3,4,5-de]isoquinolin-6(2H)-one, which was immediately and treated with hydrochloric acid following general procedure GP-I to give (S)-2-methyl-7-(quinuclidin-3-yl)-7,8-dihydropyrazolo[3,4,5-de]isoquinolin-6(2H)-one, hydrochloride salt (40 mg, 83%) as an off-white solid: $^1$H NMR (500 MHz, DMSO-d$_6$) δ 10.01 (s, 1H), 7.76 (d, J=8.3 Hz, 1H), 7.53 (t, J=7.2 Hz, 1H), 7.44 (d, J=6.9 Hz, 1H), 5.26 (d, J=16.7 Hz, 1H), 5.14 (d, J=16.8 Hz, 1H), 4.77 (t, J=7.0 Hz, 1H), 4.09 (s, 3H), 3.72-3.70 (m, 1H), 3.56-3.47 (m, 2H), 3.40-3.28 (m, 3H), 3.23-3.21 (m, 1H), 2.22-2.19 (m, 1H), 2.00-1.84 (m, 3H); MS (ESI+) m/z 297 (M+H); HPLC 98.3% (AUC), $t_R$ 13.35 min.

Example 7

Preparation of (S)-2-Isopropyl-7-(quinuclidin-3-yl)-7,8-dihydropyrazolo[3,4,5-de]isoquinolin-6(2H)-one, hydrochloride salt

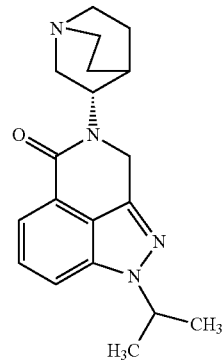 [SMILES: CC(C)n1nc2c3c(cccc31)C(=O)N([C@@H]1CN3CCC1CC3)C2]

Step A: Following general procedure GP-E1, methyl 3-formyl-1H-indazole-4-carboxylate (B2) and 2-iodopropane were converted to methyl 3-formyl-1-isopropyl-1H-indazole-4-carboxylate: $^1$H NMR (500 MHz, CDCl$_3$) δ 10.44 (s, 1H), 7.74 (d, J=7.0 Hz, 1H), 7.69 (d, J=7.0 Hz, 1H), 7.19 (t, J=7.0 Hz, 1H), 5.01-4.96 (m, 1H), 4.01 (s, 3H), 1.66 (d, J=7.0 Hz, 6H); MS (ESI+) m/z 247 (M+H).

Step B: Following general procedure GP-F, (S)-(−)-3-aminoquinuclidine dihydrochloride and methyl 3-formyl-1-isopropyl-1H-indazole-4-carboxylate were converted to (S)-methyl 1-isopropyl-3-[(quinuclidin-3-ylamino)methyl]-1H-indazole-4-carboxylate: MS (APCI+) m/z 357 (M+H).

Step C: Following general procedure GP-G, (S)-methyl 1-isopropyl-3-[(quinuclidin-3-ylamino)methyl]-1H-indazole-4-carboxylate was converted to lithium (S)-1-isopropyl-3-[(quinuclidin-3-ylamino)methyl]-1H-indazole-4-carboxylate: MS (ESI) m/z 343 (M+H).

Step D: Following general procedure GP-H, lithium (S)-1-isopropyl-3-[(quinuclidin-3-ylamino)methyl]-1H-indazole-4-carboxylate was converted to (S)-2-isopropyl-7-(quinuclidin-3-yl)-7,8-dihydropyrazolo[3,4,5-de]isoquinolin-6(2H)-one (72 mg, 45%) as a fluffy powder after lyophylization from acetonitrile/water: $^1$H NMR (300 MHz, MeOD) δ 7.67-7.62 (m, 1H), 7.50-7.48 (m, 2H), 5.31-5.14 (m, 2H), 4.98-4.91 (m, 1H), 4.78 (t, J=9.8 Hz, 1H), 3.49-3.33 (m, 1H), 3.18-3.11 (m, 2H), 2.98-2.80 (m, 3H), 2.21 (s, 1H), 2.12-2.09 (m, 1H), 1.90-1.81 (m, 2H), 1.73-1.65 (m, 1H), 1.57 (d, J=6.8 Hz, 6H); MS (APCI+) m/z 325 (M+H).

Step E: Following general procedure GP-I, (S)-2-isopropyl-7-(quinuclidin-3-yl)-7,8-dihydropyrazolo[3,4,5-de]isoquinolin-6(2H)-one was converted to (S)-2-isopropyl-7-(quinuclidin-3-yl)-7,8-dihydropyrazolo[3,4,5-de]isoquinolin-6(2H)-one, hydrochloride salt (57 mg, 65%) as an off-white solid: $^1$H NMR (500 MHz, DMSO-d$_6$) δ 10.30-9.90 (bs, 1H), 7.80 (d, J=8.4 Hz, 1H), 7.52-7.49 (m, 1H), 7.43 (d, J=7.1 Hz, 1H), 5.24 (d, J=16.7 Hz, 1H), 5.16 (d, J=16.8 Hz, 1H), 5.02-4.97 (m, 1H), 4.79 (t, J=9.0 Hz, 1H), 3.64 (t, J=9.0 Hz, 1H), 3.44-3.15 (m, 5H), 2.44 (s, 1H), 2.20-2.18 (m, 1H), 1.97-1.95

(m, 1H), 1.92-1.88 (m 1H), 1.82-1.77 (m, 1H), 1.53-1.50 (m, 6H); MS (ESI+) m/z 325 (M+H); HPLC>99% (AUC), $t_R$ 13.56 min.

Example 8

Preparation of (S)-Ethyl-7-(quinuclidin-3-yl)-7,8-dihydropyrazolo[3,4,5-de]isoquinolin-6(2H)-one, hydrochloride salt

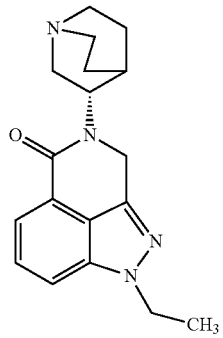 [SMILES: CCn1nc2c3c(cccc31)C(=O)N([C@@H]1CN3CCC1CC3)C2]

Step A: Following general procedure GP-E1, methyl 3-formyl-1H-indazole-4-carboxylate (B1) and 2-iodoethane were converted to methyl 3-formyl-1-ethyl-1H-indazole-4-carboxylate: $^1$H NMR (500 MHz, CDCl$_3$) δ 10.44 (s, 1H), 7.74 (d, J=7.0 Hz, 1H), 7.69 (d, J=7.0 Hz, 1H), 7.19 (t, J=7.0 Hz, 1H), 5.01-4.96 (m, 1H), 4.01 (s, 3H), 1.66 (d, J=7.0 Hz, 6H); MS (ESI+) m/z 233 (M+H).

Step B: Following general procedure GP-F, (S)-(−)-3-aminoquinuclidine dihydrochloride and methyl 3-formyl-1-ethyl-1H-indazole-4-carboxylate were converted to (S)-methyl 1-ethyl-3-((quinuclidin-3-ylamino)methyl)-1H-indazole-4-carboxylate: MS (APCI+) m/z 343 (M+H).

Step C: Following general procedure GP-G, (S)-methyl 1-ethyl-3-((quinuclidin-3-ylamino)methyl)-1H-indazole-4-carboxylate was converted to lithium (S)-1-ethyl-3-((quinuclidin-3-ylamino)methyl)-1H-indazole-4-carboxylate: MS (ESI) m/z 329 (M+H).

Step D: Following general procedure GP-H, lithium (S)-1-ethyl-3-((quinuclidin-3-ylamino)methyl)-1H-indazole-4-carboxylate was converted to (S)-2-ethyl-7-(quinuclidin-3-yl)-7,8-dihydropyrazolo[3,4,5-de]isoquinolin-6(2H)-one: MS (APCI+) m/z 311 (M+H).

Step E: Following general procedure GP-I, (S)-2-ethyl-7-(quinuclidin-3-yl)-7,8-dihydropyrazolo[3,4,5-de]isoquinolin-6(2H)-one was converted to (S)-2-ethyl-7-(quinuclidin-3-yl)-7,8-dihydropyrazolo[3,4,5-de]isoquinolin-6(2H)-one, hydrochloride salt: $^1$H NMR (500 MHz, DMSO-d$_6$) δ 10.30-9.90 (bs, 1H), 7.80 (d, J=8.4 Hz, 1H), 7.52-7.49 (m, 1H), 7.43 (d, J=7.1 Hz, 1H), 5.24 (d, J=16.7 Hz, 1H), 4.79 (t, J=9.0 Hz, 1H), 4.47 (q, J=7.0 Hz, 2H), 3.64 (t, J=9.0 Hz, 1H), 3.54-3.48 (m, 2H), 3.35-3.21 (m, 3H), 2.53-2.48 (m, 1H), 2.20-2.18 (m, 1H), 1.97-1.95 (m, 1H), 1.92-1.88 (m, 1H), 1.82-1.77 (m, 1H), 1.43 (t, J=7.0 Hz, 3H); MS (ESI+) m/z 311 (M+H); HPLC>99% (AUC), $t_R$ 12.57 min.

Example 9

Preparation of (S)-Isobutyl-7-(quinuclidin-3-yl)-7,8-dihydropyrazolo[3,4,5-de]isoquinolin-6(2H)-one, hydrochloride salt

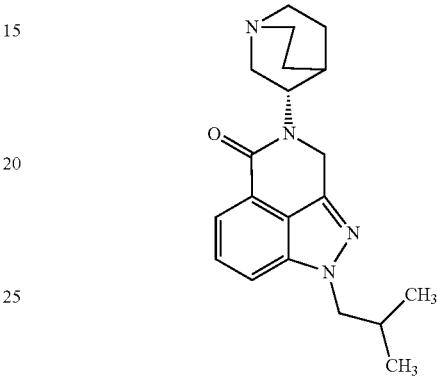

Step A: Following general procedure GP-E1, methyl 3-formyl-1H-indazole-4-carboxylate (B1) and bromo-2-methylpropane were converted to methyl 3-formyl-1-isobutyl-1H-indazole-4-carboxylate: $^1$H NMR (500 MHz, CDCl$_3$) δ 10.63 (s, 1H), 8.16-8.02 (m, 1H), 8.01-8.00 (m, 1H), 7.54-7.51 (m, 1H), 4.67-4.66 (m, 2H), 3.93 (s, 3H), 2.28-2.22 (m, 1H), 0.89-0.82 (m, 6H); MS (ESI+) m/z 261 (M+H).

Step B: Following general procedure GP-F, (S)-(−)-3-aminoquinuclidine dihydrochloride and methyl 3-formyl-1-isobutyl-1H-indazole-4-carboxylate were converted to (S)-methyl 1-isobutyl-3-[(quinuclidin-3-ylamino)methyl]-1H-indazole-4-carboxylate: MS (APCI+) m/z 371 (M+H).

Step C: Following general procedure GP-G, (S)-methyl 1-isobutyl-3-[(quinuclidin-3-ylamino)methyl]-1H-indazole-4-carboxylate was converted to lithium (S)-1-isobutyl-3-[(quinuclidin-3-ylamino)methyl]-1H-indazole-4-carboxylate: MS (ESI) m/z 357 (M+H).

Step D: Following general procedure GP-H, lithium (S)-1-isobutyl-3-[(quinuclidin-3-ylamino)methyl]-1H-indazole-4-carboxylate was converted to (S)-2-isobutyl-7-(quinuclidin-3-yl)-7,8-dihydropyrazolo[3,4,5-de]isoquinolin-6(2H)-one: $^1$H NMR (500 MHz, MeOD) δ 7.69-7.65 (m, 1H), 7.56-7.54 (m, 2H), 5.32-5.15 (m, 2H), 4.70-4.67 (m, 1H), 4.26-4.24 (m, 2H), 3.89-3.81 (m, 2H), 3.64-3.42 (m, 1H), 3.41-3.39 (m, 2H), 2.63-2.13 (m, 7H), 0.95-0.91 (m, 6H); MS (APCI+) m/z 339(M+H).

Step E: Following general procedure GP-I, (S)-2-isobutyl-7-(quinuclidin-3-yl)-7,8-dihydropyrazolo[3,4,5-de]isoquinolin-6(2H)-one was converted to (S)-2-isobutyl-7-(quinuclidin-3-yl)-7,8-dihydropyrazolo[3,4,5-de]isoquinolin-6(2H)-one, hydrochloride salt: $^1$H NMR (500 MHz, DMSO-d$_6$) δ 10.05-9.59 (bs, 1H), 7.85-7.72 (m, 1H), 7.61-7.46 (m, 1H), 7.46-7.32 (m, 1H), 5.28 (d, J=17.0 Hz, 1H), 5.15 (d, J=17.0 Hz, 1H), 4.87-4.64 (m, 1H), 4.33-4.14 (m, 2H), 3.66-3.52 (m, 1H), 3.51-3.26 (m, 1H), 3.25-2.92 (m, 3H), 2.40-

2.31 (m, 1H), 2.31-2.05 (m, 2H), 2.05-1.54 (m, 4H), 0.96-0.79 (m 6H MS (ESI+) m/z 339 (M+H); HPLC>99% (AUC), $t_R$ 12.32 min.

Example 10

Preparation of (S)-2-(4-Fluorophenyl)-7-(quinuclidin-3-yl)-7,8-dihydropyrazolo[3,4,5-de]isoquinolin-6(2H)-one, hydrochloride salt

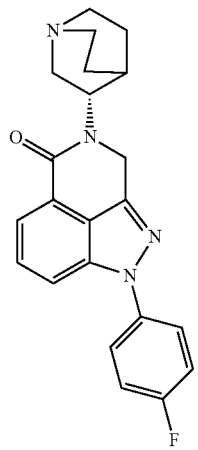 [SMILES: O=C1c2cccc3c2c(nn3-c2ccc(F)cc2)CN1[C@@H]1CN2CCC1CC2]

Step A: Following general procedure GP-E2, methyl 3-formyl-1H-indazole-4-carboxylate (B1) and 4-fluorophenylboronic acid were converted to methyl 3-formyl-(4-fluorophenyl)-1H-indazole-4-carboxylate: $^1$H NMR (300 MHz, DMSO-$d_6$) δ 10.39 (s, 1H), 8.02 (d, J=9.6 Hz, 1H), 7.92-7.88 (m, 2H), 7.80 (d, J=6.9 Hz, 1H), 7.72-7.69 (m, 1H), 7.56-7.50 (m, 2H), 3.92 (s, 3H); MS (ESI+) m/z 299 (M+H).

Step B: Following general procedure GP-F, (S)-(−)-3-aminoquinuclidine and methyl 3-formyl-(4-fluorophenyl)-1H-indazole-4-carboxylate were converted to (S)-methyl 1-(4-fluorophenyl)-3-[(quinuclidin-3-ylamino)methyl]-1H-indazole-4-carboxylate: MS (ESI+) m/z 409 (M+H).

Step C: Following general procedure GP-G, (S)-methyl 1-(4-fluorophenyl)-3-[(quinuclidin-3-ylamino)methyl]-1H-indazole-4-carboxylate was converted to lithium (S)-1-(4-fluorophenyl)-3-[(quinuclidin-3-ylamino)methyl]-indazole-4-carboxylate which was used in the next step without further purification: MS (ESI−) m/z 393 (acid, M−H).

Step D: Following general procedure GP-H, lithium (S)-1-(4-fluorophenyl)-3-[(quinuclidin-3-ylamino)methyl]-indazole-4-carboxylate was converted to (S)-2-(4-fluorophenyl)-7-(quinuclidin-3-yl)-7,8-dihydropyrazolo[3,4,5-de]isoquinolin-6(2H)-one: $^1$H NMR (500 MHz, DMSO-$d_6$) δ 9.60-9.40 (bs, 1H), 8.03 (d, J=8.5 Hz, 1H), 7.90-7.88 (m, 2H), 7.70-7.67 (m, 1H), 7.60-7.59 (m, 1H), 7.46-7.43 (m, 2H), 5.38 (d, J=17.5 Hz, 1H), 5.24 (d, J=17.5 Hz, 1H), 4.70-4.80 (m, 1H), 3.60-3.45 (m, 1H), 2.92-2.15 (m, 3H), 2.35-1.60 (m, 6H); MS (ESI+) m/z 377 (M+H).

Step E: Following general procedure GP-I, (S)-2-(4-fluorophenyl)-7-(quinuclidin-3-yl)-7,8-dihydropyrazolo[3,4,5-de]isoquinolin-6(2H)-one was converted to (S)-2-(4-fluorophenyl)-7-(quinuclidin-3-yl)-7,8-dihydropyrazolo[3,4,5-de]isoquinolin-6(2H)-one, hydrochloride salt: $^1$H NMR (500 MHz, DMSO-$d_6$) δ 9.96-9.50 (bs, 1H), 8.12-7.93 (m, 1H), 7.93-7.81 (m, 2H), 7.75-7.66 (m, 1H), 7.65-7.52 (m, 1H), 7.45-7.42 (m, 2H), 5.37 (d, J=17.4 Hz, 1H), 5.24 (d, J=17.4 Hz, 1H), 4.88-4.64 (bs, 1H), 3.57-3.40 (m, 1H), 3.21-2.84 (m, 4H), 2.46-1.47 (m, 6H); MS (ESI+) m/z 377 (M+H); HPLC 98.0% (AUC), $t_R$ 13.39 min.

Example 11

Preparation of (S)-7-(Quinuclidin-3-yl)-7,8-dihydropyrazolo[3,4,5-de]isoquinolin-6(2H)-one, hydrochloride salt

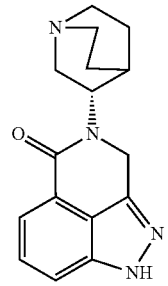 [SMILES: O=C1c2cccc3[nH]nc(c23)CN1[C@@H]1CN2CCC1CC2]

Step A: A mixture of methyl 3-formyl-1H-indazole-4-carboxylate (B1) (5.0 g, 24.5 mmol) and sodium hydride (1.2 g, 29.4 mmol) in THF/DMF (5.5:1, 260 mL) was cooled to 0° C. (2-(Chloromethoxy)ethyl)trimethylsilane (5.20 mL, 29.4 mmol) was added and then the reaction mixture allowed to stir at ambient temperature for 18 h. The mixture was quenched with a saturated solution of NaHCO$_3$ (100 mL) and extracted with ethyl acetate (3×). The combined organic layers were washed with brine (100 mL), dried (Na$_2$SO$_4$), filtered, and concentrated under reduced pressure. Purification of the resulting residue by column chromatography (silica gel, 5% to 35% ethyl acetate in hexanes) afforded the desired product as a mixture of regioisomers: methyl 3-formyl-2((2-(trimethylsilyl)ethoxy)methyl)-2H-indazole-4-carboxylate (2.06 g, 25%) as a yellow solid: $^1$H NMR (300 MHz, CDCl$_3$) δ 10.97 (s, 1H), 8.21-8.10 (m, 2H), 7.50 (dd, J=8.7, 7.5 Hz, 1H), 6.25 (s, 2H), 4.04 (s, 3H), 3.71 (dd, J=8.4, 8.4, 2H), 0.89 (dd, J=8.4, 8.4 Hz, 2H), 0.00 (s, 9H); MS (ESI+) m/z 335 (M+H)$^+$ and methyl 3-formyl-1-((2-(trimethylsilyl)ethoxy)methyl)-1H-indazole-4-carboxylate (4.96 g, 60%) as a yellow solid: $^1$H NMR (300 MHz, CDCl$_3$) δ 10.54 (s, 1H), 7.89-7.83 (m, 2H), 7.55 (dd, J=8.4, 7.5 Hz, 1H), 5.88 (s, 2H), 4.03 (s, 3H), 3.56 (dd, J=9.3, 8.1, 2H), 0.89 (dd, J=8.4, 8.4 Hz, 2H), −0.01 (s, 9H); MS (ESI+) m/z 335 (M+H)$^+$.

Step B: Following general procedure GP-F, except that dioxane was used as solvent and sodium hydride was used as base, methyl 3-formyl-1-((2-(trimethylsilyl)ethoxy)methyl)-1H-indazole-4-carboxylate was converted to (S)-methyl 3-((quinuclidin-3-ylamino)methyl)-1-((2-(trimethylsilyl)ethoxy)methyl)-1H-indazole-4-carboxylate (1.77 g, 85%): $^1$H NMR (500 MHz, CDCl$_3$) δ 7.81 (dd, J=7.5, 0.5 Hz, 1H), 7.75 (d, J=8.0 Hz, 1H), 7.44 (dd, J=8.0, 7.5 Hz, 1H), 5.82 (s, 2H), 4.32-4.20 (m, 2H), 3.99 (s, 3H), 3.56 (dd, J=8.5, 8.5, 2H), 3.48 (dd, J=2.5 Hz, 2H), 3.18-3.10 (m, 1H), 2.98-2.72 (m, 5H), 2.58-2.52 (m, 1H), 2.06-1.90 (m, 1H), 1.70-1.66 (m, 1H), 1.52-1.46 (m, 1H), 1.40-1.34 (m, 1H), 0.89 (dd, J=8.4, 8.4 Hz, 2H), −0.05 (s, 9H); MS (ESI+) m/z 445 (M+H)⁺.

Step C: Following general procedure GP-G, (S)-methyl 3-((quinuclidin-3-ylamino)methyl)-1-((2-(trimethylsilyl) ethoxy)methyl)-1H-indazole-4-carboxylate (1.77 g) was converted to crude lithium (S)-3-((quinuclidin-3-ylamino) methyl)-1-((2-(trimethylsilyl)ethoxy)methyl)-1H-indazole-4-carboxylate; MS (ESI) m/z 431 (acid M+H)⁺.

Step D: To a mixture of crude lithium (S)-3-((quinuclidin-3-ylamino)methyl)-1-((2-(trimethylsilyl)ethoxy)methyl)-1H-indazole-4-carboxylate (1.73 g, 3.98 mmol) from Step C above in pyridine (10 mL) at 0° C. was added thionyl chloride (3.0 mL, 39.8 mmol) dropwise over 5 min. Stirring was continued for 5 min and then the reaction mixture allowed to warm to ambient temperature and stirred for an additional 2 h. The reaction mixture was concentrated under reduced pressure and the crude material was purified by column chromatography (silica gel, 5 to 100% 90:9:1 dichloromethane/methanol/concentrated ammonium hydroxide in dichloromethane) to afford partially pure desired product (9.21 g). This material was dissolved in methanol (40 mL) and treated with 7N ammonium hydroxide in methanol, the solid formed was filtered and the filtrate concentrated under reduced pressure to afford (S)-7-(quinuclidin-3-yl)-2-((2-(trimethylsilyl)ethoxy)methyl)-7,8-dihydropyrazolo[3,4,5-de]isoquinolin-6(2H)-one (1.50 g, 91%) as a pale yellow solid: ¹H NMR (500 MHz, CDCl₃) δ 7.70 (d, J=7.0 Hz, 1H), 7.64 (d, J=8.0 Hz, 1H), 7.58 (dd, J=7.0, 7.0 Hz, 1H). 5.76 (s, 2H), 5.26-5.12 (m, 2H), 4.78-4.72 (m, 1H), 3.97-3.70 (m, 3H), 3.60-3.22 (m, 5H), 2.60-1.90 (m, 5H), 0.96 (dd, J=5.5, 5.5 Hz, 2H), −0.05 (s, 9H); MS (ESI) m/z 413 (M+H)⁺.

Step E: To a sealed tube containing a solution of (S)-7-(quinuclidin-3-yl)-2-((2-(trimethylsilyl)ethoxy)methyl)-7,8-dihydropyrazolo[3,4,5-de]isoquinolin-6(2H)-one (0.71 g, 1.73 mmol) from Step D above in dioxane (10 mL) was added 6N HCl (20 mL). The reaction mixture was flushed with argon, sealed and heated to 115° C. for 30 min, cooled to ambient temperature and concentrated under reduced pressure. The residue was preabsorbed on silica gel and purified first by column chromatography (5 to 20% 6:3:1 dichloromethane/methanol/concentrated ammonium hydroxide in 9:1 dichloromethane/methanol) and subsequently by reverse phase semi-preparative HPLC (isocratic, 10% acetonitrile in water—both eluents contained 0.05% trifluoroacetic acid as modifier). The solvents were removed in vacuo and the desired product trifluoroacetate salt was dissolved in a solution 1.25 N HCl in methanol (4×5 mL) and the solvent removed (4×) to exchange the trifluoroacetate salt to the hydrochloride salt form. Recrystallization of the desired product hydrochloride salt from ethanol (10 mL), followed by lyophilization from acetonitrile/water (1:5, 6 mL) afforded (S)-7-(quinuclidin-3-yl)-7,8-dihydropyrazolo[3,4,5-de]isoquinolin-6(2H)-one, hydrochloride salt (85.9 mg, 18%) as an amorphous white solid: ¹H NMR (500 MHz, d₆-DMSO) δ 13.15 (s, 1H), 10.15 (s, 1H), 7.65 (d, J=8.5 Hz, 1H), 7.75 (dd, J=7.0, 7.0 Hz, 1H), 7.45 (d, J=7.0 Hz, 1H), 5.32-5.14 (m, 2H), 4.79 (t, J=9.5 Hz, 1H), 3.78-3.47 (m, 4H), 3.32-3.16 (m, 3H), 2.26-2.18 (m, 1H), 2.03-1.80 (m, 3H), MS (ESI+) m/z 283 (M+H)⁺; HPLC 98.8% (AUC), $t_R$ 7.29 min.

Example 12

Preparation of (R)-2-Methyl-7-(quinuclidin-3-yl)-7,8-dihydropyrazolo[3,4,5-de]isoquinolin-6(2H)-one, hydrochloride salt

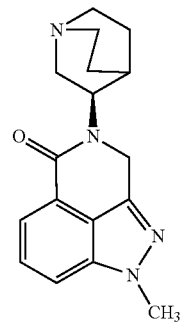 [SMILES: Cn1nc2c3c(cccc31)C(=O)N([C@H]1CN3CCC1CC3)C2]

Step A: Following general procedure GP-F, (R)-(+)-3-aminoquinuclidine dihydrochloride and methyl 3-formyl-1-methyl-1H-indazole-4-carboxylate were converted to (R)-methyl 1-methyl-3-[(quinuclidin-3-ylamino)methyl]-1H-indazole-4-carboxylate: MS (APCI+) m/z 329 (M+H).

Step B: Following general procedure GP-G, (R)-methyl 1-methyl-3-[(quinuclidin-3-ylamino)methyl]-1H-indazole-4-carboxylate was converted to lithium (R)-1-methyl-3-((quinuclidin-3-ylamino)methyl)-1H-indazole-4-carboxylate: MS (ESI) m/z 315 (M+H).

Step C: Following general procedure GP-H, (R)-1-methyl-3-[(quinuclidin-3-ylamino)methyl]-1H-indazole-4-carboxylate was converted to (S)-2-methyl-7-(quinuclidin-3-yl]-7,8-dihydropyrazolo[3,4,5-de]isoquinolin-6(2H)-one, which was immediately treated with hydrochloric acid following general procedure GP-I to give (R)-2-methyl-7-(quinuclidin-3-yl)-7,8-dihydropyrazolo[3,4,5-de]isoquinolin-6(2H)-one, hydrochloride salt: ¹H NMR (500 MHz, DMSO-d₆) δ 10.20 (s, 1H), 7.76 (d, J=8.0 Hz, 1H), 7.53 (t, J=7.0 Hz, 1H), 7.40 (d, J=6.5 Hz, 1H), 5.27 (d, J=17.0 Hz, 1H), 5.15 (d, J=16.5 Hz, 1H), 4.77 (t, J=9.0 Hz, 1H), 4.08 (s, 3H), 3.72-3.69 (m, 1H), 3.58-3.48 (m, 2H), 3.40-3.28 (m, 2H), 3.22-3.18 (m, 1H), 2.46-2.42 (m, 1H), 2.28-2.14 (m, 1H), 2.08-1.84 (m, 3H); MS (ESI+) m/z 297 (M+H); HPLC 98.7% (AUC), $t_R$ 13.39 min.

Example 13

Preparation of (R)-4-Fluoro-2-methyl-7-(quinuclidin-3-yl)-7,8-dihydropyrazolo[3,4,5-de]isoquinolin-6(2H)-one, hydrochloride salt

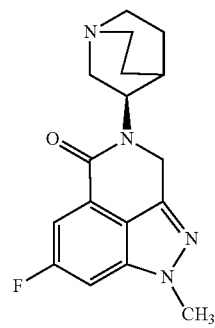 [SMILES: Cn1nc2c3c(cc(F)cc31)C(=O)N([C@H]1CN3CCC1CC3)C2]

Step A: Following general procedure GP-E1, methyl 6-fluoro-3-formyl-1H-indazole-4-carboxylate was converted to methyl 6-fluoro-3-formyl-1-methyl-1H-indazole-4-carboxylate: ¹H NMR (500 MHz, CDCl₃) δ 10.44 (s, 1H), 7.57 (dd, J=9.1, 2.1 Hz, 1H), 7.30 (dd, J=7.9, 2.1 Hz, 1H), 4.18 (s, 3H), 4.01 (s, 3H); MS (ESI+) m/z 237 (M+H).

Step B: Following general procedure GP-F, (R)-(+)-3-aminoquinuclidine dihydrochloride and methyl 6-fluoro-3-formyl-1-methyl-1H-indazole-4-carboxylate were converted to (R)-methyl 6-fluoro-1-methyl-3-((quinuclidin-3-ylamino)methyl)-1H-indazole-4-carboxylate: ¹H NMR (500 MHz, CDCl₃) δ 7.52 (d, J=9.5 Hz, 1H), 7.18 (d, J=8.4 Hz, 1H), 5.35 (br s, 1H), 4.24 (d, J=13.7 Hz, 1H), 4.16 (d, J=13.7 Hz, 1H), 4.00 (s, 3H), 3.98 (s, 3H), 3.17-3.12 (m, 1H), 2.93-2.91 (m, 1H), 2.83-2.75 (m, 4H), 2.53-2.50 (m, 1H), 2.02 (br s, 1H), 1.74-1.62 (m, 2H), 1.56-1.44 (m, 1H), 1.41-1.31 (m, 1H); MS (ESI+) m/z 347 (M+H).

Step C: Following general procedure GP-G, (R)-methyl 6-fluoro-1-methyl-3-((quinuclidin-3-ylamino)methyl)-1H-indazole-4-carboxylate was converted to lithium (R)-6-fluoro-1-methyl-3-((quinuclidin-3-ylamino)methyl)-1H-indazole-4-carboxylate: MS (ESI) m/z 333 (M+H).

Step D: Following general procedure GP-H, lithium (R)-6-fluoro-1-methyl-3-((quinuclidin-3-ylamino)methyl)-1H-indazole-4-carboxylate was converted to (R)-4-fluoro-2-methyl-7-(quinuclidin-3-yl)-7,8-dihydropyrazolo[3,4,5-de]isoquinolin-6(2H)-one and purified by preparative HPLC: ¹H NMR (500 MHz, CD₃OD) δ 7.44 (dd, J=9.7, 1.6 Hz, 1H), 7.30 (dd, J=9.0, 1.6 Hz, 1H), 5.27 (d, J=17.0 Hz, 1H), 5.16 (d, J=17.0 Hz, 1H), 4.71 (dd, J=9.7, 8.1 Hz, 1H), 4.07 (s, 3H), 3.91-3.79 (m, 2H), 3.70-3.64 (m, 1H), 3.46-3.33 (m, 3H), 2.64 (br s, 1H), 2.43-2.37 (m, 1H), 2.19-2.11 (m, 2H), 2.06-2.00 (m, 1H); MS (ESI+) m/z 315 (M+H).

Step E: Following general procedure GP-I, (R)-4-fluoro-2-methyl-7-(quinuclidin-3-yl)-7,8-dihydropyrazolo[3,4,5-de]isoquinolin-6(2H)-one was converted to (R)-4-fluoro-2-methyl-7-(quinuclidin-3-yl)-7,8-dihydropyrazolo[3,4,5-de]isoquinolin-6(2H)-one, hydrochloride salt: ¹H NMR (500 MHz, DMSO-d₆) δ 10.28 (s, 1H), 7.72 (dd, J=10.2, 1.4 Hz, 1H), 7.25 (dd, J=9.0, 1.3 Hz, 1H), 5.28 (d, J=17.0 Hz, 1H), 5.16 (d, J=17.0 Hz, 1H), 4.77 (t, J=9.0 Hz, 1H), 4.06 (s, 3H), 3.72 (t, J=11.6 Hz, 1H), 3.56-3.46 (m, 2H), 3.37-3.28 (m, 3H), 3.24-3.18 (m, 1H), 2.21-2.16 (m, 1H), 2.03-1.82 (m, 3H); MS (ESI+) m/z 315 (M+H); HPLC>99% (AUC), $t_R$ 12.39 min.

Example 14

Preparation of (R)-2-Ethyl-7-(quinuclidin-3-yl)-7,8-dihydropyrazolo[3,4,5-de]isoquinolin-6(2H)-one, hydrochloride salt

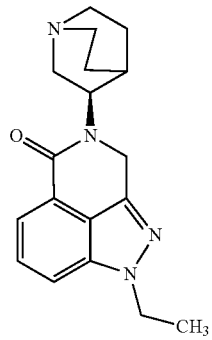 [SMILES: CCn1nc2c3c(cccc31)C(=O)N([C@H]1CN3CCC1CC3)C2]

Step A: Following general procedure GP-F, (R)-(+)-3-aminoquinuclidine dihydrochloride and methyl 3-formyl-1-ethyl-1H-indazole-4-carboxylate were converted to (R)-methyl 1-ethyl-3-[(quinuclidin-3-ylamino)methyl]-1H-indazole-4-carboxylate: MS (APCI+) m/z 343 (M+H).

Step B: Following general procedure GP-G, (R)-methyl 1-ethyl-3-((quinuclidin-3-ylamino)methyl)-1H-indazole-4-carboxylate was converted to lithium (R)-1-ethyl-3-[(quinuclidin-3-ylamino)methyl]-1H-indazole-4-carboxylate: MS (ESI+) m/z 329 (M+H).

Step C: Following general procedure GP-H, lithium (R)-1-ethyl-3-[(quinuclidin-3-ylamino)methyl]-1H-indazole-4-carboxylate was converted to (S)-2-ethyl-7-(quinuclidin-3-yl)-7,8-dihydropyrazolo[3,4,5-de]isoquinolin-6(2H)-one: MS (APCI+) m/z 311 (M+H).

Step D: Following general procedure GP-I, (R)-2-ethyl-7-(quinuclidin-3-yl)-7,8-dihydropyrazolo[3,4,5-de]isoquinolin-6(2H)-one was converted to (R)-2-ethyl-7-(quinuclidin-3-yl)-7,8-dihydropyrazolo[3,4,5-de]isoquinolin-6(2H)-one, hydrochloride salt: ¹H NMR (500 MHz, DMSO-d₆) δ 10.47 (s, 1H), 7.79 (d, J=8.3 Hz, 1H), 7.54-7.51 (m, 1H), 7.44 (d, J=7.0 Hz 1H), 5.29 (d, J=16.8 Hz, 1H), 5.15 (d, J=16.8 Hz, 1H), 4.78-4.76 (m, 1H), 4.50-4.45 (m, 2H), 3.72-3.68 (m, 1H), 3.56-3.42 (m, 2H), 3.36-3.28 (m, 2H), 3.23-3.16 (m, 1H), 2.46-2.42 (m, 1H), 2.28-2.13 (m, 1H), 2.06-1.78 (m, 3H), 1.42 (t, J=7.0 Hz, 3H); MS (ESI+) m/z 311 (M+H); HPLC 98.5% (AUC), $t_R$ 13.84 min.

Example 15

Preparation of (R)-2-Isopropyl-7-(quinuclidin-3-yl)-7,8-dihydropyrazolo[3,4,5-de]isoquinolin-6(2H)-one, hydrochloride salt

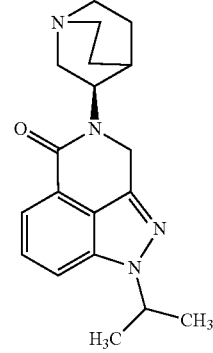 [SMILES: CC(C)n1nc2c3c(cccc31)C(=O)N([C@H]1CN3CCC1CC3)C2]

Step A: Following general procedure GP-F, (R)-(+)-3-aminoquinuclidine dihydrochloride and methyl 3-formyl-1-isopropyl-1H-indazole-4-carboxylate were converted to (R)-methyl 1-isopropyl-3-[(quinuclidin-3-ylamino)methyl]-1H-indazole-4-carboxylate: MS (APCI+) m/z 357 (M+H).

Step B: Following general procedure GP-G, (R)-methyl 1-isopropyl-3-[(quinuclidin-3-ylamino)methyl]-1H-indazole-4-carboxylate was converted to lithium (R)-1-isopropyl-3-[(quinuclidin-3-ylamino)methyl]-1H-indazole-4-carboxylate which was used in the next step without further purification: MS (ESI) m/z 343 (M+H).

Step C: Following general procedure GP-H, (R)-1-isopropyl-3-[(quinuclidin-3-ylamino)methyl]-1H-indazole-4-carboxylate was converted to (R)-2-isopropyl-7-(quinuclidin-3-yl)-7,8-dihydropyrazolo[3,4,5-de]isoquinolin-6(2H)-one: ¹H NMR (300 MHz, MeOD) δ 7.67-7.62 (m, 1H), 7.50-7.48

(m, 2H), 5.31-5.14 (m, 2H), 4.98-4.91 (m, 1H), 4.78 (t, J=9.8 Hz, 1H), 3.49-3.33 (m, 1H), 3.18-3.11 (m, 2H), 2.98-2.80 (m, 3H), 2.21 (s, 1H), 2.12-2.09 (m, 1H), 1.90-1.81 (m, 2H), 1.73-1.65 (m, 1H), 1.57 (d, J=6.8 Hz, 6H); MS (APCI+) m/z 325 (M+H).

Step D: Following general procedure GP-I, (R)-2-isopropyl-7-(quinuclidin-3-yl)-7,8-dihydropyrazolo[3,4,5-de]isoquinolin-6(2H)-one was converted to (R)-2-isopropyl-7-(quinuclidin-3-yl)-7,8-dihydropyrazolo[3,4,5-de]isoquinolin-6(2H)-one, hydrochloride salt: $^1$H NMR (500 MHz, DMSO-$d_6$) δ 10.30-9.90 (bs, 1H), 7.80 (d, J=8.4 Hz, 1H), 7.52-7.49 (m, 1H), 7.43 (d, J=7.1 Hz 1H), 5.24 (d, J=16.7 Hz, 1H), 5.16 (d, J=16.8 Hz, 1H), 5.02-4.97 (m, 1H), 4.79 (t, J=9.0 Hz, 1H), 3.64 (t, J=9.0 Hz, 1H), 3.44-3.15 (m, 5H), 2.44 (s, 1H), 2.20-2.18 (m, 1H), 1.97-1.95 (m, 1H), 1.92-1.88 (m 1H), 1.82-1.77 (m, 1H), 1.53-1.50 (m, 6H); MS (ESI+) m/z 325 (M+H); HPLC>99% (AUC), $t_R$ 8.87 min.

Example 16

Preparation of (R)-7-(Quinuclidin-3-yl)-7,8-dihydropyrazolo[3,4,5-de]isoquinolin-6(2H)-one, hydrochloride salt

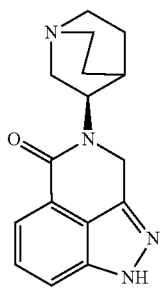 [SMILES: O=C1c2cccc3[nH]nc(c23)CN1[C@H]1CN2CCC1CC2]

Step A: To a stirred suspension of (R)-(+)-3-aminoquinuclidine dihydrochloride (916.0 mg, 4.6 mmol) in dichloromethane (60 mL) was added sodium hydride (368 mg, 9.2 mmol) in portions and the mixture was stirred for 1 h. Acetic acid (0.15 mL) was added dropwise. Then methyl 3-formyl-1H-indazole-4-carboxylate (B1) (776 mg, 3.8 mmol) was added and the mixture continued to stir at room temperature for an additional 2 h. Sodium triacetoxyborohydride (4.2 g, 19.6 mmol) was added in one portion and stirring was continued overnight at room temperature. The solvent was removed under reduced pressure, and the crude material was purified by column chromatography (silica gel, 90:10:1 dichloromethane/methanol/concentrated ammonium hydroxide) to afford (R)-methyl 3-((quinuclidin-3-ylamino)methyl)-1H-indazole-4-carboxylate as a brown solid (2.15 g, quant. yield): $^1$H NMR (500 MHz, CDCl$_3$) δ 7.80 (dd, J=7.2, 0.7 Hz, 1H), 7.68 (dd, J=8.4, 0.7 Hz 1H), 7.36 (dd, J=8.3, 7.3 Hz, 1H), 4.30 (d, J=14.2 Hz, 1H), 4.25 (d, J=14.2 Hz, 1H), 3.96 (s, 3H), 3.28-3.25 (m, 1H), 3.12-3.07 (m, 1H), 2.99-2.91 (m, 4H), 2.73-2.69 (m, 1H), 2.19-2.12 (m, 1H), 2.04-2.00 (m, 1H), 1.80-1.74 (m, 1H), 1.65-1.57 (m, 1H), 1.52-1.46 (m, 1H). MS (ESI+) m/z 315 (M+H)

Step B: To a solution of (R)-methyl 3-((quinuclidin-3-ylamino)methyl)-1H-indazole-4-carboxylate (1.8 g, 5.7 mmol) from Step A above in THF (30 ml) and H$_2$O (30 ml) was added lithium hydroxide monohydrate (721 mg, 17.2 mmol). The mixture was stirred at room temperature overnight and then concentrated under reduced pressure. The residue was dried overnight under vacuum to afford crude lithium (R)-3-((quinuclidin-3-ylamino)methyl)-1H-indazole-4-carboxylate which was used in the next step without further purification: MS (ESI+) m/z 301 (M+H).

Step C: To a solution of crude lithium (R)-3-((quinuclidin-3-ylamino)methyl)-1H-indazole-4-carboxylate from Step B above in N,N-dimethylformamide (30 mL) was added N,N-diisopropylethylamine (5.7 mL, 34.4 mmol) followed by 1-propanephosphonic acid cyclic anhydride (T3P) (17 mL, 28.65 mmol) at 0° C. for 17 h. The solution was concentrated and purified by column chromatography (silica gel, 70:30:3 dichloromethane/methanol/concentrated ammonium hydroxide), SCX-2 column and preparative TLC (silica gel, 70:30:3 dichloromethane/methanol/concentrated ammonium hydroxide) to afford (R)-7-(quinuclidin-3-yl)-7,8-dihydropyrazolo[3,4,5-de]isoquinolin-6(2H)-one. This material was dissolved in methanol and treated with HCl (1.25 M solution in methanol). The mixture was concentrated under reduced pressure. The residue was lyophilized from water to afford (R)-7-(quinuclidin-3-yl)-7,8-dihydropyrazolo[3,4,5-de]isoquinolin-6(2H)-one (373 mg, 23%) as a light-yellow solid. $^1$H NMR (500 MHz, D$_2$O) δ 7.32 (d, J=8.3 Hz, 1H), 7.26 (dd, J=8.3, 6.9 Hz, 1H), 7.10 (d, J=6.9 Hz, 1H), 4.83 (d, J=17.1 Hz, 1H), 4.71 (d, J=16.8 Hz, 1H), 4.53 (t, J=8.9 Hz, 1H), 3.60 (dd, J=12.9, 10.6 Hz, 1H), 3.33-3.13 (m, 5H), 2.32 (br s, 1H), 2.13-2.07 (m, 1H), 2.03-1.85 (m, 3H). MS (ESI+) m/z 283 (M+H); HPLC>99% (AUC), $t_R$ 10.94 min.

Example 17

Preparation of (R)-2-benzyl-7-(quinuclidin-3-yl)-7,8-dihydropyrazolo[3,4,5-de]isoquinolin-6(2H)-one, hydrochloride salt

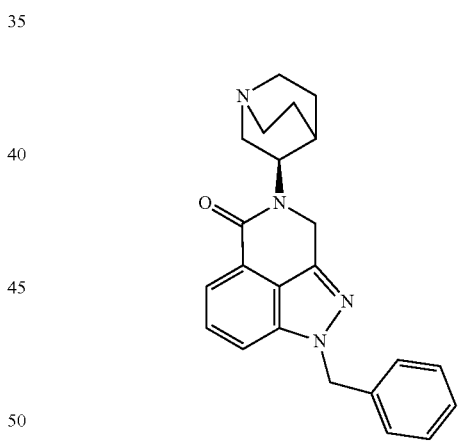

Step A: Following general procedure GP-E1, methyl 3-formyl-1H-indazole-4-carboxylate (B1) and (chloromethyl)benzene were converted to methyl 1-benzyl-3-formyl-1H-indazole-4-carboxylate: MS (ESI+) m/z 295 (M+H).

Step B: Following general procedure GP-F, methyl 1-benzyl-3-formyl-1H-indazole-4-carboxylate and (R)-(+)-3-aminoquinuclidine dihydrochloride were converted to (R)-methyl 1-benzyl-3-((quinuclidin-3-ylamino)methyl)-1H-indazole-4-carboxylate: $^1$H NMR (500 MHz, CDCl$_3$) δ 7.74 (dd, J=3.8, 0.5 Hz, 1H), 7.49 (dd, J=4.5, 0.5 Hz, 1H), 7.33 (dd, J=7.8, 7.5 Hz, 1H), 7.29-7.24 (m, 3H), 7.16 (dd, J=8.0, 0.8 Hz, 2H), 5.59 (m, 3H), 4.31 (d, J=7.0 Hz, 1H), 4.25 (d, J=7.0 Hz, 1H), 3.14-3.07 (m, 1H), 2.91-2.88 (m, 1H), 2.79-2.52 (m, 5H), 2.50 (dq, J=10.0, 2.0 Hz, 2H), 1.96-1.87 (m, 3H), 1.64-1.61 (m, 1H), 1.45-1.32 (m, 2H); MS (ESI+) m/z 405 (M+H).

Step C: Following general procedure GP-G, 1-benzyl-3-((quinuclidin-3-ylamino)methyl)-1H-indazole-4-carboxylate was converted to lithium (R)-1-benzyl-3-((quinuclidin-3-ylamino)methyl)-1H-indazole-4-carboxylate: MS (ESI+) m/z 391 (M+H). Step D: Following general procedure CP-H, lithium (R)-1-benzyl-3-((quinuclidin-3-ylamino)methyl)-1H-indazole-4-carboxylate was converted to (R)-2-benzyl-7-(quinuclidin-3-yl)-7,8-dihydropyrazolo[3,4,5-de]isoquinolin-6(2H)-one, which was immediately treated with hydrochloric acid following general procedure GP-I to give (R)-2-benzyl-7-(quinuclidin-3-yl)-7,8-dihydropyrazolo[3,4,5-de]isoquinolin-6(2H)-one, hydrochloride salt as an off-white solid: $^1$H NMR (500 MHz, CD$_3$OD) δ 7.62 (d, J=4.0 Hz, 1H), 7.56-7.51 (m, 2H), 7.29-7.25 (m, 5H), 5.65 (s, 2H), 5.29 (d, J=8.5 Hz, 1H), 5.19 (d, J=8.5 Hz, 1H), 4.70 (t, J=9.5 Hz, 1H), 3.89-3.78 (m, 2H), 3.68-3.63 (m, 1H), 3.44-3.40 (m, 3H), 2.63 (br s, 1H), 2.44-2.38 (m, 1H), 2.18-2.11 (m, 2H), 2.05 (br s, 1H); MS (ESI+) m/z 373 (M+H); HPLC>99% (AUC), $t_R$ 14.38 min.

Example 18

Preparation of (R)-2-(4-Fluorophenyl)-7-(quinuclidin-3-yl)-7,8-dihydropyrazolo[3,4,5-de]isoquinolin-6(2H)-one, hydrochloride salt

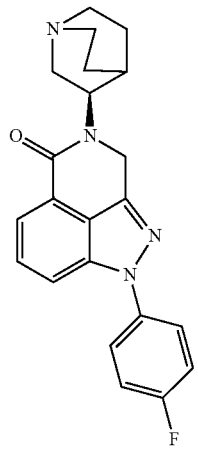 [SMILES: O=C1c2cccc3c2c(nn3-c2ccc(F)cc2)CN1[C@H]1CN2CCC1CC2]

Step A: A mixture of methyl 3-formyl-1H-indazole-4-carboxylate (B1) (3.3 g, 16.1 mmol), 4-fluorophenylboronic acid (4.5 g, 32.3 mmol) and copper(II) acetate (3.99 g, 21.9 mmol) was degassed under nitrogen (3×). Anhydrous dichloromethane (240 ml) and triethylamine (4.5 ml, 13.5 mmol) were added. The mixture was degassed under nitrogen (2×) and stirred at ambient temperature for 21 h. The mixture was concentrated under reduced pressure and the residue was purified by column chromatography (silica gel, 0-30% ethyl acetate in hexanes) to afford methyl 1-(4-fluorophenyl)-3-formyl-1H-indazole-4-carboxylate (454 mg, 9%) as a brown solid. $^1$H NMR (500 MHz, CDCl$_3$) δ 10.38 (s, 1H), 8.01 (d, J=8.3 Hz, 1H), 7.91-7.88 (m, 2H), 7.80 (d, J=7.1 Hz, 1H), 7.69 (dd, J=8.4, 7.3 Hz, 1H), 7.53 (t, J=8.7 Hz, 2H), 3.93 (s, 3H); MS (ESI+) m/z 299 (M+H).

Step B: To a stirred suspension of (R)-(+)-3-aminoquinuclidine dihydrochloride (360 mg, 1.8 mmol) in dichloromethane (15 mL) was added sodium hydride (144 mg, 3.6 mmol) in portions and the mixture was stirred for 1 h. Acetic acid (0.15 mL) was added dropwise. Then methyl 1-(4-fluorophenyl)-3-formyl-1H-indazole-4-carboxylate (454 mg, 1.5 mmol) from Step A above was added and the mixture continued to stir at room temperature for an additional 4 h. Sodium triacetoxyborohydride (1.3 g, 6.0 mmol) was added in one portion and stirring was continued overnight at room temperature. The solvent was removed under reduced pressure and the crude material was purified by column chromatography (silica gel, 90:10:1 dichloromethane/methanol/concentrated ammonium hydroxide) to afford (R)-methyl 1-(4-fluorophenyl)-3-((quinuclidin-3-ylamino)methyl)-1H-indazole-4-carboxylate as a light yellow oil (492 mg, 80%): $^1$H NMR (500 MHz, CDCl$_3$) δ 7.89 (d, J=7.3 Hz, 1H), 7.81 (d, J=8.4 Hz, 1H), 7.63-7.60 (m, 2H), 7.46 (t, J=7.9 Hz, 1H), 7.27-7.24 (m, 2H), 4.37 (d, J=14.1 Hz, 1H), 4.27 (d, J=14.1 Hz, 1H), 4.00 (s, 3H), 3.39-3.34 (m, 1H), 3.22-3.01 (m, 5H), 2.81 (dd, J=13.4, 2.3 Hz, 1H), 2.30-2.25 (m, 1H), 2.20-2.17 (m, 1H), 1.92-1.86 (m, 1H), 1.75-1.69 (m, 1H) 1.63-1.59 (m, 1H); MS (ESI+) m/z 409 (M+H).

Step C: To a solution of (R)-methyl 1-(4-fluorophenyl)-3-((quinuclidin-3-ylamino)methyl)-1H-indazole-4-carboxylate (492 mg, 1.2 mmol) from Step B above in THF (2.5 mL) and H$_2$O (2.5 ml) was added lithium hydroxide monohydrate (152 mg, 3.6 mmol). The mixture was stirred at room temperature overnight and then concentrated under reduced pressure. The residue was dried overnight under vacuum to afford crude lithium (R)-1-(4-fluorophenyl)-3-((quinuclidin-3-ylamino)methyl)-1H-indazole-4-carboxylate which was used in the next step without further purification; MS (ESI+) m/s 394 (M+H).

Step D: A mixture of crude lithium (R)-1-(4-fluorophenyl)-3-((quinuclidin-3-ylamino)methyl)-1H-indazole-4-carboxylate from Step C above and HBTU (688 mg, 1.8 mmol) in N,N-dimethylformamide (5 mL) was stirred at room temperature for 22 h, and then concentrated under reduced pressure. The crude material was filtered through an SCX-2 cartridge. The filtrate was concentrated and purified by column chromatography (silica gel, 90:10:1 dichloromethane/methanol/concentrated ammonium hydroxide) and preparative HPLC to afford (R)-2-(4-fluorophenyl)-7-(quinuclidin-3-yl)-7,8-dihydropyrazolo[3,4,5-de]isoquinolin-6(2H)-one. This material was dissolved in methanol and treated with HCl (1.25M solution in methanol). The mixture was concentrated under reduced pressure. The residue was lyophilized from acetonitrile/water to afford (R)-2-(4-fluorophenyl)-7-(quinuclidin-3-yl)-7,8-dihydropyrazolo[3,4,5-de]isoquinolin-6(2H)-one, hydrochloride salt (83 mg, 16%) as an off-white solid. $^1$H NMR (500 MHz, CD$_3$OD) δ 7.94 (m, 1H), 7.86-7.82 (m, 2H), 7.70-7.66 (m, 2H), 7.36-7.31 (m, 2H), 5.37 (d, J=17.0 Hz, 1H), 5.27 (d, J=17.0 Hz, 1H), 4.76-4.72 (m, 1H), 3.96-3.91 (m, 1H), 3.84 (ddd, J=13.0, 7.7, 1.7 Hz, 1H), 3.71-3.66 (m, 1H), 3.48-3.33 (m, 3H), 2.68-2.66 (m, 1H), 2.48-2.41 (m, 1H), 2.23-2.12 (m, 2H), 2.08-2.02 (m, 1H); MS (ESI+) m/z 299 (M+H); HPLC>99% (AUC), $t_R$ 12.90 min.

Example 19

Preparation of (R)-2-(4-Chlorophenyl)-7-(quinuclidin-3-yl)-7,8-dihydropyrazolo[3,4,5-de]isoquinolin-6(2H)-one, hydrochloride salt

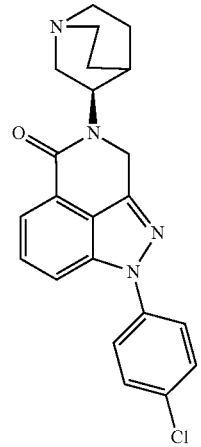 [SMILES: O=C1c2cccc3c2c(nn3-c2ccc(Cl)cc2)CN1[C@H]1CN2CCC1CC2]

Step A: A mixture of (R)-7-(quinuclidin-3-yl)-7,8-dihydropyrazolo[3,4,5-de]isoquinolin-6(2H)-one (100 mg, 0.35 mmol) from Step C of Example 16, 1-chloro-4-iodobenzene (100 mg, 0.42 mmol), copper (I) iodide (3.3 mg, 0.02 mmol), N,N-dimethylcyclohexane-1,2-diamine (11 μL, 0.07 mmol), potassium phosphate tribasic (144 mg, 0.74 mmol) and toluene (1 ml) was placed in a sealed tube and degassed with nitrogen for 2 min. The reaction was heated at 110° C. for 24 h and, after cooling the solution to room temperature, the solvent was evaporated and the residue was purified by preparative TLC (silica gel, 90:10:1 dichloromethane/methanol/concentrated ammonium hydroxide) and preparative HPLC. The resultant compound was then treated with 1.25 M HCl in methanol to afford (R)-2-(4-chlorophenyl)-7-(quinuclidin-3-yl)-7,8-dihydropyrazolo[3,4,5-de]isoquinolin-6(2H)-one, hydrochloride salt (2.5 mg, 2%) as a light yellow solid. $^1$H NMR (500 MHz, D$_2$O) δ 7.52 (d, J=8.5 Hz, 1H), 7.44 (dd, J=8.5, 7.0 Hz, 1H), 7.37 (d, J=7.0 Hz, 1H), 7.20-7.15 (m, 4H), 4.95 (d, J=17.5 Hz, 1H), 4.80 (d, J=18.0 Hz, 1H), 4.65-4.58 (m, 1H), 3.78 (t, J=10.5 Hz, 1H), 3.49-3.43 (m, 2H), 3.33-3.25 (m, 3H), 2.45 (s, 1H), 2.20-2.15 (m, 1H), 2.04-1.94 (m, 3H); MS (ESI+) m/z 393 (M+H); HPLC 98.4% (AUC), t$_R$ 15.66 min.

Example 20

Preparation of (R)-2-(4-Methoxyphenyl)-7-(quinuclidin-3-yl)-7,8-dihydropyrazolo[3,4,5-de]isoquinolin-6(2H)-one, hydrochloride salt

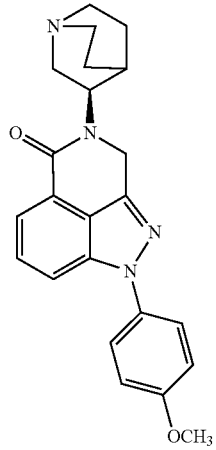 [SMILES: COc1ccc(-n2nc3c4c(cccc42)C(=O)N([C@H]2CN4CCC2CC4)C3)cc1]

Step A: A mixture of (R)-7-(quinuclidin-3-yl)-7,8-dihydropyrazolo[3,4,5-de]isoquinolin-6(2H)-one (150 mg, 0.47 mmol) from Step C of Example 16, 1-bromo-4-methoxybenzene (80 μL, 0.64 mmol), copper(I) iodide (61 mg, 0.32 mmol), L-proline (59 mg, 0.51 mmol), potassium phosphate tribasic (225 mg, 1.06 mmol), N,N'-dimethylethylenediamine (55 μL, 0.51 mmol), 1,4-dioxane (1.5 mL1) and DMSO (1.5 mL) was placed in a sealed tube and degassed with argon for 2 min. Then the sealed tube was closed and heated at 110° C. for 17 h. The solution was cooled to room temperature, extracted with ethyl acetate (3×), washed with water and brine, and dried over saturated sodium sulfate. The filtrate was evaporated and purified by preparative TLC (silica gel, 90:10:1 dichloromethane/methanol/concentrated ammonium hydroxide) and preparative HPLC. The resultant compound was then treated with 1.25 M HCl in methanol to afford (R)-2-(4-methoxyphenyl)-7-(quinuclidin-3-yl)-7,8-dihydropyrazolo[3,4,5-de]isoquinolin-6(2H)-one, hydrochloride salt (5.6 mg, 3%) as a light yellow solid. $^1$H NMR (500 MHz, D$_2$O) δ 7.61 (d, J=8.4 Hz, 1H), 7.51 (dd, J=8.3, 7.1 Hz, 1H), 7.43 (d, J=7.0 Hz, 1H), 7.40 (d, J=8.9 Hz, 2H), 7.01 (d, J=8.9 Hz, 2H), 5.07 (d, J=17.2 Hz, 1H), 4.91 (d, J=17.3 Hz, 1H), 4.76-4.67 (m, 1H), 3.89-3.84 (m, 1H), 3.82 (s, 3H), 3.57-3.50 (m, 2H), 3.44-3.30 (m, 3H), 2.50 (br s, 1H), 2.25-2.21 (m, 1H), 2.17-2.10 (m, 3H); MS (ESI+) m/z 389 (M+H); HPLC>99% (AUC), t$_R$ 14.42 min.

Example 21

Preparation of (R)-4-Bromo-7-(quinuclidin-3-yl)-7,8-dihydropyrazolo[3,4,5-de]isoquinolin-6(2H)-one, hydrochloride salt

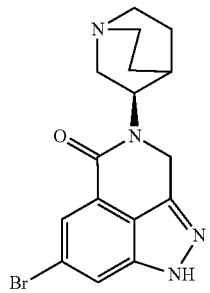 [SMILES: O=C1c2cc(Br)cc3[nH]nc(c23)CN1[C@H]1CN2CCC1CC2]

Step A: Following the procedure in Step A of Example 11, methyl 6-bromo-3-formyl-1H-indazole-4-carboxylate was converted to a mixture of regioisomeric products: methyl 6-bromo-3-formyl-2((2-(trimethylsilyl)ethoxy)methyl)-2H-indazole-4-carboxylate (0.61 g, 39%) as a yellow solid: $^1$H NMR (300 MHz, CDCl$_3$) δ 10.86 (s, 1H), 8.26 (d, J=2.0 Hz, 1H), 8.20 (d, J=2.0 Hz, 1H), 6.18 (s, 2H), 4.01 (s, 3H), 3.71 (dd, J=8.5, 7.5, 2H), 0.93 (dd, J=8.5, 7.5 Hz, 2H), −0.02 (9H, s) and methyl 6-bromo-3-formyl-1-((2-(trimethylsilyl)ethoxy)methyl)-1H-indazole-4-carboxylate (0.60 g, 38%) as a yellow solid: $^1$H NMR (300 MHz, CDCl$_3$) δ 10.47 (s, 1H), 8.04 (d, J=2.0 Hz, 1H), 7.92 (dd, J=2.0 Hz, 1H), 5.83 (s, 2H), 4.03 (s, 3H), 3.57 (dd, J=8.5, 7.5, 2H), 0.91 (dd, J=8.5, 7.5 Hz, 2H), −0.03 (s, 9H).

Step B: Following general procedure GP-F, except that dioxane was used as solvent and sodium hydride was used as base, methyl 6-bromo-3-formyl-1-((2-(trimethylsilyl)ethoxy)methyl)-1H-indazole-4-carboxylate (0.60 g, 1.45 mmol) was converted to (R)-methyl 6-bromo-3-((quinuclidin-3-ylamino)methyl)-1((2-(trimethylsilyl)ethoxy)methyl)-1H-indazole-4-carboxylate (0.49 g, 64%): $^1$H NMR (500 MHz, CDCl$_3$) δ 7.92 (s, 1H), 7.89 (s, 1H), 5.67 (s, 2H), 4.27-4.18 (m, 2H), 3.99 (s, 3H), 3.55 (dd, J=8.0, 8.0 Hz, 2H), 3.16-3.10 (m, 1H), 2.98-2.70 (m, 5H), 2.56-2.50 (m, 1H), 2.00-1.90 (m, 3H), 1.72-1.64 (m, 1H), 1.50-1.44 (m, 1H), 1.40-1.32 (m, 1H), 0.90 (dd, J=8.0, 8.0 Hz, 2H), −0.04 (s, 9H); MS (ESI+) m/z 525 (M+H)$^+$.

Step C: Following general procedure GP-G, (R)-methyl 6-bromo-3-((quinuclidin-3-ylamino)methyl)-1-((2-(trimethylsilyl)ethoxy)methyl)-1H-indazole-4-carboxylate was converted to crude lithium (R)-6-bromo-3-((quinuclidin-3-ylamino)methyl)-1-((2-(trimethylsilyl)ethoxy)methyl)-1H-indazole-4-carboxylate; MS (ESI) m/z 509 (acid M+H)$^+$.

Step D: To a sealed tube containing a solution of crude lithium (R)-6-bromo-3-((quinuclidin-3-ylamino)methyl)-1-

((2-(trimethylsilyl)ethoxy)methyl)-1H-indazole-4-carboxylate 0.40 g, 0.90 mmol) in 2-propanol (40 mL) was added 6N HCl (4 mL). The reaction mixture was flushed with argon, sealed and heated to 140° C. for 30 min, cooled to ambient temperature and concentrated under reduced pressure. The residue was concentrated and purified by reverse phase semi-preparative HPLC (5-20% acetonitrile in water—both eluents contained 0.05% trifluoroacetic acid as modifier). The solvents were removed in vacuo and the desired product trifluoracetate salt was purified further by preparative TLC (6:3:1 dichloromethane/methanol/concentrated ammonium hydroxide) to afford (R)-6-bromo-3-((quinuclidin-3-ylamino)methyl)-1H-indazole-4-carboxylic acid (119 mg, 40%) as an amorphous white solid: $^1$H NMR (500 MHz, $d_4$-MeOH) δ, 7.74 (d, J=1.5 Hz, 1H), 7.66 (d, J=1.5 Hz, 1H), 4.40-4.28 (m, 2H), 3.60-3.30 (m, 3H), 3.22-3.00 (m, 5H), 2.26-2.20 (m, 1H), 2.19-2.02 (m, 1H), 2.00-1.90 (m, 1H) 1.88-1.68 (m, 2H).

Step E: Following the procedure in Step C of Example 16 for the cyclization and general procedure GP-I for the hydrochloride salt formation, (R)-6-bromo-3-((quinuclidin-3-ylamino)methyl)-1H-indazole-4-carboxylic acid was converted to (R)-4-bromo-7-(quinuclidin-3-yl)-7,8-dihydropyrazolo[3,4,5-de]isoquinolin-6(2H)-one, hydrochloride salt (42 mg, 38%) as an amorphous white solid: $^1$H NMR (500 MHz, $d_4$-MeOH) δ 7.86 (d, J=1.0 Hz, 1H), 7.64 (s, 1H), 5.33-5.17 (m, 2H), 4.71 (t, J=9.5 Hz, 1H), 3.74-3.56 (m, 3H), 3.48-3.30 (m, 3H), 2.62-2.58 (m, 1H), 2.44-2.32 (m, 1H), 2.20-2.08 (m, 2H), 2.06-1.94 (m, 1H); MS (ESI+) m/z 362 (M+H)$^+$; HPLC>99.0% (AUC), $t_R$ 10.25 min.

Example 22

Preparation of 7-(Endo-N-(9-methyl-9-azabicyclo [3.3.1]nonan-3-yl))-2-methyl-7,8-dihydropyrazolo[3,4,5-de]isoquinolin-6(2H)-one, hydrochloride salt

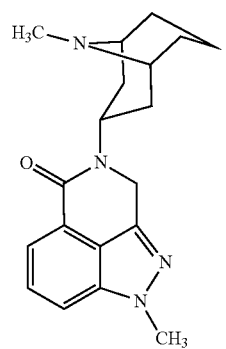 [SMILES: CN1C2CCCC1CC(N1Cc3nn(C)c4cccc(c34)C1=O)C2]

Step A: Following general procedure GP-F, endo-9-methyl-9-azabicyclo[3.3.1]nonan-3-amine dihydrochloride and methyl 3-formyl-1-methyl-1H-indazole-4-carboxylate were converted to methyl 1-methyl-3-[(9-methyl-9-azabicyclo [3.3.1]nonan-3-ylamino)methyl]-1H-indazole-4-carboxylate: $^1$H NMR (500 MHz, CDCl$_3$) δ 7.78 (d, J=7.2 Hz, 1H), 7.55 (d, J=8.8 Hz, 1H), 7.50 (t, J=7.5 Hz, 1H), 4.33 (s, 1H), 4.06 (s, 3H), 3.98 (s, 3H), 3.30-3.19 (m, 1H), 3.18-3.08 (m, 2H), 3.06-2.97 (m, 1H), 2.64-2.47 (m, 5H), 2.42-2.32 (m, 1H), 2.07-1.82 (m, 2H), 1.53-1.35 (m, 3H), 1.23-1.06 (m, 2H), 1.05-0.94 (m, 1H); MS (APCI+) m/z 357 (M+H).

Step B: Following general procedure GP-G, methyl 1-methyl-3-[(9-methyl-9-azabicyclo[3.3.1]nonan-3-ylamino)methyl]-1H-indazole-4-carboxylate was converted to lithium 1-methyl-3-[(9-methyl-9-azabicyclo[3.3.1]nonan-3-ylamino)methyl]-1H-indazole-4-carboxylate: MS (ESI) m/z 343 (M+H).

Step C: Following general procedure GP-H, lithium 1-methyl-3-[(9-methyl-9-azabicyclo[3.3.1]nonan-3-ylamino)methyl]-1H-indazole-4-carboxylate was converted to 7-(endo-N-(9-methyl-9-azabicyclo[3.3.1]nonan-3-yl))-2-methyl-7,8-dihydropyrazolo[3,4,5-de]isoquinolin-6(2H)-one, which was immediately treated with hydrochloric acid following general procedure GP-I to give 7-(endo-N-(9-methyl-9-azabicyclo[3.3.1]nonan-3-yl))-2-methyl-7,8-dihydropyrazolo[3,4,5-de]isoquinolin-6(2H)-one, hydrochloride salt: $^1$H NMR (500 MHz, DMSO-$d_6$) δ 9.44 (s, 1H), 7.75 (d, J=8.2 Hz, 1H), 7.53 (t, J=7.9 Hz, 1H), 7.45 (d, J=6.8 Hz 1H), 5.19-5.15 (m, 1H), 5.09 (s, 2H), 4.08 (m, 3H), 3.84-3.76 (m, 0.2H), 3.75-3.66 (m, 1.8H), 2.97 (d, J=4.8 Hz, 0.2H), 2.84 (d, J=6.8 Hz, 2.8H), 2.33-2.22 (m, 5H), 2.15-2.00 (m 2H), 1.72-1.38 (m, 3H); MS (ESI+) m/z 325 (M+H); HPLC 98.9% (AUC), $t_R$ 13.55 min.

Example 23

Preparation of (S)-7-(quinuclidin-3-yl)-8,9-dihydro-2H-azepino[5,4,3-cd]indazol-6(7H)-one, hydrochloride salt

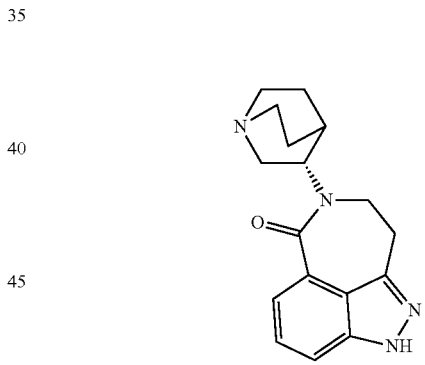

Step A: Following the procedure in Example 2, methyl 3-formyl-1H-indazole-4-carboxylate (B1) and benzyl bromide were converted to methyl 1-benzyl-3-formyl-1H-indazole-4-carboxylate (3.75 g, 48%): $^1$H NMR (300 MHz, CDCl$_3$) δ 10.54 (s, 1H), 7.78 (dd, J=7.5, 1.0 Hz, 1H), 7.46 (dd, J=8.7, 1.2 Hz, 1H), 7.46-7.41 (m, 1H), 7.40-7.29 (m, 3H), 7.25-7.20 (m, 2H), 5.74 (s, 2H), 3.98 (s, 3H); MS (ESI+) m/z 267 (M+H).

Step B: Following general procedure GP-J, methyl 1-benzyl-3-formyl-1H-indazole-4-carboxylate (3.75 g, 12.76 mmol) was converted to methyl 1-benzyl-3-(2-oxoethyl)-1H-indazole-4-carboxylate (2.79 g, 71%): $^1$H NMR (300 MHz, CDCl₃) δ 9.92 (s, 1H), 7.83 (dd, J=7.5, 1.0 Hz, 1H), 7.53 (dd, J=8.7, 1.0 Hz, 1H), 7.38-7.32 (m, 1H), 7.30-7.27 (m, 3H), 7.17-7.14 (m, 2H), 5.61 (s, 2H), 4.37 (s, 2H), 3.97 (s, 3H); MS (ESI+) m/z 309 (M+H).

Step C: Following general procedure GP-K, (S)-(−)-3-aminoquinuclidine dihydrochloride (531 mg, 2.67 mmol) and methyl 1-benzyl-3-(2-oxoethyl)-1H-indazole-4-carboxylate (1.37 g, 4.45 mmol) were converted to (S)-methyl 1-benzyl-3-(2-(quinuclidin-3-ylamino)ethyl)-1H-indazole-4-carboxylate (520 mg, 46%) as a pink solid: ¹H NMR (300 MHz, CDCl₃) δ 7.70 (dd, J=7.0, 0.5 Hz, 1H), 7.49 (dd, J=8.5, 0.5 Hz, 1H), 7.34-7.31 (m, 1H), 7.29-7.22 (m, 3H), 7.14-7.12 (m, 2H), 5.57 (s, 2H), 3.97 (s, 3H), 3.14-3.09 (m, 1H), 3.06-3.01 (m, 1H), 2.96-2.91 (m, 1H), 2.84-2.79 (m, 5H), 2.42-2.38 (m, 1H), 2.02 (s, 2H), 1.83-1.76 (m, 2H), 1.68-1.62 (M, 1H), 1.49-1.43 (m, 1H), 1.31-1.25 (m, 1H); MS (ESI+) m/z 419 (M+H)

Step D: Following general procedure GP-L, (S)-methyl 1-benzyl-3-(2-(quinuclidin-3-ylamino)ethyl)-1H-indazole-4-carboxylate (520 mg, 1.24 mmol) and lithium hydroxide monohydrate (129 mg, 3.07 mmol) were converted lithium (S)-1-benzyl-3-(2-(quinuclidin-3-ylamino)ethyl)-1H-indazole-4-carboxylate (509 mg, quant. yield), which was used in the next step without further purification: MS (ESI+) m/z 405 (M+H).

Step E: To a solution of the crude lithium (S)-1-benzyl-3-(2-(quinuclidin-3-ylamino)ethyl)-1H-indazole-4-carboxylate (509 mg, 1.24 mmol) from Step D above in DMF (25 mL) was added N,N-diisopropylethylamine (1.22 mL, 7.44 mmol) at 0° C. To the above reaction was added 1-propanephosphonic acid cyclic anhydride (T3P) (50% in ethyl acetate, 3.94 g, 6.2 mmol) and the mixture was stirred at 0° C. for 1.5 h. The reaction mixture was treated with brine (25 mL) and saturated aqueous solution of sodium bicarbonate (25 mL). The compound was extracted with dichloromethane (4×100 mL) and the combined organic layers were washed with brine, dried (Na₂SO₄), filtered, and concentrated under reduced pressure. The crude material was purified by column chromatography (silica gel, 90:9:1 dichloromethane/methanol/concentrated ammonium hydroxide) to afford (S)-2-benzyl-7-(quinuclidin-3-yl)-8,9-dihydro-2H-azepino[5,4,3-cd]indazol-6(7H)-one (316 mg, 66%) as a white solid: ¹H NMR (300 MHz, CDCl₃) δ 7.98-7.95 (m, 1H), 7.45-7.43 (m, 2H), 7.32-7.25 (m, 3H), 7.119-7.15 (m, 2H), 5.57 (s, 2H), 4.85-4.68 (1H), 4.20-3.90 (m, 2H), 3.45-3.38 (m, 1H), 3.35-2.90 (m, 7H), 2.25-2.15 (m, 1H), 1.95-1.55 (m, 4H); MS (ESI+) m/z 387 (M+H).

Step F: Following general procedure GP-U, (S)-2-benzyl-7-(quinuclidin-3-yl)-8,9-dihydro-2H-azepino[5,4,3-cd]indazol-6(7H)-one was converted to (S)-7-(quinuclidin-3-yl)-8,9-dihydro-2H-azepino[5,4,3-cd]indazol-6(7H)-one: MS (ESI+) m/z 297 (M+H).

Step G: Following general procedure GP-N, (S)-7-(quinuclidin-3-yl)-8,9-dihydro-2H-azepino[5,4,3-cd]indazol-6(7H)-one was converted to (S)-7-(quinuclidin-3-yl)-8,9-dihydro-2H-azepino[5,4,3-cd]indazol-6(7H)-one, hydrochloride salt: ¹H NMR (500 MHz, DMSO-d₆) δ 13.08 (bs, 1H), 10.36 (bs 1H), 7.78 (d, J=7.0 Hz, 1H), 7.70 (d, J=8.5 Hz, 1H), 7.48 (t, J=8.0 Hz, 1H), 4.70 (m, 1H), 4.10-3.35 (m, 5H), 3.30-3.05 (m, 5H), 2.90-2.85 (m, 1H), 2.10-1.80 (m, 4H): MS (ESI+) m/z 297 (M+H); HPLC>99.0% (AUC), t_R 10.99 min.

Example 24

Preparation of (S)-2-Methyl-7-(quinuclidin-3-yl)-8,9-dihydro-2H-azepino[5,4,3-cd]indazol-6(7H)-one, hydrochloride salt

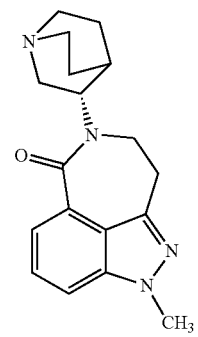 [SMILES: Cn1nc2c3c(cccc31)C(=O)N([C@@H]1CN3CCC1CC3)CC2]

Step A: Following general procedure GP-J, methyl 3-formyl-1-methyl-1H-indazole-4-carboxylate (B1) was converted to methyl 1-methyl-3-(2-oxoethyl)-1H-indazole-4-carboxylate: ¹H NMR (500 MHz, CDCl₃) δ 9.90 (s, 1H), 7.90 (dd, J=7.3 Hz, 1H), 7.69 (m, 1H), 7.45 (m, 1H), 4.31 (s, 2H), 4.10 (s, 3H), 3.91 (s, 3H).

Step B: Following general procedure GP-K, (S)-(−)-3-aminoquinuclidine dihydrochloride and methyl 1-methyl-3-(2-oxoethyl)-1H-indazole-4-carboxylate were converted to (S)-methyl 1-methyl-3-(2-(quinuclidin-3-ylamino)ethyl)-1H-indazole-4-carboxylate (723 mg, 64%) as a yellow solid: ¹H NMR (300 MHz, DMSO-d₆) δ 9.65 (bs, 1H), 7.83 (d, J=7.3 Hz, 1H), 7.80 (d, J=7.2 Hz, 1H), 7.51 (t, J=7.2 Hz, 1H), 4.71 (m, 1H), 4.10 (s, 3H), 3.91-3.43 (m, 4H); MS (ESI+) m/z 343 (M+H).

Step C: Following general procedure GP-L, (S)-methyl 1-methyl-3-(2-(quinuclidin-3-ylamino)ethyl)-1H-indazole-4-carboxylate was converted to lithium (S)-1-methyl-3-(2-(quinuclidin-3-ylamino)ethyl)-1H-indazole-4-carboxylate: MS (ESI+) m/z 329 (M+H).

Step D: Following general procedure GP-M, lithium (S)-1-methyl-3-(2-(quinuclidin-3-ylamino)ethyl)-1H-indazole-4-carboxylate was converted to (S)-2-methyl-7-(quinuclidin-3-yl)-8,9-dihydro-2H-azepino[5,4,3-cd]indazol-6(7H)-one: ¹H NMR (500 MHz, DMSO-d₆) δ 7.85 (m, 2H), 7.55 (t, J=7.3 Hz, 1H), 4.66 (m, 1H), 4.12 (m, 1H), 4.09 (s, 3H), 3.89-3.60, 3.55 (m, 2H), 3.32 (m, 2H), 3.16 (m, 1H), 3.09 (m, 1H), 3.00 (m, 1H), 2.81 (m, 2H), 2.10-2.03 (m, 2H), 1.80-1.61 (m, 2H), 1.45 (m, 1H); MS (ESI+) m/z 311 (M+H).

Step E: Following general procedure GP-N, (S)-2-methyl-7-(quinuclidin-3-yl)-8,9-dihydro-2H-azepino[5,4,3-cd]indazol-6(7H)-one was converted to (S)-2-methyl-7-(quinuclidin-3-yl)-8,9-dihydro-2H-azepino[5,4,3-cd]indazol-6(7H)-one, hydrochloride salt: ¹H NMR (500 MHz, DMSO-d₆) δ 10.54 (bs, 1H), 7.84 (d, J=7.3 Hz, 1H), 7.79 (d, J=7.3 Hz, 1H), 7.53 (t, J=7.4 Hz, 1H), 4.71 (m, 1H), 4.03 (s, 3H), 3.98-3.39

(m 5H), 3.30 (m, 3H), 3.20-3.05 (m, 2H), 2.51-2.34 (m, 1H), 2.01-1.79 (m, 4H); MS (ESI+) m/z 311 (M+H); HPLC>99% (AUC), $t_R$ 8.32 min.

Example 25

Preparation of (S)-2-Ethyl-7-(quinuclidin-3-yl)-8,9-dihydro-2H-azepino[5,4,3-cd]indazol-6(7H)-one, hydrochloride salt

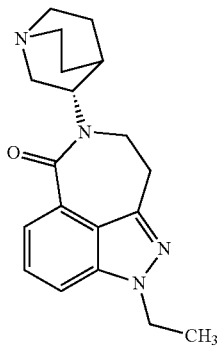 [SMILES: CCn1nc2c3c(cccc31)C(=O)N([C@@H]1CN3CCC1CC3)CC2]

Step A: Following general procedure GP-J, methyl 3-formyl-1-ethyl-1H-indazole-4-carboxylate was converted to methyl 1-ethyl-3-(2-oxoethyl)-1H-indazole-4-carboxylate: $^1$H NMR (500 MHz, CDCl$_3$) δ 9.90 (s, 1H), 7.84 (d, J=7.4 Hz, 1H), 7.62 (d, J=7.3 Hz, 1H), 7.41 (t, J=7.4 Hz, 1H), 4.46 (q, 2H), 4.32 (s, 2H), 3.97 (s, 3H), 1.57 (t, 3H).

Step B: Following general procedure GP-K, (S)-(−)-3-aminoquinuclidine dihydrochloride and methyl 1-ethyl-3-(2-oxoethyl)-1H-indazole-4-carboxylate were converted to (S)-methyl 1-ethyl-3-(2-(quinuclidin-3-ylamino)ethyl)-1H-indazole-4-carboxylate: $^1$H NMR (500 MHz, CDCl$_3$) δ 7.72 (d, J=7.3 Hz, 1H), 7.56 (d, J=7.2 Hz, 1H), 7.37 (t, J=7.2 Hz, 1H), 4.42 (q, 2H), 3.96 (s, 3H), 3.33 (m, 2H), 3.21 (m, 1H), 3.00 (m, 5H), 2.63 (m, 1H), 2.01 (m, 2H), 1.81 (m, 1H), 1.67 (m, 1H), 1.43 (t, 3H); MS (ESI+) m/z 357 (M+H).

Step C: Following general procedure GP-L, (S)-methyl 1-ethyl-3-(2-(quinuclidin-3-ylamino)ethyl)-1H-indazole-4-carboxylate was converted to lithium (S)-1-ethyl-3-(2-(quinuclidin-3-ylamino)ethyl)-1H-indazole-4-carboxylate: $^1$H NMR (500 MHz, DMSO-d$_6$) δ 8.49 (s, 1H), 7.35 (d, J=7.3 Hz, 1H), 7.19 (t, J=7.2 Hz, 1H), 7.08 (d, J=7.2 Hz, 1H), 4.31 (q, 2H), 3.23 (m, 2H), 2.90-2.50 (m, 5H), 1.81-1.49 (m, 5H), 1.30 (t, 3H), 1.14 (m, 1H); MS (ESI+) m/z 342 (M+H).

Step D: Following general procedure GP-M, lithium (S)-1-ethyl-3-(2-(quinuclidin-3-ylamino)ethyl)-1H-indazole-4-carboxylate was converted to (S)-2-ethyl-7-(quinuclidin-3-yl)-8,9-dihydro-2H-azepino[5,4,3-cd]indazol-6(7H)-one: $^1$H NMR (500 MHz, DMSO-d$_6$) δ 7.87 (d, J=7.3 Hz, 1H), 7.75 (d, J=7.4 Hz, 1H), 7.47 (t, J=7.2 Hz, 1H), 4.66 (m, 1H), 4.45 (q, J=7.1 Hz, 2H), 4.12 (m, 1H), 3.89-3.60, 3.55 (m, 2H), 3.32 (m, 2H), 3.16 (m, 1H), 3.09 (m, 1H), 3.00 (m, 1H), 2.81 (m, 2H), 2.10-2.03 (m, 2H), 1.80-1.61 (m, 2H), 1.45 (m, 1H), 1.38 (t, J=7.2 Hz, 3H); (MS (ESI+) m/z 325 (M+H).

Step E: Following general procedure GP-N, (S)-2-ethyl-7-(quinuclidin-3-yl)-8,9-dihydro-2H-azepino[5,4,3-cd]indazol-6(7H)-one was converted to (S)-2-ethyl-7-(quinuclidin-3-yl)-8,9-dihydro-2H-azepino[5,4,3-cd]indazol-6(7H)-one, hydrochloride salt: $^1$H NMR (500 MHz, DMSO-d$_6$) δ 10.24 (bs, 1H), 7.87 (d, J=7.3 Hz, 1H), 7.80 (d, J=7.4 Hz, 1H), 7.53 (t, J=7.2 Hz, 1H), 4.69 (m, 1H), 4.45 (q, J=7.1 Hz, 2H), 4.12 (m, 1H), 3.89-3.60 (m, 2H), 3.55 (m, 2H), 3.32 (m, 2H), 3.16 (m, 1H), 3.09 (m, 1H), 3.00 (m, 1H), 2.39-2.35 (m, 1H), 2.10-2.03 (m, 2H), 1.80-1.61 (m, 2H), 1.38 (t, J=7.2 Hz, 3H); MS (ESI+) m/z 325 (M+H); HPLC>99% (AUC), $t_R$ 8.78 min.

Example 26

Preparation of (S)-2-Isopropyl-7-(quinuclidin-3-yl)-8,9-dihydro-2H-azepino[5,4,3-cd]indazol-6(7H)-one, hydrochloride salt

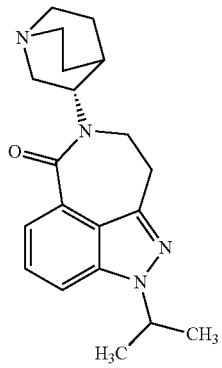 [SMILES: CC(C)n1nc2c3c(cccc31)C(=O)N([C@@H]1CN3CCC1CC3)CC2]

Step A: Following general procedure GP-J, methyl 3-formyl-1-isopropyl-1H-indazole-4-carboxylate was converted to methyl 1-isopropyl-3-(2-oxoethyl)-1H-indazole-4-carboxylate: $^1$H NMR (500 MHz, CDCl$_3$) δ 9.90 (s, 1H), 7.82 (d, J=7.4 Hz, 1H), 7.64 (d, J=7.3 Hz, 1H), 7.43 (t, J=7.4 Hz, 1H), 4.84 (m, 1H), 4.32 (s, 2H), 3.97 (s, 3H), 1.65 (d, 6H).

Step B: Following general procedure GP-K, (S)-(−)-3-aminoquinuclidine dihydrochloride and methyl 1-isopropyl-3-(2-oxoethyl)-1H-indazole-4-carboxylate were converted to (S)-methyl 1-isopropyl-3-(2-(quinuclidin-3-ylamino)ethyl)-1H-indazole-4-carboxylate: $^1$H NMR (500 MHz, CDCl$_3$) δ 7.73 (d, J=7.3 Hz, 1H), 7.60 (d, J=7.2 Hz, 1H), 7.37 (t, J=7.2 Hz, 1H), 4.83 (m, 1H), 3.97 (s, 3H), 3.50-2.90 (m, 8H), 2.31 (m, 2H), 2.01 (m, 1H), 1.88 (m, 1H), 1.71 (m, 1H), 1.55 (d, 6H); MS (ESI+) m/z 343 (M+H).

Step C: Following general procedure GP-L, (S)-methyl 1-isopropyl-3-(2-(quinuclidin-3-ylamino)ethyl)-1H-indazole-4-carboxylate was converted to lithium (S)-1-isopropyl-3-(2-(quinuclidin-3-ylamino)ethyl)-1H-indazole-4-carboxylate: $^1$H NMR (500 MHz, DMSO-d$_6$) δ 8.50 (s, 1H), 7.37 (d, J=7.3 Hz, 1H), 7.16 (t, J=7.2 Hz, 1H), 7.09 (d, J=7.2 Hz, 1H), 4.85 (m, 1H), 3.23 (m, 2H), 2.90-2.50 (m, 5H), 1.81-1.49 (m, 4H), 1.50 (d, 6H), 1.43 (m, 1H), 1.14 (m, 1H); MS (ESI+) m/z 329 (M+H).

Step D: Following general procedure GP-M, lithium (S)-1-isopropyl-3-(2-(quinuclidin-3-ylamino)ethyl)-1H-indazole-4-carboxylate was converted to (S)-2-isopropyl-7-(quinuclidin-3-yl)-8,9-dihydro-2H-azepino[5,4,3-cd]indazol-6(7H)-one: $^1$H NMR (500 MHz, DMSO-d$_6$) δ 7.84 (d, J=7.5 Hz, 1H), 7.76 (d, J=7.4 Hz, 1H), 7.49 (t, J=7.2 Hz, 1H), 5.00 (m, 1H), 4.66 (m, 1H), 4.12-3.10 (m, 8H), 2.31 (m, 2H), 2.10-1.78 (m, 5H), 1.48 (m, 6H); MS (ESI+) m/z 339 (M+H).

Step E: Following general procedure GP-N, (S)-2-isopropyl-7-(quinuclidin-3-yl)-8,9-dihydro-2H-azepino[5,4,3-cd]indazol-6(7H)-one was converted to (S)-2-isopropyl-7-(quinuclidin-3-yl)-8,9-dihydro-2H-azepino[5,4,3-cd]indazol-6(7H)-one, hydrochloride salt: $^1$H NMR (500 MHz, DMSO-d$_6$) δ 10.39 (bs, 1H), 7.91 (d, J=7.5 Hz, 1H), 7.87 (d, J=7.4 Hz, 1H), 7.55 (t, J=7.2 Hz, 1H), 5.00 (m, 1H), 4.66 (m, 1H), 4.12-3.10 (m, 8H), 2.31 (m, 2H), 2.10-1.78 (m, 5H), 1.48 (m, 6H); (MS (ESI+) m/z 339 (M+H); HPLC>99% (AUC), $t_R$ 9.25 min.

Example 27

Preparation of (S)-2-benzyl-7-(quinuclidin-3-yl)-8,9-dihydro-2H-azepino[5,4,3-cd]indazol-6(7H)-one, hydrochloride salt

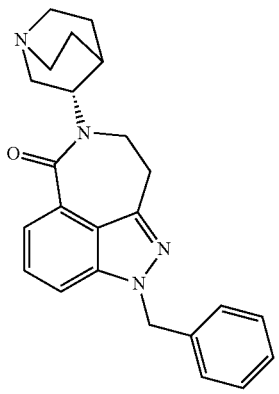 [SMILES: O=C1c2cccc3c2c(nn3Cc2ccccc2)CCN1[C@@H]1CN2CCC1CC2]

Step A: Following general procedure GP-E1, methyl 3-formyl-1H-indazole-4-carboxylate (B1) and benzyl bromide were converted to methyl 1-benzyl-3-formyl-1H-indazole-4-carboxylate (375 g, 48%).: $^1$H NMR (300 MHz, CDCl$_3$) δ 10.54 (s, 1H), 7.78 (dd, J=7.5, 1.0 Hz, 1H), 7.46 (dd, J=8.7, 1.2 Hz, 1H), 7.46-7.41 (m, 1H), 7.40-7.29 (m, 3H), 7.25-7.20 (m, 2H), 5.74 (s, 2H), 3.98 (s, 3H): MS (ESI+) m/z 267 (M+H).

Step B: Following general procedure GP-J, methyl 1-benzyl-3-formyl-1H-indazole-4-carboxylate (3.75 g, 12.76 mmol) was converted to methyl 1-benzyl-3-(2-oxoethyl)-1H-indazole-4-carboxylate (2.79 g, 71%): $^1$H NMR (300 MHz, CDCl$_3$) δ 9.92 (s, 1H), 7.83 (dd, J=7.5, 1.0 Hz, 1H), 7.53 (dd, J=8.7, 1.0 Hz, 1H), 7.38-7.32 (m, 1H), 7.30-7.27 (m, 3H), 7.17-7.14 (m, 2H), 5.61 (s, 2H), 4.37 (s, 2H), 3.97 (s, 3H); MS (ESI+) m/z 309 (M+H).

Step C: Following general procedure GP-K, (S)-(−)-3-aminoquinuclidine dihydrochloride (531 mg, 2.67 mmol) and methyl 1-benzyl-3-(2-oxoethyl)-1H-indazole-4-carboxylate (1.37 g, 4.45 mmol) were converted to (S)-methyl 1-benzyl-3-(2-(quinuclidin-3-ylamino)ethyl)-1H-indazole-4-carboxylate (520 mg, 46%) as a pink solid: $^1$H NMR (300 MHz, CDCl$_3$) δ 7.70 (dd, J=7.0, 0.5 Hz, 1H), 7.49 (dd, J=8.5, 0.5 Hz, 1H), 7.34-7.31 (m, 1H), 7.29-7.22 (m, 3H), 7.14-7.12 (m, 2H), 5.57 (s, 2H), 3.97 (s, 3H), 3.14-3.09 (m, 1H), 3.06-3.01 (m, 1H), 2.96-2.91 (m, 1H), 2.84-2.79 (m, 5H), 2.42-2.38 (m, 1H), 2.02 (s, 2H), 1.83-1.76 (m, 2H), 1.68-1.62 (M, 1H), 1.49-1.43 (m, 1H), 1.31-1.25 (m, 1H); MS (ESI+) m/z 419 (M+H).

Step D: Following general procedure GP-L, (S)-methyl 1-benzyl-3-(2-(quinuclidin-3-ylamino)ethyl)-1H-indazole-4-carboxylate (520 mg, 1.24 mmol) and lithium hydroxide monohydrate (129 mg, 3.07 mmol) were converted lithium (S)-1-benzyl-3-(2-(quinuclidin-3-ylamino)ethyl)-1H-indazole-4-carboxylate (509 mg, quant. yield) which was used in the next step without further purification: MS (ESI+) m/z 405 (M+H).

Step E: To a solution of the crude lithium (S)-1-benzyl-3-(2-(quinuclidin-3-ylamino)ethyl)-1H-indazole-4-carboxylate (509 mg, 1.24 mmol) from Step D above in DMF (25 mL) was added N,N-diisopropylethylamine (1.22 mL, 7.44 mmol) at 0° C. To the above reaction was added 1-propanephosphonic acid cyclic anhydride (T3P) (50% in ethyl acetate, 3.94 g, 6.2 mmol) and the mixture was stirred at 0° C. ambient temperature for 1.5 h. The reaction mixture was treated with brine (25 mL) and saturated aqueous solution of sodium bicarbonate (25 mL). The compound was extracted with dichloromethane (4×100 mL) and the combined organic layers were washed with brine, dried (Na$_2$SO$_4$), filtered, and concentrated under reduced pressure the crude material purified by column chromatography (silica gel, 90:9:1 dichloromethane/methanol/concentrated ammonium hydroxide) to afford (S)-2-benzyl-7-(quinuclidin-3-yl)-8,9-dihydro-2H-azepino[5,4,3-cd]indazol-6(7H)-one (316 mg, 66%) as a white solid: $^1$H NMR (300 MHz, CDCl$_3$) δ 7.98-7.95 (m, 1H), 7.45-7.43 (m, 2H), 7.32-7.25 (m, 3H), 7.119-7.15 (m, 2H), 5.57 (s, 2H), 4.85-4.68 (1H), 4.20-3.90 (m, 2H), 3.45-3.38 (m, 1H), 3.35-2.90 (m, 7H), 2.25-2.15 (m, 1H), 1.95-1.55 (m, 4H); MS (ESI+) m/z 387 (M+H).

Step F: Following general procedure GP-N, (S)-2-benzyl-7-(quinuclidin-3-yl)-8,9-dihydro-2H-azepino[5,4,3-cd]indazol-6(7H)-one (75 mg, 0.194 mmol) was converted to (S)-2-benzyl-7-(quinuclidin-3-yl)-8,9-dihydro-2H-azepino[5,4,3-cd]indazol-6(7H)-one, hydrochloride salt (35 mg, 43%): $^1$H NMR (500 MHz, DMSO-d$_6$) δ 10.51 (bs, 1H), 7.74 (d, J=7.5 Hz, 1H), 7.66 (d, J=8.0 Hz, 1H), 7.47 (s, 1H), 7.93 (t, J=7.5 Hz, 2H), 7.25-7.19 (m, 3H), 5.42 (s, 2H), 4.71 (m, 1H), 4.10-3.31 (m, 5H), 3.26-3.15 (m, 3H), 3.10-2.80 (m, 2H), 2.35-2.20 (m, 1H), 2.10-1.85 (m, 4H); MS (ESI+) m/z 386 (M+H); HPLC 98.8% (AUC), $t_R$ 14.22 min.

Example 28

Preparation of (R)-7-(quinuclidin-3-yl)-8,9-dihydro-2H-azepino[5,4,3-cd]indazol-6(7H)-one, hydrochloride salt

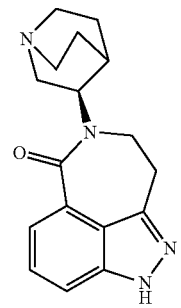 [SMILES: O=C1c2cccc3[nH]nc(c23)CCN1[C@H]1CN2CCC1CC2]

Step A: Following general procedure GP-K, (R)-(+)-3-aminoquinuclidine dihydrochloride (0.71 g, 3.56 mmol) and methyl 1-benzyl-3-(2-oxoethyl)-1H-indazole-4-carboxylate (1.37 g, 4.45 mmol) from Step B of Example 27 were converted to (R)-methyl 1-benzyl-3-(2-(quinuclidin-3-ylamino)ethyl)-1H-indazole-4-carboxylate (1.1 g, 59%) as an oil: $^1$H NMR (500 MHz, CDCl$_3$) δ 7.71 (dd, J=7.5, 1.0 Hz, 1H), 7.49 (dd, J=8.5, 1.0 Hz, 1H), 7.35-7.32 (m, 1H), 7.30-7.23 (m, 3H), 7.14-7.12 (m, 2H), 5.57 (s, 2H), 3.97 (s, 3H), 3.38 (t, J=7.0 Hz, 2H), 3.32-3.16 (m, 1H), 3.05-3.00 (m, 1H), 2.97-2.93 (m, 1H), 2.89-2.79 (m, 5H), 2.50-2.46 (m, 1H), 1.90-1.85 (m, 2H), 1.75-1.68 (m, 1H), 1.57-1.50 (m, 1H), 1.37-1.30 (m, 1H); MS (ESI+) m/z 419 (M+H).

Step B: Following general procedure GP-L, (R)-methyl 1-benzyl-3-(2-(quinuclidin-3-ylamino)ethyl)-1H-indazole-4-carboxylate (1.1 mg, 2.63 mmol) and lithium hydroxide monohydrate (332 mg, 7.89 mmol) were converted lithium (R)-1-benzyl-3-(2-(quinuclidin-3-ylamino)ethyl)-1H-indazole-4-carboxylate (1.09 g, quant. yield) which was used in the next step without further purification: $^1$H NMR (300 MHz, CDCl$_3$) δ 7.37-7.34 (m, 1H), 7.30-7.26 (m, 3H), 7.25-7.11 (m, 3H), 7.06-7.03 (m, 1H), 5.54 (s, 2H), 3.27 (m, 2H), 2.85-2.70 (m, 4H), 2.67-2.50 (m, 3H), 2.18-2.12 (m, 1H), 1.75-1.45 (m, 3H), 1.40-1.15 (m, 2H): MS (ESI+) m/z 405 (M+H).

Step C: Following the procedure described in Step E of Example 27, (R)-1-benzyl-3-(2-(quinuclidin-3-ylamino)ethyl)-1H-indazole-4-carboxylate (1.09 mg, 2.63 mmol) was converted to (R)-2-benzyl-7-(quinuclidin-3-yl)-8,9-dihydro-2H-azepino[5,4,3-cd]indazol-6(7H)-one (621 mg, 61%) as a light yellow solid: $^1$H NMR (300 MHz, CDCl$_3$) δ 7.98-7.95 (m, 1H), 7.45-7.43 (m, 2H), 7.32-7.25 (m, 3H), 7.119-7.15 (m, 2H), 5.57 (s, 2H), 4.85-4.68 (1H), 4.20-3.90 (m, 2H), 3.45-3.38 (m, 1H), 3.35-2.90 (m, 7H), 2.25-2.15 (m, 1H), 1.95-1.55 (m, 4H); MS (ESI+) m/z 387 (M+H).

Step D: Following general procedure GP-U, (R)-2-benzyl-7-(quinuclidin-3-yl)-8,9-dihydro-2H-azepino[5,4,3-cd]indazol-6(7H)-one was converted to (R)-7-(quinuclidin-3-yl)-8,9-dihydro-2H-azepino[5,4,3-cd]indazol-6(7H) one (101 mg, 52%) as a white solid: MS (ESI+) m/z 297 (M+H).

Step E: Following general procedure GP-N, (R)-7-(quinuclidin-3-yl)-8,9-dihydro-2H-azepino[5,4,3-cd]indazol-6 (7H)-one was converted to (R)-7-(quinuclidin-3-yl)-8,9-dihydro-2H-azepino[5,4,3-cd]indazol-6(7H)-one, hydrochloride salt (76 mg, 67%) as a white solid: $^1$H NMR (500 MHz, DMSO-d$_6$) δ 13.08 (bs, 1H), 10.38 (bs (1H), 7.78 (d, J=7.5 Hz, 1H), 7.71 (d, J=8.0 Hz, 1H), 7.48 (t, J=8.0 Hz, 1H), 4.70 (t, J=8.0 Hz, 1H), 4.20-3.40 (m, 5H), 3.28-3.05 (m, 5H), 2.40-2.35 (m, 1H), 2.10-1.80 (m, 4H); MS (ESI+) m/z 297 (M+H); HPLC>99% (AUC), t$_R$ 11.02 min.

Examples 29 and 30

Preparation of (S)-2-(Quinuclidin-3-yl)-2,3,4,6-tetrahydro-1H-azepino[5,4,3-cd]indol-1-one, hydrochloride salt and (S)-6-(Phenylsulfonyl)-2-(quinuclidin-3-yl)-2,3,4,6-tetrahydro-1H-azepino[5,4,3-cd]indol-1-one, hydrochloride salt

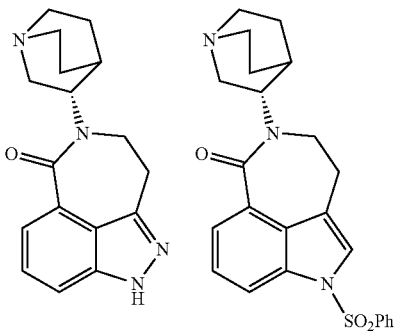

Step A: To a stirring mixture of methyl indole-4-carboxylate (5.20 g, 29.68 mmol), allyl alcohol (2.02 mL, 29.68 mmol), and triethyl borane (1.0M solution in THF, 8.90 mL, 8.90 mmol) in THF (120 mL) at room temperature under an atmosphere of nitrogen was added Pd(PPh$_3$)$_4$ (1.71 g, 1.48 mmol). The mixture was heated at 70° C. for 16 h then cooled to room temperature. The mixture was diluted with ethyl acetate (500 mL) and washed with saturated aqueous sodium bicarbonate solution (200 mL), brine, dried (Na$_2$SO$_4$), filtered, and concentrated under reduced pressure. Purification by column chromatography (silica gel, 0 to 30% ethyl acetate in hexanes) afforded methyl 3-allyl-1H-indole-4-carboxylate (5.61 g, 88%) as a pale yellow oil: $^1$H NMR (500 MHz, CDCl$_3$) δ 8.44 (b s, 1H), 7.59 (m, 1H), 7.44 (m, 1H), 7.16 (m, 1H), 7.04 (s, 1H), 6.05 (m, 1H), 5.00 (m, 2H), 3.96 (s, 3H), 3.64 (m, 2H); MS (ESI+) m/z 150 (M+H).

Step B: To a 0° C. cooled suspension of sodium hydride (60% dispersion in mineral oil, 0.450 g, 11.24 mmol) in DMF (50 mL) was slowly added a solution of methyl 3-allyl-1H-indole-4-carboxylate (2.20 g, 10.22 mmol) from Step A above in DMF (30 mL). The mixture stirred at 0° C. under an atmosphere of nitrogen for 1 h. To this was added benzenesulfonyl chloride (1.30 mL, 10.22 mmol). The mixture continued to stir for 16 h while gradually warming to room temperature. The mixture was carefully quenched with saturated aqueous ammonium chloride solution (300 mL) and the aqueous mixture was extracted with ethyl acetate (3×300 mL). The combined organic layers were washed with water (4×100 mL), brine, dried (Na$_2$SO$_4$), filtered, and concentrated under reduced pressure. Purification by column chromatography (silica gel, 0 to 30% ethyl acetate in hexanes) afforded methyl 3-allyl-1-(phenylsulfonyl)-1H-indole-4-carboxylate (3.15 g, 87%) as a pale yellow oil, which crystallized upon standing: $^1$H NMR (500 MHz, CDCl$_3$) δ 8.19 (m, 1H), 7.85 (m, 2H), 7.63 (m, 1H), 7.55 (m, 1H), 7.44 (s, 1H), 7.41 (m, 2H), 7.32 (m, 2H), 5.96 (m, 1H), 5.07 (m, 1H), 4.97 (m, 1H), 3.89 (s, 3H), 3.54 (m, 2H): MS (ESI+) m/z 356 (M+H).

Step C: To a 0° C. cooled solution of methyl 3-allyl-1-(phenylsulfonyl)-1H-indole-4-carboxylate (4.80 g, 13.50 mmol) from Step B above and N-methylmorpholine-N-oxide (2.82 g, 24.31 mmol) in a 3:1 mixture of tetrahydrofuran/water (50 mL) was added OsO$_4$ (4 wt % in water, 5.0 mL, 54.0 mmol). The resulting mixture stirred at room temperature for 24 h, then was diluted with a saturated aqueous solution of Na$_2$S$_2$O$_5$ (200 mL). The tetrahydrofuran was removed under reduced pressure and the mixture was partitioned between ethyl acetate (200 mL) and water (200 mL). The aqueous layer was extracted with ethyl acetate (3×200 mL) and the combined organic layers were washed with brine, dried (Na$_2$SO$_4$), filtered, and concentrated under reduced pressure. The residue was dissolved in a 3:1 mixture of tetrahydrofuran:water (50 mL), to which sodium periodate (11.55 g, 54.0 mmol) was added. The mixture stirred at room temperature for an additional 24 h. The tetrahydrofuran was removed under reduced pressure and the mixture was partitioned between ethyl acetate (200 mL) and water (200 mL). The aqueous layer was extracted with ethyl acetate (3×200 mL) and the combined organic layers were washed with brine, dried (Na$_2$SO$_4$), filtered, and concentrated under reduced pressure to give methyl 3-(2-oxoethyl)-1-(phenylsulfonyl)-1H-indole-4-carboxylate (2.50 g, 45%) as a crude yellow oil, which was directly elaborated without purification.

Step D: A mixture of (S)-(−)-3-aminoquinuclidine dihydrochloride (202 mg, 1.01 mmol) and methyl 3-(2-oxoethyl)-1-(phenylsulfonyl)-1H-indole-4-carboxylate (330 mg, 0.92 mmol) from Step C above in 1% acetic acid in dichloromethane (20 mL) was stirred at ambient temperature for 16 h. Sodium triacetoxyborohydride (584 mg, 2.76 mmol) was added, and the resulting suspension was stirred for 2 h at ambient temperature. The solvent was removed under reduced pressure, and the crude material purified by column chromatography (silica gel, 10:1:0.1 dichloromethane/methanol/concentrated ammonium hydroxide) to afford (S)-methyl 1-(phenylsulfonyl)-3-(2-(quinuclidin-3-ylamino)ethyl)-1H-indole-4-carboxylate (172 mg, 40%) as a yellow oil: MS (ESI+) m/z 468 (M+H).

Step E: To a solution of (S)-methyl 1-(phenylsulfonyl)-3-(2-(quinuclidin-3-ylamino)ethyl)-1H-indole-4-carboxylate (480 mg, 1.02 mmol) from Step D above in tetrahydrofuran (10 mL) was added lithium hydroxide monohydrate (129 mg, 3.07 mmol) in water (3 mL). The mixture was stirred at ambient temperature overnight and then concentrated under reduced pressure. The residue was dried overnight under vacuum to afford crude lithium (S)-1-(phenylsulfonyl)-3-(2-(quinuclidin-3-ylamino)ethyl)-1H-indole-4-carboxylate, which was used in the next step without further purification: MS (ESI+) m/z 454 (M+H).

Step F: To a solution of the crude lithium (S)-1-(phenylsulfonyl)-3-(2-(quinuclidin-3-ylamino)ethyl)-1H-indole-4-carboxylate (533 mg, 0.37 mmol) from Step E above in DMF (10 mL) was added HBTU (210 mg, 0.55 mmol) and the mixture was stirred at ambient temperature for 2 h. The mixture was concentrated under reduced pressure at 40° C., providing a 1:1 mixture of (S)-6-(phenylsulfonyl)-2-(quinuclidin-3-yl)-2,3,4,6-tetrahydro-1H-azepino[5,4,3-cd]indol-1-one and (S)-2-(quinuclidin-3-yl)-2,3,4,6-tetrahydro-1H-azepino[5,4,3-cd]indol-1-one by LC-MS. The crude material was purified by column chromatography (silica gel, 10:1:0.1 dichloromethane/methanol/concentrated ammonium hydroxide) to afford (S)-6-(phenylsulfonyl)-2-(quinuclidin-3-yl)-2,3,4,6-tetrahydro-1H-azepino[5,4,3-cd]indol-1-one (92 mg) and (S)-2-(quinuclidin-3-yl)-2,3,4,6-tetrahydro-1H-azepino[5,4,3-cd]indol-1-one (52 mg) as an off-white solid. These materials were immediately dissolved in methanol (2 mL) and treated with hydrochloric acid (1.25 M solution in methanol, 1 eq) separately. The mixtures were stirred for 15 min, concentrated under reduced pressure, and dried under vacuum. The resulting solids were lyophilized from water (8 mL) and acetonitrile (1 mL) to afford (S)-6-(phenylsulfonyl)-2-(quinuclidin-3-yl)-2,3,4,6-tetrahydro-1H-azepino[5,4,3-cd]indol-1-one, hydrochloride salt (23.5 mg) and (S)-2-(quinuclidin-3-yl)-2,3,4,6-tetrahydro-1H-azepino[5,4,3-cd]indol-1-one, hydrochloride salt (29.1 mg) as off-white solids: (S)-6-(phenylsulfonyl)-2-(quinuclidin-3-yl)-2,3,4,6-tetrahydro-1H-azepino[5,4,3-cd]indol-1-one, hydrochloride salt: $^1$H NMR (500 MHz, DMSO-d$_6$) δ 10.31 (bs, 1H), 8.14 (d, J=8.2 Hz, 1H), 7.99 (d, J=8.5 Hz, 1H), 7.93 (d, J=7.6 Hz, 1H), 7.83 (s, 1H), 7.68 (t, J=5.6 Hz, 1H), 7.61 (m, 2H), 7.48 (t, J=7.5 Hz, 1H), 4.71 (m, 1H), 3.80-3.31 (m, 5H), 3.19 (m, 4H), 2.27 (m, 1H), 2.15-1.78 (m, 4H), 1.31 (m, 1H); MS (ESI+) m/z 436 (M+H); HPLC 98.7% (AUC), t$_R$ 16.42 min. (S)-2-(quinuclidin-3-yl)-2,3,4,6-tetrahydro-1H-azepino[5,4,3-cd]indol-1-one, hydrochloride salt: $^1$H NMR (500 MHz, DMSO-d$_6$) δ 11.18 (bs, 1H), 9.98 (bs (1H), 7.72 (d, J=7.5 Hz, 1H), 7.55 (d, J=7.9 Hz, 1H), 7.31 (s, 1H), 7.18 (t, J=7.7 Hz, 1H), 4.72 (m, 1H), 4.10-3.33 (m, 5H), 3.24-2.89 (m, 5H), 2.30 (m, 1H), 2.07-1.79 (m, 4H); MS (ESI+) m/z 296 (M+H); HPLC 97.6% (AUC), t$_R$ 11.75 min.

Example 31

Preparation of (S)-2-Methyl-7-(quinuclidin-3-yl)-8,9-dihydro-2H-azepino[5,4,3-cd]indazol-6(7H)-one, hydrochloride salt

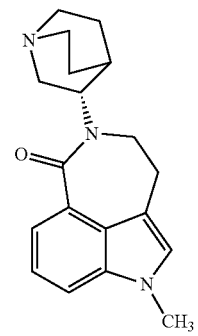 [SMILES: Cn1cc2c3c(cccc31)C(=O)N([C@@H]1CN3CCC1CC3)CC2]

Step A: Following the procedure in Example 2, except that methyl iodide was used instead of benzyl bromide, methyl indole-4-carboxylate (7.0 g, 40.0 mmol) was converted to methyl 1-methyl-1H-indole-4-carboxylate (6.44 g, 88%): $^1$H NMR (300 MHz, CDCl$_3$) δ 7.91 (d, J=7.5 Hz, 1H), 7.52 (d, J=8.1 Hz, 1H), 7.25 (t, J=7.8 Hz, 1H), 7.18 (d, J=3.0 Hz, 1H), 7.10 (d, J=3.0 Hz, 1H), 3.98 (s, 3H), 3.82 (s, 3H); MS (ESI+) m/z 190 (M+H).

Step B: Following general procedure GP-O, methyl 1-methyl-1H-indole-4-carboxylate (6.40 g, 24.16 mmol) was converted to methyl 3-formyl-1-methyl-1H-indole-4-carboxylate (5.41 g, 76%): $^1$H NMR (300 MHz, CDCl$_3$) δ 10.49, (s, 1H), 7.98 (s, 1H), 7.88 (dd, J=7.5, 1.2 Hz, 1H), 7.57 (dd, J=8.1, 1.0 Hz, 1H), 7.36 (t, J=7.8 Hz, 1H), 3.99 (s, 3H), 3.90 (s, 3H); MS (ESI+) m/z 218 (M+H).

Step C: Following general procedure GP-P, methyl 3-formyl-1-methyl-1H-indole-4-carboxylate (3.0 g, 13.82 mmol) was converted to methyl 1-methyl-3-(2-oxoethyl)-1H-indole-4-carboxylate (1.73 g, 54%): $^1$H NMR (500 MHz, CDCl$_3$) δ 9.83 (s, 1H), 7.79 (d, J=7.5 Hz, 1H), 7.51 (d, J=8.5 Hz, 1H), 7.25-7.22 (m, 1H), 7.09 (s, 1H), 4.01 (s, 2H), 3.90 (s, 3H), 3.78 (s, 3H); MS (ESI+) m/z 232 (M+H).

Step D: Following general procedure GP-Q, methyl 1-methyl-3-(2-oxoethyl)-1H-indole-4-carboxylate (250 mg, 0.61 mmol) and (S)-(—)-3-aminoquinuclidine dihydrochloride were converted to (S)-methyl 1-methyl-3-(2-(quinuclidin-3-ylamino)ethyl)-1H-indole-4-carboxylate (231 mg, 63%): $^1$H NMR (500 MHz, CDCl$_3$) δ 7.63 (d, J=7.5 Hz, 1H), 7.46 (d, J=8.0 Hz, 1H), 7.22 (t, J=8.0 Hz, 1H), 7.03 (s, 1H), 5.70 (br s, 1H), 3.94 (s, 3H), 3.78 (s, 3H), 3.38-3.31 (m, 1H), 3.16-3.06 (m, 2H), 2.90-2.70 (m, 5H), 2.50-2.40 (m, 2H), 1.95-1.90 (m, 1H), 1.85-1.80 (m, 1H), 1.70-1.60 (m, 2H), 1.55-1.25 (m, 2H); MS (ESI+) m/z 342 (M+H)

Step E: Following general procedure GP-R, (S)-methyl 1-methyl-3-(2-(quinuclidin-3-ylamino)ethyl)-1H-indole-4-carboxylate and lithium hydroxide monohydrate were converted to lithium (S)-1-methyl-3-(2-(quinuclidin-3-ylamino)

ethyl)-1H-indole-4-carboxylate, which was used in the next step without further purification: MS (ESI+) m/z 328 (M+H).

Step F: Following general procedure GP-S, lithium (S)-1-methyl-3-(2-(quinuclidin-3-ylamino)ethyl)-1H-indole-4-carboxylate (295 mg, 0.88 mmol) was converted to (S)-6-methyl-2-(quinuclidin-3-yl)-2,3,4,6-tetrahydro-1H-azepino[5,4,3-cd]indol-1-one (161 mg, 59%): $^1$H NMR (300 MHz, CDCl$_3$) δ 7.97 (d, J=7.5 Hz, 1H), 7.42 (d, J=8.0 Hz, 1H), 7.31 (t, J=8.0 Hz, 1H), 6.91 (s, 1H), 4.85-4.70 (1H), 4.10-3.80 (m, 2H), 3.78 (s, 3H), 3.37 (t, J=13.5 Hz, 1H), 3.15-2.90 (m, 7H), 2.20-2.10 (m, 1H), 1.90-1.50 (m, 4H); MS (ESI+) m/z 310 (M+H)

Step G: Following general procedure GP-T, (S)-2-(quinuclidin-3-yl)-2,3,4,6-tetrahydro-1H-azepino[5,4,3-cd]indol-1-one was converted to (S)-2-(quinuclidin-3-yl)-2,3,4,6-tetrahydro-1H-azepino[5,4,3-cd]indol-1-one, hydrochloride salt (68 mg, 38%): $^1$H NMR (500 MHz, DMSO-d$_6$) δ 10.37 (bs, 1H), 7.75 (d, J=7.5 Hz, 1H), 7.62 (d, J=8.0 Hz, 1H), 7.30 (s, 1H), 7.25 (t, J=8.0 Hz, 1H), 4.80-4.70 (m, 1H), 4.10-3.90 (m, 1H), 3.80 (s, 3H), 3.75-3.35 (m, 4H), 3.28-3.18 (m, 3H), 3.15-2.75 (m, 2H), 2.35-2.30 (m, 1H), 2.10-1.80 (m, 4H); MS (ESI+) m/z 310 (M+H); HPLC>99% (AUC), t$_R$ 13.07 min.

Example 32

Preparation of (S)-6-benzyl-2-(quinuclidin-3-yl)-2,3,4,6-tetrahydro-1H-azepino[5,4,3-cd]indol-1-one, hydrochloride salt

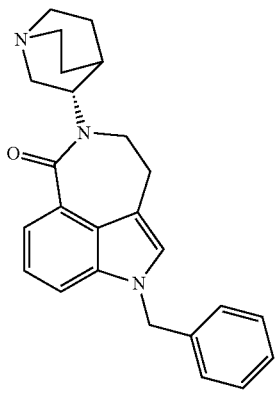 [SMILES: O=C1c2cccc3c2c(cn3Cc2ccccc2)CCN1[C@@H]1CN2CCC1CC2]

Step A: Following general procedure GP-O, methyl 1-benzyl-1H-indole-4-carboxylate (A1b) was converted to methyl 1-benzyl-3-formyl-1H-indole-4-carboxylate (12.4 g, 77%): $^1$H NMR (500 MHz, CDCl$_3$) δ 10.79, (s, 1H), 8.03 (s, 1H), 7.86 (dd, J=7.5, 1.0 Hz, 1H), 7.52 (dd, J=7.5, 1.0 Hz, 1H), 7.38-7.25 (m, 4H), 7.19-7.15 (m, 2H), 5.38 (s, 2H), 3.99 (s, 3H): MS (ESI+) m/z 294 (M+H).

Step B: Following general procedure GP-P, methyl 1-benzyl-3-formyl-1H-indole-4-carboxylate was converted to methyl 1-benzyl-3-(2-oxoethyl)-1H-indole-4-carboxylate: $^1$H NMR (500 MHz, CDCl$_3$) δ 9.83 (s, 1H), 7.77 (dd, J=7.5, 1.0 Hz, 1H), 7.47 (dd, J=7.5, 1.0 Hz, 1H), 7.32-7.27 (m, 3H), 7.19 (t, J=7.5 Hz, 1H), 7.15 (s, 1H), 7.10-7.08 (m, 2H), 5.32 (s, 2H), 4.01 (s, 2H), 3.90 (s, 3H); MS (ESI+) m/z 308 (M+H).

Step C: Following general procedure GP-Q, (S)-(−)-3-aminoquinuclidine dihydrochloride and methyl 1-benzyl-3-(2-oxoethyl)-1H-indole-4-carboxylate were converted to methyl 1-benzyl-3-(2-(quinuclidin-3-ylamino)ethyl)-1H-indole-4-carboxylate (516 mg, 57%): $^1$H NMR (300 MHz, CDCl$_3$) δ 7.67 (dd, J=7.5, 1.0 Hz, 1H), 7.45-7.40 (m, 1H), 7.32-7.27 (m, 4H), 7.22 (s, 1H), 7.15 (t, J=7.5 Hz, 1H), 7.08-7.05 (m, 2H), 5.27 (s, 2H), 3.95 (s, 3H), 3.54-3.40 (m, 5H), 3.38-2.90 (m, 6H), 2.45-2.30 (m, 2H), 2.20-1.65 (m, 3H); MS (ESI+) m/z 418 (M+H)

Step D: Following general procedure GP-R, (S)-methyl 1-benzyl-3-(2-(quinuclidin-3-ylamino)ethyl)-1H-indole-4-carboxylate was converted to crude lithium 1-benzyl-3-(2-(quinuclidin-3-ylamino)ethyl)-1H-indole-4-carboxylate, which was used in the next step without further purification: MS (ESI+) m/z 404 (M+H).

Step E: Following general procedure GP-S, lithium (S)-1-benzyl-3-(2-(quinuclidin-3-ylamino)ethyl)-1H-indole-4-carboxylate was converted to (S)-6-benzyl-2-(quinuclidin-3-yl)-2,3,4,6-tetrahydro-1H-azepino[5,4,3-cd]indol-1-one: $^1$H NMR (300 MHz, CDCl$_3$) δ 7.98 (d, J=7.5 Hz, 1H), 7.39 (d, J=7.5 Hz, 1H), 7.32-7.25 (m, 4H), 7.10-7.08 (m, 2H), 6.97 (s, 1H), 5.31 (s, 2H), 4.85-4.70 (1H), 4.10-3.80 (m, 2H), 3.35 (t, J=11.0 Hz, 1H), 3.15-2.90 (m, 7H), 2.20-2.10 (m, 1H), 1.90-1.50 (m, 4H); MS (ESI+) m/z 386 (M+H).

Step F: Following general procedure GP-T, (S)-6-benzyl-2-(quinuclidin-3-yl)-2,3,4,6-tetrahydro-1H-azepino[5,4,3-cd]indol-1-one was converted to (S)-6-benzyl-2-(quinuclidin-3-yl)-2,3,4,6-tetrahydro-1H-azepino[5,4,3-cd]indol-1-one, hydrochloride salt (95 mg, 95%): $^1$H NMR (500 MHz, DMSO-d$_6$) δ 10.51 (bs, 1H), 7.74 (d, J=7.5 Hz, 1H), 7.66 (d, J=8.0 Hz, 1H), 7.47 (s, 1H), 7.930 (t, J=7.5 Hz, 2H), 7.25-7.19 (m, 4H), 5.42 (s, 2H), 4.71 (m, 1H), 4.10-3.31 (m, 5H), 3.26-3.15 (m, 3H), 3.10-2.80 (m, 2H), 2.35-2.20 (m, 1H), 2.10-1.85 (m, 4H); MS (ESI+) m/z 386 (M+H); HPLC>99% (AUC), t$_R$ 10.70 min.

Example 33

Preparation of (R)-2-(Quinuclidin-3-yl)-2,3,4,6-tetrahydro-1H-azepino[5,4,3-cd]indol-1-one, hydrochloride salt

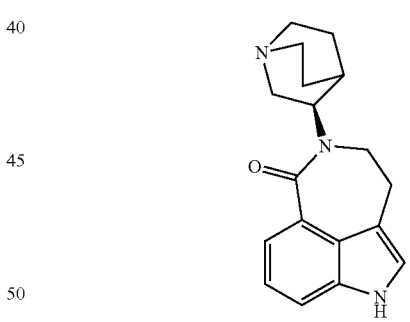

Step A: Following general procedure GP-Q, methyl 1-benzyl-3-(2-oxoethyl)-1H-indole-4-carboxylate from Step B of Example 32 and (R)-(−)-3-aminoquinuclidine dihydrochloride were converted to (R)-methyl 1-benzyl-3-(2-(quinuclidin-3-ylamino)ethyl)-1H-indole-4-carboxylate (701 mg, 68%): $^1$H NMR (300 MHz, CDCl$_3$) δ 7.63 (dd, J=7.5, 1.0 Hz, 1H), 7.44 (dd, J=7.5, 1.0 Hz, 1H), 7.32-7.23 (m, 4H), 7.19-7.05 (m, 4H), 5.31 (s, 2H), 3.95 (s, 3H), 3.20-3.05 (m, 3H), 2.95-2.70 (m, 7H), 2.50-2.40 (m, 1H), 1.85-1.65 (m, 3H), 1.55-1.22 (m, 2H); MS (ESI+) m/z 418 (M+H)

Step B: Following general procedure GP-R, (R)-methyl 1-benzyl-3-(2-(quinuclidin-3-ylamino)ethyl)-1H-indole-4-carboxylate (516 mg, 1.24 mmol) and lithium hydroxide monohydrate (129 mg, 3.07 mmol) were converted to lithium (R)-1-benzyl-3-(2-(quinuclidin-3-ylamino) ethyl)-1H-indole-4-carboxylate, which was used in the next step without further purification; MS (ESI+) m/z 404 (M+H).

Step C: Following general procedure GP-S, lithium (R)-1-benzyl-3-(2-(quinuclidin-3-ylamino)ethyl)-1H-indole-4-carboxylate (725 mg, 1.24 mmol) was converted to (R)-6-benzyl-2-(quinuclidin-3-yl)-2,3,4,6-tetrahydro-1H-azepino[5,4,3-cd]indol-1-one (354 mg, 55%): $^1$H NMR (300 MHz, CDCl$_3$) δ 7.98 (d, J=7.5 Hz, 1H), 7.39 (d, J=7.5 Hz, 1H), 7.32-7.25 (m, 4H), 7.10-7.08 (m, 2H), 6.97 (s, 1H), 5.31 (s, 2H), 4.85-4.70 (1H), 4.10-3.80 (m, 2H), 3.35 (t, J=11.0 Hz, 1H), 3.15-2.90 (m, 7H), 2.20-2.10 (m, 1H), 1.90-1.50 (m, 4H); MS (ESI+) m/z 386 (M+H).

Step D: Following general procedure GP-U, (R)-6-benzyl-2-(quinuclidin-3-yl)-2,3,4,6-tetrahydro-1H-azepino[5,4,3-cd]indol-1-one (200 mg, 0.519 mmol) was converted to (R)-2-(quinuclidin-3-yl)-2,3,4,6-tetrahydro-1H-azepino[5,4,3-cd]indol-1-one (140 mg, 52%): $^1$H NMR (500 MHz, DMSO-d$_6$) δ 11.12 (s, 1H), 7.69 (dd, J=7.5, 0.6 Hz, 1H), 7.66 (dd, J=7.5, 0.6 Hz, 1H), 7.28 (s, 1H), 7.17 (t, J=8.0 Hz, 1H), 4.65-4.45 (m, 1H), 4.15-3.50 (m, 3H), 3.20-2.65 (m, 7H), 2.00-1.90 (m, 1H), 1.80-1.35 (m, 4H); MS (ESI+) m/z 296 (M+H).

Step E: Following general procedure GP-T, (R)-2-(quinuclidin-3-yl)-2,3,4,6-tetrahydro-1H-azepino[5,4,3-cd]indol-1-one (90 mg, 0.305 mmol) in methanol (2 mL) was converted to (R)-2-(quinuclidin-3-yl)-2,3,4,6-tetrahydro-1H-azepino[5,4,3-cd]indol-1-one, hydrochloride salt (100 mg, 66%): $^1$H NMR (500 MHz, DMSO-d$_6$) δ 11.21 (bs, 1H), 10.34 (bs, 1H), 7.72 (d, J=7.5 Hz, 1H), 7.56 (d, J=8.0 Hz, 1H), 7.35 (s, 1H), 7.19 (t, J=7.5 Hz, 1H), 4.80-4.68 (m, 1H), 4.10-3.33 (m, 5H), 3.28-3.18 (m, 3H), 3.15-2.75 (m, 2H), 2.35-2.30 (m, 1H), 2.07-1.80 (m, 4H); MS (ESI+) m/z 296 (M+H); HPLC>99% (AUC), t$_R$ 11.94 min.

J=8.0 Hz, 1H), 7.21 (t, J=7.5 Hz, 1H), 7.03 (s, 1H), 3.98 (s, 3H), 3.77 (s, 3H), 3.15-3.08 (m, 2H), 2.90-2.70 (m, 7H), 2.41-2.37 (m, 1H), 2.06-2.04 (m, 1H), 1.99-1.90 (m, 1H), 1.84-1.75 (m, 2H), 1.68-1.60 (m, 2H), 1.50-1.40 (m, 1H), 1.35-1.25 (m, 1H); MS (ESI+) m/z 342 (M+H)

Step B: Following general procedure GP-R, (R)-methyl 1-methyl-3-(2-(quinuclidin-3-ylamino)ethyl)-1H-indole-4-carboxylate (500 mg, 1.46 mmol) and lithium hydroxide monohydrate (129 mg, 3.07 mmol) were converted to lithium (R)-1-methyl-3-(2-(quinuclidin-3-ylamino) ethyl)-1H-indole-4-carboxylate, which was used in the next step without further purification: MS (ESI+) m/z 328 (M+H).

Step C: Following general procedure GP-S, lithium (R)-1-methyl-3-(2-(quinuclidin-3-ylamino)ethyl)-1H-indole-4-carboxylate (746 mg, 1.46 mmol) was converted to (R)-6-methyl-2-(quinuclidin-3-yl)-2,3,4,6-tetrahydro-1H-azepino[5,4,3-cd]indol-1-one (309 mg, 68%): $^1$H NMR (300 MHz, CDCl$_3$) δ 7.97 (d, J=7.5 Hz, 1H), 7.42 (d, J=8.0 Hz, 1H), 7.31 (t, J=8.0 Hz, 1H), 6.91 (s, 1H), 4.85-4.70 (1H), 4.10-3.80 (m, 2H), 3.78 (s, 3H), 3.37 (t, J=13.5 Hz, 1H), 3.15-2.90 (m, 7H), 2.20-2.10 (m, 1H), 1.90-1.50 (m, 4H); MS (ESI+) m/z 310 (M+H)

Step D: Following general procedure GP-T, (R)-6-methyl-2-(quinuclidin-3-yl)-2,3,4,6-tetrahydro-1H-azepino[5,4,3-cd]indol-1-one (309 mg, 1.0 mmol) and HCl were converted to (R)-6-methyl-2-(quinuclidin-3-yl)-2,3,4,6-tetrahydro-1H-azepino[5,4,3-cd]indol-1-one, hydrochloride salt (240 mg, 69%): $^1$H NMR (500 MHz, DMSO-d$_6$) δ 10.56 (bs, 1H), 7.75 (d, J=7.5 Hz, 1H), 7.62 (d, J=8.0 Hz, 1H), 7.30 (s, 1H), 7.27-7.22 (m, 1H), 4.80-4.70 (m, 1H), 4.10-3.90 (m, 1H), 3.78 (s, 3H), 3.75-3.45 (m, 4H), 3.28-3.18 (m, 3H), 3.15-2.75 (m, 2H), 2.35-2.30 (m, 1H), 2.10-1.80 (m, 4H); MS (ESI+) m/z 310 (M+H); HPLC>99% (AUC), t$_R$ 9.05 min.

Example 34

Preparation of (R)-2-Methyl-7-(quinuclidin-3-yl)-8,9-dihydro-2H-azepino[5,4,3-cd]indazol-6(7H)-one, hydrochloride salt Example 35

Preparation of (R)-6-benzyl-2-(quinuclidin-3-yl)-2,3,4,6-tetrahydro-1H-azepino[5,4,3-cd]indol-1-one, hydrochloride salt

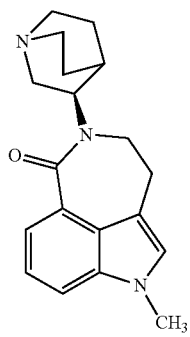 [SMILES: Cn1cc2c3c(cccc31)C(=O)N([C@H]1CN3CCC1CC3)CC2]

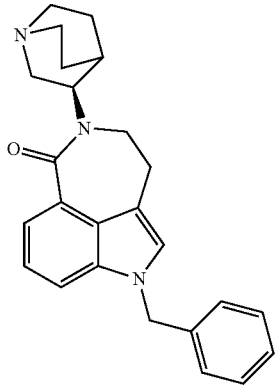 [SMILES: O=C1c2cccc3c2c(cn3Cc2ccccc2)CCN1[C@H]1CN2CCC1CC2]

Step A: Following general procedure GP-Q, methyl 1-methyl-3-(2-oxoethyl)-1H-indole-4-carboxylate (775 mg, 3.26 mmol) from Step D of Example 31 and (R)-(+)-3-aminoquinuclidine dihydrochloride (812 mg, 4.08 mmol) were converted to (R)-methyl 1-methyl-3-(2-(quinuclidin-3-ylamino) ethyl)-1H-indole-4-carboxylate (510 mg, 68%): $^1$H NMR (500 MHz, CDCl$_3$) δ 7.63 (dd, J=7.0, 0.5 Hz, 1H), 7.46 (dd, Step A: Following general procedure GP-Q, methyl 1-benzyl-3-(2-oxoethyl)-1H-indole-4-carboxylate from Step B of Example 32 and (R)-(+)-3-aminoquinuclidine dihydrochloride were converted to (R)-methyl 1-benzyl-3-(2-(quinuclidin-3-ylamino)ethyl)-1H-indole-4-carboxylate (701 mg, 68%): ¹H NMR (300 MHz, CDCl₃) δ 7.63 (dd, J=7.5, 1.0 Hz, 1H), 7.44 (dd, J=7.5, 1.0 Hz, 1H), 7.32-7.23 (m, 4H), 7.19-7.05 (m, 4H), 5.31 (s, 2H), 3.95 (s, 3H), 3.20-3.05 (m, 3H), 2.95-2.70 (m, 7H), 2.50-2.40 (m, 1H), 1.85-1.65 (m, 3H), 1.55-1.22 (m, 2H); MS (ESI+) m/z 418 (M+H)

Step B: Following general procedure GP-R, (R)-methyl 1-benzyl-3-(2-(quinuclidin-3-ylamino)ethyl)-1H-indole-4-carboxylate (516 mg, 1.24 mmol) and lithium hydroxide monohydrate (129 mg, 3.07 mmol) were converted to lithium (R)-1-benzyl-3-(2-(quinuclidin-3-ylamino) ethyl)-1H-indole-4-carboxylate, which was used in the next step without further purification; MS (ESI+) m/z 404 (M+H).

Step C: Following general procedure GP-S, lithium (R)-1-benzyl-3-(2-(quinuclidin-3-ylamino)ethyl)-1H-indole-4-carboxylate (725 mg, 1.24 mmol) was converted to (R)-6-benzyl-2-(quinuclidin-3-yl)-2,3,4,6-tetrahydro-1H-azepino[5,4,3-cd]indol-1-one (354 mg, 55%): ¹H NMR (300 MHz, CDCl₃) δ 7.98 (d, J=7.5 Hz, 1H), 7.39 (d, J=7.5 Hz, 1H), 7.32-7.25 (m, 4H), 7.10-7.08 (m, 2H), 6.97 (s, 1H), 5.31 (s, 2H), 4.85-4.70 (1H), 4.10-3.80 (m, 2H), 3.35 (t, J=11.0 Hz, 1H), 3.15-2.90 (m, 7H), 2.20-2.10 (m, 1H), 1.90-1.50 (m, 4H); MS (ESI+) m/z 386 (M+H).

Step D: Following general procedure GP-T, (R)-6-benzyl-2-(quinuclidin-3-yl)-2,3,4,6-tetrahydro-1H-azepino[5,4,3-cd]indol-1-one (100 mg, 0.259 mmol) was converted to (R)-6-benzyl-2-(quinuclidin-3-yl)-2,3,4,6-tetrahydro-1H-azepino[5,4,3-cd]indol-1-one, hydrochloride salt (68 mg, 89%): ¹H NMR (500 MHz, DMSO-d₆) δ 10.51 (bs, 1H), 7.74 (d, J=7.5 Hz, 1H), 7.66 (d, J=8.0 Hz, 1H), 7.47 (s, 1H), 7.930 (t, J=7.5 Hz, 2H), 7.25-7.19 (m, 4H), 5.42 (s, 2H), 4.71 (m, 1H), 4.10-3.31 (m, 5H), 3.26-3.15 (m, 3H), 3.10-2.80 (m, 2H), 2.35-2.20 (m, 1H), 2.10-1.85 (m, 4H); MS (ESI+) m/z 386 (M+H); HPLC>99% (AUC), $t_R$ 10.73 min.

Example 36

Preparation of (R)-6-(4-fluorophenyl)-2-(quinuclidin-3-yl)-2,3,4,6-tetrahydro-1H-azepino[5,4,3-cd]indol-1-one, hydrochloride salt

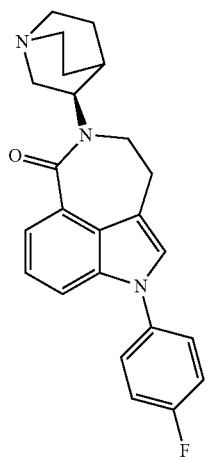 [SMILES: O=C1c2cccc3c2c(cn3-c2ccc(F)cc2)CCN1[C@H]1CN2CCC1CC2]

Step A: To a solution of methyl 1H-indole-4-carboxylate (3.0 g, 17.1 mmol) in DMSO (25 mL) and 1,4-dioxane (25 mL) in a sealed tube were added potassium phosphate (7.3 g, 34.3 mmol), dimethylethylenediamine (1.0 mL, 9.1 mmol), L-proline (1.1 g, 9.1 mmol), 1-bromo-4-fluorobenzene (1.3 mL, 11.42 mmol), and copper iodide (1.1 g, 5.7 mmol). The mixture was purged with argon gas; the tube was sealed and heated at 110° C. overnight. The reaction mixture was cooled down to rt, washed with water (100 mL) and the aqueous mixture was extracted with dichloromethane (3×150 mL). The combined organic layers were dried (Na₂SO₄), filtered, and concentrated under reduced pressure. Purification of the resulting residue by column chromatography (0% to 50% dichloromethane in hexanes) afforded methyl 1-(4-fluorophenyl)-1H-indole-4-carboxylate (2.1 g, 68%) as a white solid: ¹H NMR (300 MHz, DMSO) δ 7.87-7.82 (m, 2H), 7.75 (d, J=8.4 Hz, 1H), 7.68-7.63 (m, 2H), 7.49-7.42 (m, 2H), 7.32 (t, J=7.8 Hz, 1H), 7.20 (dd, J=3.0, 0.9 Hz, 1H), 3.93 (s, 3H); MS (ESI+) m/z 270 [M+H]⁺.

Step B: Following general procedure GP-O, methyl 1-(4-fluorophenyl)-1H-indole-4-carboxylate was converted to methyl 1-(4-fluorophenyl)-3-formyl-1H-indole-4-carboxylate: ¹H NMR (500 MHz, DMSO) δ 10.20 (s, 1H), 8.58 (s, 1H), 7.76-7.73 (m, 2H), 7.67-7.65 (m, 2H), 7.52-7.48 (m, 2H), 7.42 (t, J=8.0 Hz, 1H), 3.89 (s, 3H).

Step C: Following general procedure GP-P, methyl 1-(4-fluorophenyl)-3-formyl-1H-indole-4-carboxylate was converted to methyl 1-(4-fluorophenyl)-3-(2-oxoethyl)-1H-indole-4-carboxylate: ¹H NMR (300 MHz, DMSO) δ 9.74 (s, 1H), 7.73-7.26 (m, 8H), 4.03 (s, 2H), 3.83 (s, 3H).

Step D: Following general procedure GP-Q except that 1,4-dioxane was used as the solvent, methyl 1-(4-fluorophenyl)-3-(2-oxoethyl)-1H-indole-4-carboxylate and (R)-(+)-3-aminoquinuclidine dihydrochloride were converted to (R)-methyl 1-(4-fluorophenyl)-3-(2-(quinuclidin-3-ylamino) ethyl)-1H-indole-4-carboxylate: ¹H NMR (300 MHz, DMSO) δ 7.65-7.58 (m, 4H), 7.52-7.40 (m, 3H), 7.24 (t, J=7.8 Hz, 1H), 4.11-4.13 (m, 1H), 3.91 (s, 3H), 3.17-2.63 (m, 8H), 2.31-2.27 (m, 1H), 1.83-1.76 (m, 3H), 1.64-1.57 (m, 1H), 1.44-1.40 (m, 1H), 1.26-1.23 (m, 1H); MS (ESI+) m/z 422 [M+H]⁺.

Step E: Following general procedure GP-R, (R)-methyl 1-(4-fluorophenyl)-3-(2-(quinuclidin-3-ylamino)ethyl)-1H-indole-4-carboxylate was converted to crude lithium (R)-1-(4-fluorophenyl)-3-(2-(quinuclidin-3-ylamino)ethyl)-1H-indole-4-carboxylate: MS (ESI+) m/z 406 [acid, M+H]⁺.

Step F: Following the procedure in Step C of Example 16, lithium (R)-1-(4-fluorophenyl)-3-(2-(quinuclidin-3-ylamino)ethyl)-1H-indole-4-carboxylate was converted to (R)-6-(4-fluorophenyl)-2-(quinuclidin-3-yl)-2,3,4,6-tetrahydro-1H-azepino[5,4,3-cd]indol-1-one (5.5 mg, 10%).

Step G: Following general procedure GP-T, (R)-6-(4-fluorophenyl)-2-(quinuclidin-3-yl)-2,3,4,6-tetrahydro-1H-azepino[5,4,3-cd]indol-1-one was converted to (R)-6-(4-fluorophenyl)-2-(quinuclidin-3-yl)-2,3,4,6-tetrahydro-1H-azepino[5,4,3-cd]indol-1-one, hydrochloride salt: ¹H NMR (500 MHz, d₄-MeOH) δ 7.90 (d, J=7.5 Hz, 1H), 7.64 (d, J=8.0 Hz, 1H), 7.55-7.52 (m, 2H), 7.42 (s, 1H), 7.34-7.29 (m, 3H), 4.25-3.55 (m, 6H), 3.54-3.05 (m, 6H), 2.52-2.51 (m, 1H), 2.15-1.98 (m, 3H); MS (ESI+) m/z 390 [M+H]$^+$; HPLC 97.2% (AUC), $t_R$ 10.22 min.

Example 37

Preparation of Endo-6-methyl-2-(9-methyl-9-azabicyclo[3.3.1]nonan-3-yl)-2,3,4,6-tetrahydro-1H-azepino[5,4,3-cd]indol-1-one, hydrochloride salt

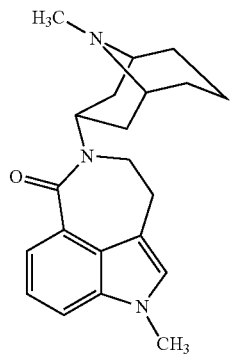 [SMILES: CN1C2CCCC1CC(N1CCc3cn(C)c4cccc(c34)C1=O)C2]

Step A: Following general procedure GP-Q except that 1,4-dioxane was used as the solvent, methyl 1-methyl-3-(2-oxoethyl)-1H-indole-4-carboxylate (775 mg, 3.26 mmol) from Step D of Example 31 and endo-9-methyl-9-azabicyclo[3.3.1]nonan-3-amine were converted to endo-methyl 1-methyl-3-(2-(9-methyl-9-azabicyclo[3.3.1]nonan-3-ylamino)ethyl)-1H-indole-4-carboxylate: MS (ESI+) m/z 370 [M+H]$^+$.

Step B: Following general procedure GP-R, endo-methyl 1-methyl-3-(2-(9-methyl-9-azabicyclo[3.3.1]nonan-3-ylamino)ethyl)-1H-indole-4-carboxylate was converted to crude lithium (endo)-1-methyl-3-(2-(9-methyl-9-azabicyclo[3.3.1]nonan-3-ylamino)ethyl)-1H-indole-4-carboxylate: MS (ESI+) m/z 356 [acid, M+H]$^+$.

Step C: Following the procedure in Step C of Example 16, lithium (endo)-1-methyl-3-(2-(9-methyl-9-azabicyclo[3.3.1]nonan-3-ylamino)ethyl)-1H-indole-4-carboxylate was converted to endo-6-methyl-2-(9-methyl-9-azabicyclo[3.3.1]nonan-3-yl)-2,3,4,6-tetrahydro-1H-azepino[5,4,3-cd]indol-1-one (5.5 mg, 10%).

Step D: Following general procedure GP-T, endo-6-methyl-2-(9-methyl-9-azabicyclo[3.3.1]nonan-3-yl)-2,3,4,6-tetrahydro-1H-azepino[5,4,3-cd]indol-1-one was converted to endo-6-methyl-2-(9-methyl-9-azabicyclo[3.3.1]nonan-3-yl)-2,3,4,6-tetrahydro-1H-azepino[5,4,3-cd]indol-1-one, hydrochloride salt: $^1$H NMR (500 MHz, DMSO) δ 9.28 (s, 1H), 7.77 (d, J=7.0 Hz, 1H), 7.62 (d, J=8.0 Hz, 1H), 7.29-7.23 (m, 2H), 5.34-5.31 (m, 1H), 3.87-3.70 (m, 5H), 3.47-2.63 (m, 7H), 2.35-2.20 (m, 2H), 2.19-1.80 (m, 5H), 1.79-1.51 (m, 3H); MS (ESI+) m/z 338 [M+H]$^+$; HPLC>99% (AUC), $t_R$ 13.61 min.

Example 38

Preparation of Endo-2-methyl-7-(8-methyl-8-azabicyclo[3.2.1]octan-3-yl)-7,8-dihydropyrazolo[3,4,5-de]isoquinolin-6(2H)-one, hydrochloride salt

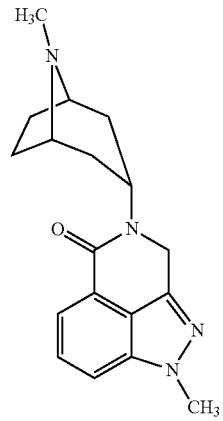 [SMILES: CN1C2CCC1CC(N1Cc3nn(C)c4cccc(c34)C1=O)C2]

Step A: Sodium hydride (60%) (0.19 g) was added in portions to a solution of 8-methyl-8-azabicyclo[3.2.1]octan-3-amine dihydrochloride and stirred at ambient temperature for 1 h. To the reaction mixture, methyl 3-formyl-1-methyl-1H-indazole-4-carboxylate (0.41 g, 1.9 mmol) from Step A of Example 6 in 1% acetic acid in dichloromethane (50 mL) was added and stirred at ambient temperature for 3 h. Sodium triacetoxyborohydride (1.2 g, 5.6 mmol) was added, and the resulting suspension was stirred for 16 h at ambient temperature. The solvent was removed under reduced pressure, and the crude material purified by column chromatography (silica gel, 10:1:0.1 dichloromethane/methanol/concentrated ammonium hydroxide) to afford methyl 1-methyl-3-((8-methyl-8-azabicyclo[3.2.1]octan-3-ylamino)methyl)-1H-indazole-4-carboxylate (0.54 g, 100%) as a yellow oil: $^1$H NMR (300 MHz, CDCl$_3$) δ 7.75 (d, J=7.5 Hz, 1H), 7.53 (d, J=8.5 Hz, 1H), 7.38 (t, J=6.0 Hz, 1H), 5.49 (s, 1H), 4.26 (s, 2H), 4.04 (s, 3H), 3.96 (s, 3H), 2.99-2.89 (m, 1H), 2.45 (s, 3H), 2.10-1.85 (m, 6H), 1.74-1.62 (m, 4H); LC/MS (ESI+) m/z 343 (M+H).

Step B: To a solution of methyl 1-methyl-3-((8-methyl-8-azabicyclo[3.2.1]octan-3-ylamino)methyl)-1H-indazole-4-carboxylate (0.54 g, 1.6 mmol) from Step A above in THF (5 mL) was added lithium hydroxide monohydrate (1.6 g, 38 mmol) in water (5 mL). The mixture was heated at 90° C. for 1 h and then concentrated under reduced pressure. The residue was dried overnight under vacuum to afford crude lithium 1-methyl-3-((8-methyl-8-azabicyclo[3.2.1]octan-3-ylamino)methyl)-1H-indazole-4-carboxylate (1.54 g), which was used in the next step without further purification: LC/MS (ESI+) m/z 329 (M+H).

Step C: A mixture of crude lithium 1-methyl-3-((8-methyl-8-azabicyclo[3.2.1]octan-3-ylamino)methyl)-1H-indazole-4-carboxylate (1.5 g) and HBTU (1.2 g, 3.2 mmol) in N,N-dimethylformamide (5 mL) was stirred at ambient temperature for 18 h. The reaction was concentrated under reduced pressure and the mixture was partitioned between dichloromethane and water. The aqueous layer was extracted with dichloromethane and the combined organic layers were dried (Na$_2$SO$_4$), filtered and concentrated under reduced pressure. The crude mixture was dissolved in methanol and precipitated using diethyl ether. The precipitate was filtered and dried under reduced pressure to afford 2-methyl-7-(8-methyl-8-azabicyclo[3.2.1]octan-3-yl)-7,8-dihydropyrazolo[3,4,5-de]isoquinolin-6(2H)-one (36 mg). This material was dissolved in methanol (1 mL) and treated with excess hydrochloric acid (1.25 M solution in methanol). The mixture was stirred for 1 h, filtered, concentrated under reduced pressure, and dried under vacuum to give 2-methyl-7-(8-methyl-8-azabicyclo[3.2.1]octan-3-yl)-7,8-dihydropyrazolo[3,4,5-de]isoquinolin-6(2H)-one, hydrochloride salt (20 mg, 4% over two steps) as an off-white solid: $^1$H NMR (500 MHz, DMSO-d$_6$) δ 9.51 (s, 1H), 7.74 (d, J=8.5 Hz, 1H), 7.53 (t, J=7.0 Hz, 1H), 7.43 (d, J=7.0 Hz, 1H), 5.04-4.93 (m, 3H), 4.08 (s, 3H), 3.99 (s, 2H), 2.73 (s, 3H), 2.44-2.39 (m, 2H), 2.33-2.27 (m, 2H), 2.03 (d, J=8.5 Hz, 2H), 1.84 (d, J=10.0 Hz, 2H); MS (ESI+) m/z 311 (M+H); HPLC>99% (AUC), t$_R$ 11.96 min.

Example 39

Compound Affinity for the Human 5-HT$_3$ Receptor

The relative affinity of the various compounds for the human 5-HT$_3$ receptor was measured in a radioligand binding assay, using a scintillation proximity assay (SPA) format. Test compounds were dissolved to 10 mM in 100% DMSO, then serially diluted at 10× assay concentrations in 100% DMSO in 96-well polypropylene plates and further diluted to 4× assay concentrations with the assay buffer. Samples were incubated in 50 mM Tris-HCl, pH 7.5, 3 mM MgCl$_2$, 1 mM EDTA and 10% DMSO with 10 nM [9-methyl-$^3$H]BRL-43694 (Perkin Elmer, Waltham, Mass.), 3 µg of human 5-HT$_3$ receptor membranes (Perkin Elmer, Waltham, Mass.) and 0.5 mg/mL SPA beads (WGA PVT, Amersham Biosciences) in a final volume of 0.2 mL. Binding reactions were set up in wells of PicoPlates-96 (Perkin Elmer, Waltham, Mass.) by adding consecutively 50 µL of each competing compound or buffer, SPA beads, the radioligand and 5-HT$_3$ receptor membranes. After an overnight incubation at room temperature on a Nutator mixer, plates were centrifuged for 15 min at 1,500 rpm, followed by incubation in the dark for 30 min. Radioactivity was counted in the TopCount microplate counter (Perkin Elmer) for 5 min. Total binding control contained compound dilution buffer only; nonspecific binding was determined in the presence of 30 µM MDL-72222. Specific binding was determined by subtracting nonspecific binding from total binding. All experiments were performed in duplicate using ten concentrations of competing ligand, with ondansetron included as a control in every run. IC$_{50}$ values were determined from specific binding data using XLfit4.1 curve fitting software from IDBS Ltd. The inhibition constant (K$_i$) was calculated from the Cheng Prusoff equation: (K$_i$=IC$_{50}$/(1+(L/K$_D$)), where L=concentration of radioligand in the assay, and K$_D$=affinity of the radioligand for the receptor.

Example 40

Agonist Activity at Recombinant Human 5-HT$_{3A}$ Receptors

Human embryonic kidney (HEK293) cells expressing the h5-HT$_{3A}$ receptor subunit were seeded directly into poly-D-lysine coated, black-walled, clear bottomed, 96 well plates with approximately 1×10$^5$ cells per well. After 48 hrs incubation in DMEM growth media (100 µL), cells were washed twice (each 200 µL) in Hank's balanced salt solution (Invitrogen) before incubation (1 hr) with Fluo-4 acetoxymethyl (AM) ester (100 µL, 2.5 µM; Molecular Probes). Cells were washed twice (each 200 µL) in Hank's balanced salt solution and incubated for a further 30 mins in Hank's balanced salt solution (100 µL) prior to assay (25° C.). Alteration in [Ca$^{2+}$]$_i$ was measured (relative fluorescence units [RFU]) using a Flexstation (excitation 488 nm and emission 515 nm; frequency of recording 3 sec). After recording for at least 80 sec, vehicle (Hank's balanced salt solution) or drug was automatically administered to the well (50 µL). Baseline was calculated from the 5 data points immediately prior to the first drug administration and the maximum response was that achieved over the 240 sec following drug administration. In all experiments the muscarinic receptor agonist carbachol (1 mM) was added 240 sec after the test drug administration. Muscarinic receptors are endogenously expressed by HEK293 cells; in every experiment, carbachol elicited a response comparable to the maximum response elicited by the maximal effective concentration of 5-HT.

Example 41 von Bezold-Jarisch Model In Vivo

5-HT$_3$ receptor modulators have proven efficacy in the treatment of human GI disorders as demonstrated by the approval of alosetron and ramosetron for IBS-D. In vivo activity at 5-HT$_3$ receptors can be assessed using the 5-HT$_3$ mediated transient bradycardia observed after the intravenous administration of 5-HT or 5-HT$_3$ selective agonists in anesthetized mice (von Bezold-Jarisch reflex). This is a well characterized and widely used model to assess 5-HT$_3$ receptor function in vivo (King et al., 5-*Hydroxtryptamine*-3 *Receptor Antagonists*, CRC Press, pp. 74-75 (1993), which is hereby incorporated by reference in its entirety). Certain compounds (Table 1) were evaluated for their ability to inhibit serotonin induced bradycardia in vivo in the mouse (Saxena et al., *Arch. Int. Pharmacodyn.*, 277:235-252 (1985), which is hereby incorporated by reference in its entirety). Test substances and vehicle [2% Tween 80] were each administered orally to a group of 5 male CD-1 (Crl.) mice each weighing 24±2 g. A dosing volume of 10 mL/kg was used. Sixty minutes later, 5-HT (0.1 mg/kg IV)-induced bradycardia was recorded in urethane (2250 mg/kg IP, given 10 minutes before 5-HT)-anesthetized animals. The highest oral dose tested is reported.

TABLE 1

Biological Activity of Exemplified Compounds

| Example Number | h5-HT$_{3A}$ K$_i$ (nM) | HEK293 h5-HT$_{3A}$* | Inhibition of 5-HT Induced Bradycardia in Mice |
|---|---|---|---|
| 4 | 1 | | |
| 5 | 13 | | |
| 6 | 1 | NR | 100% @ 3 mg/kg |
| 7 | 2 | | 93% @ 3 mg/kg |
| 8 | 1 | | 97% @ 0.3 mg/kg |
| 9 | 2 | | |
| 10 | 7 | | |
| 11 | 5 | | |
| 12 | 2 | 6% | 73% @ 1 mg/kg |
| 13 | 2 | 6% | |
| 14 | 2 | 4% | 90% @ 3 mg/kg |
| 15 | 3 | 3% | 96% @ 3 mg/kg |
| 16 | 5 | 35% | 87% @ 3 mg/kg |
| 17 | 5 | | |

TABLE 1-continued

Biological Activity of Exemplified Compounds

| Example Number | h5-HT$_{3A}$ K$_i$ (nM) | HEK293 h5-HT$_{3A}$* | Inhibition of 5-HT Induced Bradycardia in Mice |
|---|---|---|---|
| 18 | 29 | 9% | |
| 19 | 68 | | |
| 20 | 57 | | |
| 21 | 1 | | |
| 22 | 34 | | |
| 23 | 4 | | |
| 24 | 2 | | 91% @ 1 mg/kg |
| 25 | 1 | | 96% @ 1 mg/kg |
| 26 | 2 | | 94% @ 3 mg/kg |
| 27 | 2 | | |
| 28 | 108 | | |
| 29 | 3 | 17% | 94% @ 1 mg/kg |
| 30 | 25 | | |
| 31 | 1 | 5% | |
| 32 | 1 | | |
| 33 | 49 | 14% | |
| 34 | 8 | 13% | 88% @ 3 mg/kg |
| 35 | 13 | | |
| 36 | 49% inhibition @ 10 µM | | |
| 37 | 267 | | |
| 38 | 59 | | |
| Alosetron | 0.5 | NR | 95% @ 1 mg/kg |
| Ramosetron | 0.06 | NR | 77% @ 0.1 mg/kg |

*% agonist response at 10 µM is normalized to the response of 5-HT (5-HT response = 100% at 3 µM); NR = no response The present invention is not limited to the compounds found in the above examples, and many other compounds falling within the scope of the invention may also be prepared using the procedures set forth in the above synthetic schemes. The preparation of additional compounds of formula I using these methods will be apparent to one of ordinary skill in the chemical arts.

The invention has been described in detail with particular reference to some embodiments thereof, but it will be understood by those skilled in the art that variations and modifications can be effected within the spirit and scope of the invention.

What is claimed:

1. A compound having the following formula:

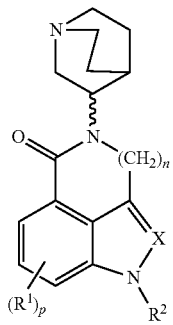

wherein:
X is CH or N;
each $R^1$ is independently selected from the group consisting of H, halogen, —OR$^4$, or $C_1$-$C_6$ alkyl, wherein $C_1$-$C_6$ alkyl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

$R^2$ is H;
$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;
$R^6$ is $C_1$-$C_4$ alkyl, $C_1$-$C_4$ haloalkyl, or phenyl;
$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;
n is 1 or 2; and
p is 0, 1, 2, or 3;
or an oxide thereof or a pharmaceutically acceptable salt thereof.

2. The compound according to claim 1 in the (S) configuration.

3. The compound according to claim 1 in the (R) configuration.

4. A pharmaceutical composition comprising a therapeutically effective amount of the compound according to claim 1 and a pharmaceutically acceptable carrier.

5. A method of treating irritable bowel syndrome comprising:
selecting a patient with irritable bowel syndrome; and
administering to the patient a therapeutically effective amount of a compound according to claim 1 or a pharmaceutically acceptable salt thereof.

6. The method according to claim 5 further comprising:
administering to the patient a therapeutically effective amount of a second serotonin 5-HT$_3$ receptor modulator or a serotonin 5-HT$_4$ receptor modulator.

7. The method according to claim 6, wherein the second serotonin 5HT$_3$ receptor modulator or serotonin 5HT$_4$ receptor modulator is selected from the group consisting of Alosetron, renzapride, cilansetron, Tegaserod, Prucalopride, ondansetron, somatostatin analogs, muscarinic receptor antagonists, laxatives, antispasmodics, antidepressants, antidiarrheal agents, prokinetic agents, peripheral opiate narcotic antagonists, and combinations thereof.

8. A method of treating emesis comprising:
selecting a patient with emesis; and
administering to the patient a therapeutically effective amount of a compound according to claim 1 or a pharmaceutically acceptable salt thereof.

9. The method according to claim 8 further comprising:
administering to the patient a therapeutically effective amount of one or more other anti-emetic compounds.

10. The method according to claim 9, wherein the one or more other anti-emetic compounds are selected from the group consisting of dexamethasone, alosetron, alprazolam, aprepitant, dimenhydrinate, diphenhydramine, dolasetron, tetrahydrocannabinol, nabilone, dronabinol, droperidol, granisetron, haloperidol, lorazepam, metoclopramide, midazolam, olanzapine, ondansetron, palonosetron, proclorperazine, promethazine, tropisetron, and combinations thereof.

* * * * *